US006350860B1

(12) United States Patent
Buyse et al.

(10) Patent No.: US 6,350,860 B1
(45) Date of Patent: Feb. 26, 2002

(54) INTERFERON-GAMMA-BINDING MOLECULES FOR TREATING SEPTIC SHOCK, CACHEXIA, IMMUNE DISEASES AND SKIN DISORDERS

(75) Inventors: Marie-Ange Buyse, Merelbeke; Erwin Sablon, Merchtem, both of (BE)

(73) Assignee: Innogenetics N.V., Ghent (NL)

( * ) Notice: Subject to any disclaimer, the term of this patent is extended or adjusted under 35 U.S.C. 154(b) by 0 days.

(21) Appl. No.: 09/485,737

(22) PCT Filed: Aug. 14, 1998

(86) PCT No.: PCT/EP98/05165

§ 371 Date: Feb. 14, 2000

§ 102(e) Date: Feb. 14, 2000

(87) PCT Pub. No.: WO99/09055

PCT Pub. Date: Feb. 25, 1999

(30) Foreign Application Priority Data

Aug. 18, 1997 (EP) ............................................. 97870122
Jun. 18, 1998 (EP) ............................................. 98870139

(51) Int. Cl.$^7$ ............................................... C07K 16/24
(52) U.S. Cl. .............................. 530/388.23; 530/387.3; 424/136.1
(58) Field of Search .......................... 530/387.1, 387.3, 530/388.23, 350; 424/133.1, 135.1, 145.1, 156.1, 136.1; 435/69.6

(56) References Cited

FOREIGN PATENT DOCUMENTS

WO WO 92 11018 A 7/1992

OTHER PUBLICATIONS

Adams, G. P. et al., "Highly Specific in Vivo Tumor Targeting by Monovalent and Divalent Forms of 741F8 Anti–c–erbB–2 Single–Chain Fv", *Cancer Research* 53: 4026–4034 (1993).
Rheinnecker, M. et al., "Multivalent Antibody Fragments with High Functional Affinity for a Tumor–Associated Carbohydrate Antigen" *Journal of Immunology* 157: 2989–2997 (1996).

Froyen, G. et al., "Potential therapeutic use of antibodies directed towards HuIFN–gamma", *Biotherapy* 10:49–57 (1997).
Leist, T. et al., "Enhanced Virus Replication and Inhibition of Lymphocytic Choriomeningitis Virus Disease in Anti–Gamma Interferon–Treated Mice", *Journal of Virology* 63:2813–2819 (1989).
Zhu, Z. et al., "Engineering and production of humanized anti–p185 $^{HER2}$/anti–CD3 bispecific antibodies for efficient tumor cell lysis.", *Proceedings of the American Association for Cancer Research* 37:468 (1996).
Iliades, P. et al., "Triabodies: single chain Fv fragments without a linker form trivalent trimers", *FEBS Letters* 409:437–441 (1997).
Paul, Fundamental Immunology, Chapter 8, p. 242, Raven Press, NY, 1993.*
Pack et al., J. Mol. Biol 246:28–34, 1995.*
Froyen et al., Molecular Immunology 30:805–812, 1993.*
Kortt et al., Protein Engineering 10:423–433, Apr. 1997.*
Billiau et al., Eur. J. Immunol. 17:1851–54, 1987.*
Terskikh et al., Proc. Natl. Acad. Sci. USA 94:1663–1668, Mar. 1997.*
Coloma et al., Nature Biotechnology 15:159–163, Feb. 1997.*

* cited by examiner

*Primary Examiner*—Sheela Huff
*Assistant Examiner*—Larry R. Helms
(74) *Attorney, Agent, or Firm*—Howrey Simon Arnold & White, LLP

(57) ABSTRACT

The present invention concerns molecules which bind and neutralize the cytokine interferon-gamma. More specifically, the present invention relates to sheep-derived antibodies and engineered antibody constructs, such as humanized single-chain Fv fragments, chimeric antibodies, diabodies, triabodies, tetravalent antibodies, peptabodies and hexabodies which can be used to treat diseases wherein interferon-gamma activity is pathogenic. Examples of such diseases are: septic shock, cachexia, multiple sclerosis and psoriasis.

14 Claims, 33 Drawing Sheets

```
ATG AAA TAC CTA TTG CCT ACG GCA GCC GCT GGA TTG TTA TTA CTC
MET Lys Tyr Leu Leu Pro Thr Ala Ala Ala Gly Leu Leu Leu Leu

GCT GCC CAA CCA GCG ATG GCC CAG GTG CAG CTG GTG CAG AGC GGT
Ala Ala Gln Pro Ala MET Ala Gln Val Gln Leu Val Gln Ser Gly

AGC GAA CTG AAA AAA CCG GGT GCG AGC GTT AAG ATC AGC TGC AAA
Ser Glu Leu Lys Lys Pro Gly Ala Ser Val Lys Ile Ser Cys Lys
                                        CDR1
GCG AGC GGT TAT ACC TTC ACC GAT TAC GGT ATG AAC TGG GTT AAA
Ala Ser Gly Tyr Thr Phe Thr Asp Tyr Gly MET Asn Trp Val Lys

CAG GCG CCG GGT CAA GGT CTG AAA TGG ATG GGT TGG ATC AAC ACC
Gln Ala Pro Gly Gln Gly Leu Lys Trp MET Gly Trp Ile Asn Thr
                                            CDR2
TAC ACC GGT GAA AGC ACC TAC GTT GAC GAT TTC AAA GGT CGT TTC
Tyr Thr Gly Glu Ser Thr Tyr Val Asp Asp Phe Lys Gly Arg Phe

GTT TTC AGC CTG GAT ACC AGC GTT AGC GCG GCC TAC CTG CAG ATC
Val Phe Ser Leu Asp Thr Ser Val Ser Ala Ala Tyr Leu Gln Ile

AGC TCT CTG AAA GCG GAA GAC ACC GCG ACC TAC TTC TGC GCG CGT
Ser Ser Leu Lys Ala Glu Asp Thr Ala Thr Tyr Phe Cys Ala Arg
                                                        CDR3
CGC GGT TTC TAC GCG ATG GAT TAC TGG GGC CAA GGG ACC ACG GTC
Arg Gly Phe Tyr Ala MET Asp Tyr Trp Gly Gln Gly Thr Thr Val
                                                    Linker
ACC GTC TCC TCA GGT GGA GGC GGT TCA GGC GGA GGT GGC TCT GGC
Thr Val Ser Ser Gly Gly Gly Gly Ser Gly Gly Gly Gly Ser Gly
GGT GGC GGA TCG GAC ATC GTA CTG ACC CAG AGC CCG GCG ACC ATG
Gly Gly Gly Ser Asp Ile Val Leu Thr Gln Ser Pro Ala Thr MET AGC GCG AGC CCG GGT GAA CGT GTT ACC CTG ACC TGC AGC GCG AGC
Ser Ala Ser Pro Gly Glu Arg Val Thr Leu Thr Cys Ser Ala Ser
```

FIG. 2A

```
                    CDR1
TCT AGC ATC AGC TAT ATG TTC TGG TAT CAT CAG CGT CCG GGT CAG
Ser Ser Ile Ser Tyr MET Phe Trp Tyr His Gln Arg Pro Gly Gln
                                    CDR2
AGC CCG CGT CTG TTG ATC TAT GAT ACC AGC AAC CTG GCG AGC GGT
Ser Pro Arg Leu Leu Ile Tyr Asp Thr Ser Asn Leu Ala Ser Gly

GTT CCG GCG CGT TTC AGC GGT AGC GGT AGC GGT ACC AGC TAT AGC
Val Pro Ala Arg Phe Ser Gly Ser Gly Ser Gly Thr Ser Tyr Ser

CTG ACC ATC AGC CGT ATG GAA CCG GAA GAT TTC GCG ACC TAT TTC
Leu Thr Ile Ser Arg MET Glu Pro Glu Asp Phe Ala Thr Tyr Phe
                    CDR3
TGC CAT CAG AGC TCT AGC TAT CCG TTC ACC TTC GGT CAG GGT ACC
Cys His Gln Ser Ser Ser Tyr Pro Phe Thr Phe Gly Gln Gly Thr
                    His6-Tag
AAA CTC GAG ATC AAA CGG CAC CAT CAC CAT CAC CAC TAA
Lys Leu Glu Ile Lys Arg His His His His His His ---
```

FIG. 2B

```
   1 ATGGATTTTCAAGTGCAGATTTTCAGCTTCCTGCTAATCA
  41 GTGCCTCAGTCATACTCTCGCAGGTGCAGCTGGTGCAGAG
  81 CGGTAGCGAACTGAAAAAACCGGGTGCGAGCGTTAAGATC
 121 AGCTGCAAAGCGAGCGGTTATACCTTCACCGATTACGGTA
 161 TGAACTGGGTTAAACAGGCGCCGGGTCAAGGTCTGAAATG
 201 GATGGGTTGGATCAACACCTACACCGGTGAAAGCACCTAC
 241 GTTGACGATTTCAAAGGTCGTTTCGTTTTCAGCCTGGATA
 281 CCAGCGTTAGCGCGGCCTACCTGCAGATCAGCTCTCTGAA
 321 AGCGGAAGACACCGCGACCTACTTCTGCGCGCGTCGCGGT
 361 TTCTACGCGATGGATTACTGGGGCCAAGGGACCACGGTCA
 401 CCGTCTCGAGCGCATCCACCAAGGGCCCATCGGTCTTCCC
 441 CCTGGCACCCTCCTCCAAGAGCACCTCTGGGGGCACAGCG
 481 GCCCTGGGCTGCCTGGTCAAGGACTACTTCCCCGAACCGG
 521 TGACGGTGTCGTGGAACTCAGGCGCCCTGACCAGCGGCGT
 561 GCACACCTTCCCGGCTGTCCTACAGTCCTCAGGACTCTAC
 601 TCCCTCAGCAGCGTGGTGACCGTGCCCTCCAGCAGCTTGG
 641 GCACCCAGACCTACATCTGCAACGTGAATCACAAGCCCAG
 681 CAACACCAAGGTGGACAAGAGAGTTGAGCCCAAATCTTGT
 721 GACAAAACTCACACATGCCCACCGTGCCCAGCACCTGAAC
 761 TCCTGGGGGACCGTCAGTCTTCCTCTTCCCCCCAAAACC
 801 CAAGGACACCCTCATGATCTCCCGGACCCCTGAGGTCACA
 841 TGCGTGGTGGTGGACGTGAGCCACGAAGACCCTGAGGTCA
 881 AGTTCAACTGGTACGTGGACGGCGTGGAGGTGCATAATGC
 921 CAAGACAAAGCCGCGGGAGGAGCAGTACAACAGCACGTAC
 961 CGTGTGGTCAGCGTCCTCACCGTCCTGCACCAGGACTGGC
1001 TGAATGGCAAGGAGTACAAGTGCAAGGTCTCCAACAAAGC
1041 CCTCCCAGCCTCCATCGAGAAAACCATCTCCAAAGCCAAA
1081 GGGCAGCCCCGAGAACCACAGGTGTACACCCTGCCCCCAT
1121 CCCGGGAGGAGATGACCAAGAACCAGGTCAGCCTGACCTG
1161 CCTGGTCAAAGGCTTCTATCCCAGCGACATCGCCGTGGAG
1201 TGGGAGAGCAATGGGCAGCCGGAGAACAACTACAAGACCA
1241 CGCCTCCCGTGCTGGACTCCGACGGCTCCTTCTTCCTCTA
1281 TAGCAAGCTCACCGTGGACAAGAGCAGGTGGCAGCAGGGG
1321 AACGTCTTCTCATGCTCCGTGATGCATGAGGCTCTGCACA
1361 ACCACTACACGCAGAAGAGCCTCTCCCTGTCTCCGGGTAA
1401 GCTT
```

FIG. 7

```
  1 ATGGATTTTCAAGTGCAGATTTTCAGCTTCCTGCTAATCA
 41 GTGCCTCAGTCATACTCTCGGACATCGAGCTGACCCAGAG
 81 CCCGGCGACCATGAGCGCGAGCCCGGGTGAACGTGTTACC
121 CTGACCTGCAGCGCGAGCTCTAGCATCAGCTATATGTTCT
161 GGTATCATCAGCGTCCGGGTCAGAGCCCGCGTCTGTTGAT
201 CTATGATACCAGCAACCTGGCGAGCGGTGTTCCGGCGCGT
241 TTCAGCGGTAGCGGTAGCGGTACCAGCTATAGCCTGACCA
281 TCAGCCGTATGGAACCGGAAGATTTCGCGACCTATTTCTG
321 CCATCAGAGCTCTAGCTATCCGTTCACCTTCGGTCAGGGT
361 ACCAAACTCGAGATCAAACGGACTGTGGCTGCACCATCTG
401 TCTTCATCTTCCCGCCATCTGATGAGCAGTTGAAATCTGG
441 AACTGCCTCTGTTGTGTGCCTGCTGAATAACTTCTATCCC
481 AGAGAGGCCAAAGTACAGTGGAAGGTGGATAACGCCCTCC
521 AATCGGGTAACTCCCAGGAGAGTGTCACAGAGCAGGACAG
561 CAAGGACAGCACCTACAGCCTCAGCAGCACCCTGACGCTG
601 AGCAAAGCAGACTACGAGAAACACAAAGTCTACGCCTGCG
641 AAGTCACCCATCAGGGCCTGAGCTCGCCCGTCACAAAGAG
681 CTTCAACAGGGGAGAGTGC
```

```
   1 CAGGTGCAGCTGGTGCAGAGCGGTAGCGAACTGAAAAAACCGGGTGCGAG
  51 CGTTAAGATCAGCTGCAAAGCGAGCGGTTATACCTTCACCGATTACGGTA
 101 TGAACTGGGTTAAACAGGCGCCGGGTCAAGGTCTGAAATGGATGGGTTGG
 151 ATCAACACCTACACCGGTGAAAGCACCTACGTTGACGATTTCAAAGGTCG
 201 TTTCGTTTTCAGCCTGGATACCAGCGTTAGCGCGGCCTACCTGCAGATCA
 251 GCTCTCTGAAAGCGGAAGACACCGCGACCTACTTCTGCGCGCGTCGCGGT
 301 TTCTACGCGATGGATTACTGGGGCCAAGGGACCACGGTCACCGTCTCCTC
 351 AGGTGGAGGCGGTTCAGGCGGAGGTGGCTCTGGCGGTGGCGGATCGGACA
 401 TCGTACTGACCCAGAGCCCGGCGACCATGAGCGCGAGCCCGGGTGAACGT
 451 GTTACCCTGACCTGCAGCGCGAGCTCTAGCATCAGCTATATGTTCTGGTA
 501 TCATCAGCGTCCGGGTCAGAGCCCGCGTCTGTTGATCTATGATACCAGCA
 551 ACCTGGCGAGCGGTGTTCCGGCGCGTTTCAGCGGTAGCGGTAGCGGTACC
 601 AGCTATAGCCTGACCATCAGCCGTATGGAACCGGAAGATTTCGCGACCTA
 651 TTTCTGCCATCAGAGCTCTAGCTATCCGTTCACCTTCGGTCAGGGTACCA
 701 AACTCGAGATCAAACGGACCCCGCTGGGTGATACCACTCATACCTCCGGA
 751 GGTGAACTGGAAGAGCTGTTGAAACATCTGAAAGAACTGCTGAAAGGTCC
 801 GCGGAAAGGTGAACTGGAGGAATTGCTGAAGCACCTGAAAGAGCTGTTGA
 851 AAGGTACCCCCCTGGGTGATACTACCCATACCAGCGGTCAGGTGCAACTA
 901 GTGCAGAGCGGTAGCGAACTGAAAAAACCGGGTGCGAGCGTTAAGATCAG
 951 CTGCAAAGCGAGCGGTTATACCTTCACCGATTACGGTATGAACTGGGTTA
1001 AACAGGCGCCGGGTCAAGGTCTGAAATGGATGGGTTGGATCAACACCTAC
1051 ACCGGTGAAAGCACCTACGTTGACGATTTCAAAGGTCGTTTCGTTTTCAG
1101 CCTGGATACCAGCGTTAGCGCGGCCTACCTGCAGATCAGCTCTCTGAAAG
1151 CGGAAGACACCGCGACCTACTTCTGCGCGCGTCGCGGTTTCTACGCGATG
1201 GATTACTGGGGCCAAGGGACCACGGTCACCGTCTCCTCAGGTGGAGGCGG
1251 TTCAGGCGGAGGTGGCTCTGGCGGTGGCGGATCGGACATCGTACTGACCC
1301 AGAGCCCGGCGACCATGAGCGCGAGCCCGGGTGAACGTGTTACCCTGACC
1351 TGCAGCGCGAGCTCTAGCATCAGCTATATGTTCTGGTATCATCAGCGTCC
1401 GGGTCAGAGCCCGCGTCTGTTGATCTATGATACCAGCAACCTGGCGAGCG
1451 GTGTTCCGGCGCGTTTCAGCGGTAGCGGTAGCGGTACCAGCTATAGCCTG
1501 ACCATCAGCCGTATGGAACCGGAAGATTTCGCGACCTATTTCTGCCATCA
1551 GAGCTCTAGCTATCCGTTCACCTTCGGTCAGGGTACCAAACTCGAGATCA
1601 AACGGCACCATCACCATCACCACTAA
```

FIG. 15

```
  1 QVQLVQSGSELKKPGASVKISCKASGYTFTDYGMNWVKQAPGQGLKWMGW
 51 INTYTGESTYVDDFKGRFVFSLDTSVSAAYLQISSLKAEDTATYFCARRG
101 FYAMDYWGQGTTVTVSSGGGGSGGGGSGGGGSDIVLTQSPATMSASPGER
151 VTLTCSASSSISYMFWYHQRPGQSPRLLIYDTSNLASGVPARFSGSGSGT
201 SYSLTISRMEPEDFATYFCHQSSSYPFTFGQGTKLEIKRTPLGDTTHTSG
251 GELEELLKHLKELLKGPRKGELEELLKHLKELLKGTPLGDTTHTSGQVQL
301 VQSGSELKKPGASVKISCKASGYTFTDYGMNWVKQAPGQGLKWMGWINTY
351 TGESTYVDDFKGRFVFSLDTSVSAAYLQISSLKAEDTATYFCARRGFYAM
401 DYWGQGTTVTVSSGGGGSGGGGSGGGGSDIVLTQSPATMSASPGERVTLT
451 CSASSSISYMFWYHQRPGQSPRLLIYDTSNLASGVPARFSGSGSGTSYSL
501 TISRMEPEDFATYFCHQSSSYPFTFGQGTKLEIKRHHHHHH
```

FIG. 16

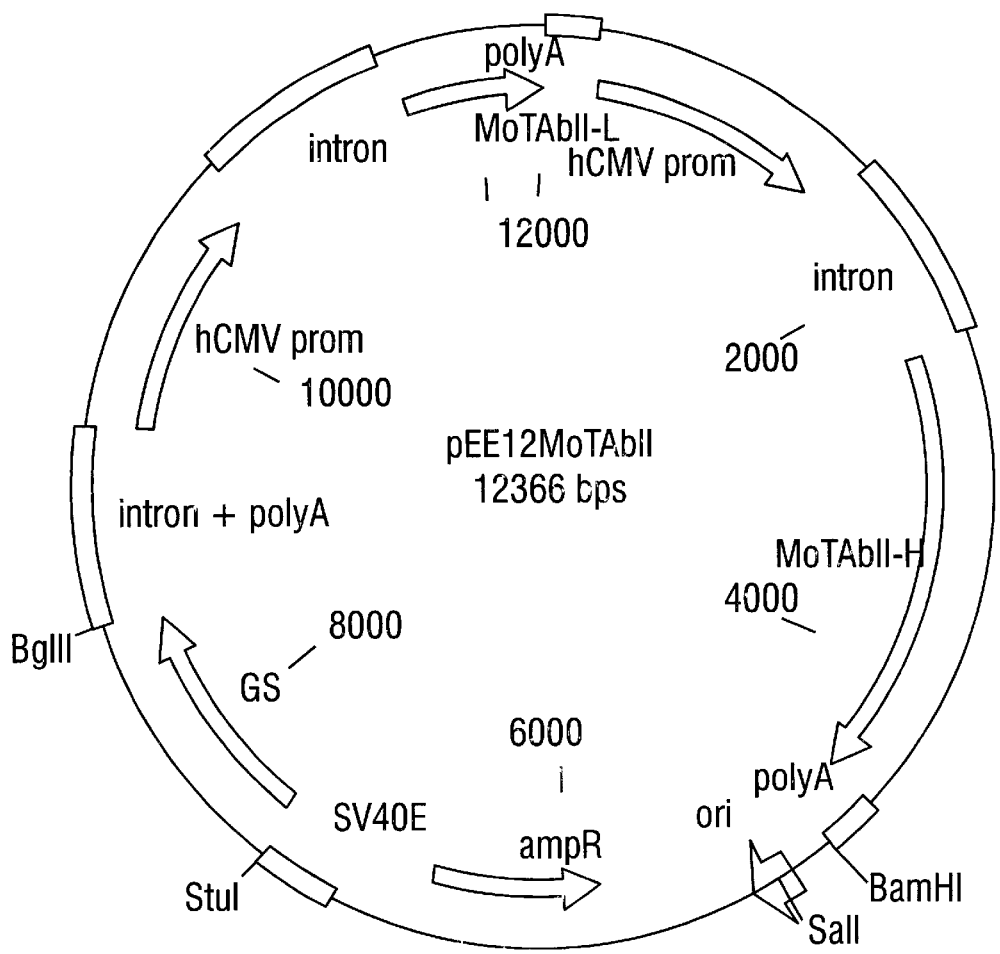

FIG. 17

```
1    ATGGATTTTCAAGTGCAGATTTTCAGCTTCCTGCTAATCA
41   GTGCCTCAGTCATACTCTCGCAGGTGCAGCTGGTGCAGAG
81   CGGTAGCGAACTGAAAAAACCGGGTGCGAGCGTTAAGATC
121  AGCTGCAAAGCGAGCGGTTATACCTTCACCGATTACGGTA
161  TGAACTGGGTTAAACAGGCGCCGGGTCAAGGTCTGAAATG
201  GATGGGTTGGATCAACACCTACACCGGTGAAAGCACCTAC
241  GTTGACGATTTCAAAGGTCGTTTCGTTTTCAGCCTGGATA
281  CCAGCGTTAGCGCGGCCTACCTGCAGATCAGCTCTCTGAA
321  AGCGGAAGACACCGCGACCTACTTCTGCGCGCGTCGCGGT
361  TTCTACGCGATGGATTACTGGGGCCAAGGGACCACGGTCA
401  CCGTCTCGAGCGCATCCACCAAGGGCCCATCGGTCTTCCC
441  CCTGGCACCCTCCTCCAAGAGCACCTCTGGGGGCACAGCG
481  GCCCTGGGCTGCCTGGTCAAGGACTACTTCCCCGAACCGG
521  TGACGGTGTCGTGGAACTCAGGCGCCCTGACCAGCGGCGT
561  GCACACCTTCCCGGCTGTCCTACAGTCCTCAGGACTCTAC
601  TCCCTCAGCAGCGTGGTGACCGTGCCCTCCAGCAGCTTGG
641  GCACCCAGACCTACATCTGCAACGTGAATCACAAGCCCAG
681  CAACACCAAGGTGGACAAGAGAGTTGAGCCCAAATCTTGT
721  GACAAAACTCACACATGCCCACCGTGCCCAGCACCTGAAC
761  TCCTGGGGGGACCGTCAGTCTTCCTCTTCCCCCCAAAACC
801  CAAGGACACCCTCATGATCTCCCGGACCCCTGAGGTCACA
841  TGCGTGGTGGTGGACGTGAGCCACGAAGACCCTGAGGTCA
881  AGTTCAACTGGTACGTGGACGGCGTGGAGGTGCATAATGC
921  CAAGACAAAGCCGCGGGAGGAGCAGTACAACAGCACGTAC
961  CGTGTGGTCAGCGTCCTCACCGTCCTGCACCAGGACTGGC
1001 TGAATGGCAAGGAGTACAAGTGCAAGGTCTCCAACAAAGC
1041 CCTCCCAGCCTCCATCGAGAAAACCATCTCCAAAGCCAAA
1081 GGGCAGCCCCGAGAACCACAGGTGTACACCCTGCCCCCAT
1121 CCCGGGAGGAGATGACCAAGAACCAGGTCAGCCTGACCTG
1161 CCTGGTCAAAGGCTTCTATCCCAGCGACATCGCCGTGGAG
1201 TGGGAGAGCAATGGGCAGCCGGAGAACAACTACAAGACCA
1241 CGCCTCCCGTGCTGGACTCCGACGGCTCCTTCTTCCTCTA
1281 TAGCAAGCTCACCGTGGACAAGAGCAGGTGGCAGCAGGGG
1321 AACGTCTTCTCATGCTCCGTGATGCATGAGGCTCTGCACA
```

FIG. 19A

```
1361 ACCACTACACGCAGAAGAGCCTCTCCCTGTCTCCGGGTAA
1401 GCTTGGCGGAGGCTCACAGGTGCAGCTGGTGCAGAGCGGT
1441 AGCGAACTGAAAAAACCGGGTGCGAGCGTTAAGATCAGCT
1481 GCAAAGCGAGCGGTTATACCTTCACCGATTACGGTATGAA
1521 CTGGGTTAAACAGGCGCCGGGTCAAGGTCTGAAATGGATG
1561 GGTTGGATCAACACCTACACCGGTGAAAGCACCTACGTTG
1601 ACGATTTCAAAGGTCGTTTCGTTTTCAGCCTGGATACCAG
1641 CGTTAGCGCGGCCTACCTGCAGATCAGCTCTCTGAAAGCG
1681 GAAGACACCGCGACCTACTTCTGCGCGCGTCGCGGTTTCT
1721 ACGCGATGGATTACTGGGGCCAAGGGACCACGGTCACCGT
1761 CTCCTCAGGTGGAGGCGGTTCAGGCGGAGGTGGCTCTGGC
1801 GGTGGCGGATCGGACATCGTACTGACCCAGAGCCCGGCGA
1841 CCATGAGCGCGAGCCCGGGTGAACGTGTTACCCTGACCTG
1881 CAGCGCGAGCTCTAGCATCAGCTATATGTTCTGGTATCAT
1921 CAGCGTCCGGGTCAGAGCCCGCGTCTGTTGATCTATGATA
1961 CCAGCAACCTGGCGAGCGGTGTTCCGGCGCGTTTCAGCGG
2001 TAGCGGTAGCGGTACCAGCTATAGCCTGACCATCAGCCGT
2041 ATGGAACCGGAAGATTTCGCGACCTATTTCTGCCATCAGA
2081 GCTCTAGCTATCCGTTCACCTTCGGTCAGGGTACCAAACT
2121 CGAGATCAAACGG
```

```
  1 QVQLVQSGSELKKPGASVKISCKASGYTFTDYGMNWVKQAPGQGLKWMGW
 51 INTYTGESTYVDDFKGRFVFSLDTSVSAAYLQISSLKAEDTATYFCARRG
101 FYAMDYWGQGTTVTVSSGGGGSGGGGSDIVLTQSPATMSASPGERVTLTC
151 SASSSISYMFWYHQRPGQSPRLLIYDTSNLASGVPARFSGSGSGTSYSLT
201 ISRMEPEDFATYFCHQSSSYPFTFGQGTKLEIKRHHHHHH
```

FIG. 22

```
  1 CAGGTGCAGCTGGTGCAGAGCGGTAGCGAACTGAAAAAACCGGGTGCGAG
 51 CGTTAAGATCAGCTGCAAAGCGAGCGGTTATACCTTCACCGATTACGGTA
101 TGAACTGGGTTAAACAGGCGCCGGGTCAAGGTCTGAAATGGATGGGTTGG
151 ATCAACACCTACACCGGTGAAAGCACCTACGTTGACGATTTCAAAGGTCG
201 TTTCGTTTTCAGCCTGGATACCAGCGTTAGCGCGGCCTACCTGCAGATCA
251 GCTCTCTGAAAGCGGAAGACACCGCGACCTACTTCTGCGCGCGTCGCGGT
301 TTCTACGCGATGGATTACTGGGGCCAAGGGACCACGGTCACCGTCTCCTC
351 AGGCGGAGGTGGCTCTGGCGGTGGCGGATCGGACATCGTACTGACCCAGA
401 GCCCGGCGACCATGAGCGCGAGCCCGGGTGAACGTGTTACCCTGACCTGC
451 AGCGCGAGCTCTAGCATCAGCTATATGTTCTGGTATCATCAGCGTCCGGG
501 TCAGAGCCCGCGTCTGTTGATCTATGATACCAGCAACCTGGCGAGCGGTG
551 TTCCGGCGCGTTTCAGCGGTAGCGGTAGCGGTACCAGCTATAGCCTGACC
601 ATCAGCCGTATGGAACCGGAAGATTTCGCGACCTATTTCTGCCATCAGAG
651 CTCTAGCTATCCGTTCACCTTCGGTCAGGGTACCAAACTCGAGATCAAAC
701 GG
```

FIG. 23

```
  1 QVQLVQSGSELKKPGASVKISCKASGYTFTDYGMNWVKQAPGQGLKWMGW
 51 INTYTGESTYVDDFKGRFVFSLDTSVSAAYLQISSLKAEDTATYFCARRG
101 FYAMDYWGQGTTVTVSSGGGGSDIVLTQSPATMSASPGERVTLTCSASSS
151 ISYMFWYHQRPGQSPRLLIYDTSNLASGVPARFSGSGSGTSYSLTISRME
201 PEDFATYFCHQSSSYPFTFGQGTKLEIKRHHHHHH
```

FIG. 24

```
  1 CAGGTGCAGCTGGTGCAGAGCGGTAGCGAACTGAAAAAACCGGGTGCGAG
 51 CGTTAAGATCAGCTGCAAAGCGAGCGGTTATACCTTCACCGATTACGGTA
101 TGAACTGGGTTAAACAGGCGCCGGGTCAAGGTCTGAAATGGATGGGTTGG
151 ATCAACACCTACACCGGTGAAAGCACCTACGTTGACGATTTCAAAGGTCG
201 TTTCGTTTTCAGCCTGGATACCAGCGTTAGCGCGGCCTACCTGCAGATCA
251 GCTCTCTGAAAGCGGAAGACACCGCGACCTACTTCTGCGCGCGTCGCGGT
301 TTCTACGCGATGGATTACTGGGGCCAAGGGACCACGGTCACCGTCTCCTC
351 AGGCGGTGGCGGATCGGACATCGTACTGACCCAGAGCCCGGCGACCATGA
401 GCGCGAGCCCGGGTGAACGTGTTACCCTGACCTGCAGCGCGAGCTCTAGC
451 ATCAGCTATATGTTCTGGTATCATCAGCGTCCGGGTCAGAGCCCGCGTCT
501 GTTGATCTATGATACCAGCAACCTGGCGAGCGGTGTTCCGGCGCGTTTCA
551 GCGGTAGCGGTAGCGGTACCAGCTATAGCCTGACCATCAGCCGTATGGAA
601 CCGGAAGATTTCGCGACCTATTTCTGCCATCAGAGCTCTAGCTATCCGTT
651 CACCTTCGGTCAGGGTACCAAACTCGAGATCAAACGG
```

FIG. 25

1    CAGGTGCAGCTGGTGCAGAGCGGTAGCGAACTGAAAAAACCGGGTGCGAG
51   CGTTAAGATCAGCTGCAAAGCGAGCGGTTATACCTTCACCGATTACGGTA
101  TGAACTGGGTTAAACAGGCGCCGGGTCAAGGTCTGAAATGGATGGGTTGG
151  ATCAACACCTACACCGGTGAAAGCACCTACGTTGACGATTTCAAAGGTCG
201  TTTCGTTTTCAGCCTGGATACCAGCGTTAGCGCGGCCTACCTGCAGATCA
251  GCTCTCTGAAAGCGGAAGACACCGCGACCTACTTCTGCGCGCGTCGCGGT
301  TTCTACGCGATGGATTACTGGGGCCAAGGGACCACGGTCACCGTCTCCTC
351  AGACATCGTACTGACCCAGAGCCCGGCGACCATGAGCGCGAGCCCGGGTG
401  AACGTGTTACCCTGACCTGCAGCGCGAGCTCTAGCATCAGCTATATGTTC
451  TGGTATCATCAGCGTCCGGGTCAGAGCCCGCGTCTGTTGATCTATGATAC
501  CAGCAACCTGGCGAGCGGTGTTCCGGCGCGTTTCAGCGGTAGCGGTAGCG
551  GTACCAGCTATAGCCTGACCATCAGCCGTATGGAACCGGAAGATTTCGCG
601  ACCTATTTCTGCCATCAGAGCTCTAGCTATCCGTTCACCTTCGGTCAGGG
651  TACCAAACTCGAGATCAAACGG

FIG. 27

1    QVQLVQSGSELKKPGASVKISCKASGYTFTDYGMNWVKQAPGQGLKWMGW
51   INTYTGESTYVDDFKGRFVFSLDTSVSAAYLQISSLKAEDTATYFCARRG
101  FYAMDYWGQGTTVTVSSDIVLTQSPATMSASPGERVTLTCSASSSISYMF
151  WYHQRPGQSPRLLIYDTSNLASGVPARFSGSGSGTSYSLTISRMEPEDFA
201  TYFCHQSSSYPFTFGQGTKLEIKRHHHHHH

FIG. 28

First experiment

Second experiment

SEQUENCE LISTING

<160> NUMBER OF SEQ ID NOS: 104

<210> SEQ ID NO 1
<211> LENGTH: 804
<212> TYPE: DNA
<213> ORGANISM: UNKNOWN
<220> FEATURE:

<223> OTHER INFORMATION: GENOMIC

<400> SEQUENCE: 1

| | | | | | |
|---|---|---|---|---|---|
| atgaaatacc | tattgcctac | ggcagccgct | ggattgttat | tactcgctgc | ccaaccagcg | 60 |
| atggcccagg | tgcagctggt | gcagagcggt | agcgaactga | aaaaaccggg | tgcgagcgtt | 120 |
| aagatcagct | gcaaagcgag | cggttatacc | ttcaccgatt | acggtatgaa | ctgggttaaa | 180 |
| caggcgccgg | gtcaaggtct | gaaatggatg | ggttggatca | acacctacac | cggtgaaagc | 240 |
| acctacgttg | acgatttcaa | aggtcgtttc | gttttcagcc | tggataccag | cgttagcgcg | 300 |
| gcctacctgc | agatcagctc | tctgaaagcg | gaagacaccg | cgacctactt | ctgcgcgcgt | 360 |
| cgcggtttct | acgcgatgga | ttactggggc | caagggacca | cggtcaccgt | ctcctcaggt | 420 |
| ggaggcggtt | caggcggagg | tggctctggc | ggtggcggat | cggacatcgt | actgacccag | 480 |
| agcccggcga | ccatgagcgc | gagcccgggt | gaacgtgtta | ccctgacctg | cagcgcgagc | 540 |
| tctagcatca | gctatatgtt | ctggtatcat | cagcgtccgg | gtcagagccc | gcgtctgttg | 600 |
| atctatgata | ccagcaacct | ggcgagcggt | gttccggcgc | gtttcagcgg | tagcggtagc | 660 |
| ggtaccagct | atagcctgac | catcagccgt | atggaaccgg | aagatttcgc | gacctatttc | 720 |
| tgccatcaga | gctctagcta | tccgttcacc | ttcggtcagg | gtaccaaact | cgagatcaaa | 780 |
| cggcaccatc | accatcacca | ctaa | | | | 804 |

<210> SEQ ID NO 2
<211> LENGTH: 267
<212> TYPE: PRT
<213> ORGANISM: Artificial Sequence
<220> FEATURE:
<223> OTHER INFORMATION: Synthetic

<400> SEQUENCE: 2

Met Lys Tyr Leu Leu Pro Thr Ala Ala Gly Leu Leu Leu Ala
1               5                   10                  15

Ala Gln Pro Ala Met Ala Gln Val Gln Leu Val Gln Ser Gly Ser Glu
            20                  25                  30

Leu Lys Lys Pro Gly Ala Ser Val Lys Ile Ser Cys Lys Ala Ser Gly
        35                  40                  45

Tyr Thr Phe Thr Asp Tyr Gly Met Asn Trp Val Lys Gln Ala Pro Gly
    50                  55                  60

Gln Gly Leu Lys Trp Met Gly Trp Ile Asn Thr Tyr Thr Gly Glu Ser
65                  70                  75                  80

Thr Tyr Val Asp Asp Phe Lys Gly Arg Phe Val Phe Ser Leu Asp Thr
                85                  90                  95

Ser Val Ser Ala Ala Tyr Leu Gln Ile Ser Ser Leu Lys Ala Glu Asp
            100                 105                 110

Thr Ala Thr Tyr Phe Cys Ala Arg Arg Gly Phe Tyr Ala Met Asp Tyr
        115                 120                 125

Trp Gly Gln Gly Thr Thr Val Thr Val Ser Ser Gly Gly Gly Gly Ser
    130                 135                 140

Gly Gly Gly Gly Ser Gly Gly Gly Ser Asp Ile Val Leu Thr Gln
145                 150                 155                 160

Ser Pro Ala Thr Met Ser Ala Ser Pro Gly Glu Arg Val Thr Leu Thr
                165                 170                 175

Cys Ser Ala Ser Ser Ser Ile Ser Tyr Met Phe Trp Tyr His Gln Arg
            180                 185                 190

Pro Gly Gln Ser Pro Arg Leu Leu Ile Tyr Asp Thr Ser Asn Leu Ala

```
                195                 200                 205
Ser Gly Val Pro Ala Arg Phe Ser Gly Ser Gly Ser Gly Thr Ser Tyr
    210                 215                 220

Ser Leu Thr Ile Ser Arg Met Glu Pro Glu Asp Phe Ala Thr Tyr Phe
225                 230                 235                 240

Cys His Gln Ser Ser Ser Tyr Pro Phe Thr Phe Gly Gln Gly Thr Lys
                245                 250                 255

Leu Glu Ile Lys Arg His His His His His
            260                 265
```

<210> SEQ ID NO 3
<211> LENGTH: 40
<212> TYPE: DNA
<213> ORGANISM: UNKNOWN
<220> FEATURE:
<223> OTHER INFORMATION: GENOMIC

<400> SEQUENCE: 3
cgcgcagccg ctggattgtt attactcgct gcccaaccag                    40

<210> SEQ ID NO 4
<211> LENGTH: 40
<212> TYPE: DNA
<213> ORGANISM: UNKNOWN
<220> FEATURE:
<223> OTHER INFORMATION: GENOMIC

<400> SEQUENCE: 4
cagctgcacc tgggccatcg ctggttgggc agcgagtaat                    40

<210> SEQ ID NO 5
<211> LENGTH: 40
<212> TYPE: DNA
<213> ORGANISM: UNKNOWN
<220> FEATURE:
<223> OTHER INFORMATION: GENOMIC

<400> SEQUENCE: 5
cgatggccca ggtgcagctg gtgcagagcg gtagcgaact                    40

<210> SEQ ID NO 6
<211> LENGTH: 40
<212> TYPE: DNA
<213> ORGANISM: UNKNOWN
<220> FEATURE:
<223> OTHER INFORMATION: GENOMIC

<400> SEQUENCE: 6
cgctcgcacc cggttttttc agttcgctac cgctctgcac                    40

<210> SEQ ID NO 7
<211> LENGTH: 40
<212> TYPE: DNA
<213> ORGANISM: UNKNOWN
<220> FEATURE:
<223> OTHER INFORMATION: GENOMIC

<400> SEQUENCE: 7
gaaaaaaccg ggtgcgagcg ttaagatcag ctgcaaagcg                    40

<210> SEQ ID NO 8
<211> LENGTH: 40
<212> TYPE: DNA
<213> ORGANISM: UNKNOWN

```
<220> FEATURE:
<223> OTHER INFORMATION: GENOMIC

<400> SEQUENCE: 8
tcggtgaagg tataaccgct cgctttgcag ctgatcttaa                              40

<210> SEQ ID NO 9
<211> LENGTH: 40
<212> TYPE: DNA
<213> ORGANISM: UNKNOWN
<220> FEATURE:
<223> OTHER INFORMATION: GENOMIC

<400> SEQUENCE: 9
agcggttata ccttcaccga ttacggtatg aactgggtta                              40

<210> SEQ ID NO 10
<211> LENGTH: 40
<212> TYPE: DNA
<213> ORGANISM: UNKNOWN
<220> FEATURE:
<223> OTHER INFORMATION: GENOMIC

<400> SEQUENCE: 10
accttgaccc ggcgcctgtt taacccagtt cataccgtaa                              40

<210> SEQ ID NO 11
<211> LENGTH: 40
<212> TYPE: DNA
<213> ORGANISM: UNKNOWN
<220> FEATURE:
<223> OTHER INFORMATION: GENOMIC

<400> SEQUENCE: 11
aacaggcgcc gggtcaaggt ctgaaatgga tgggttggat                              40

<210> SEQ ID NO 12
<211> LENGTH: 40
<212> TYPE: DNA
<213> ORGANISM: UNKNOWN
<220> FEATURE:
<223> OTHER INFORMATION: GENOMIC

<400> SEQUENCE: 12
tttcaccggt gtaggtgttg atccaaccca tccatttcag                              40

<210> SEQ ID NO 13
<211> LENGTH: 40
<212> TYPE: DNA
<213> ORGANISM: UNKNOWN
<220> FEATURE:
<223> OTHER INFORMATION: GENOMIC

<400> SEQUENCE: 13
caacacctac accggtgaaa gcacctacgt tgacgatttc                              40

<210> SEQ ID NO 14
<211> LENGTH: 40
<212> TYPE: DNA
<213> ORGANISM: UNKNOWN
<220> FEATURE:
<223> OTHER INFORMATION: GENOMIC

<400> SEQUENCE: 14
ctgaaaacga aacgaccttt gaaatcgtca acgtaggtgc                              40
```

-continued

<210> SEQ ID NO 15
<211> LENGTH: 40
<212> TYPE: DNA
<213> ORGANISM: UNKNOWN
<220> FEATURE:
<223> OTHER INFORMATION: GENOMIC

<400> SEQUENCE: 15
aaaggtcgtt tcgttttcag cctggatacc agcgttagcg                                    40

<210> SEQ ID NO 16
<211> LENGTH: 40
<212> TYPE: DNA
<213> ORGANISM: UNKNOWN
<220> FEATURE:
<223> OTHER INFORMATION: GENOMIC

<400> SEQUENCE: 16
gctgatctgc aggtaggccg cgctaacgct ggtatccagg                                    40

<210> SEQ ID NO 17
<211> LENGTH: 40
<212> TYPE: DNA
<213> ORGANISM: UNKNOWN
<220> FEATURE:
<223> OTHER INFORMATION: GENOMIC

<400> SEQUENCE: 17
cggcctacct gcagatcagc tctctgaaag cggaagacac                                    40

<210> SEQ ID NO 18
<211> LENGTH: 40
<212> TYPE: DNA
<213> ORGANISM: UNKNOWN
<220> FEATURE:
<223> OTHER INFORMATION: GENOMIC

<400> SEQUENCE: 18
gcgcgcagaa gtaggtcgcg gtgtcttccg ctttcagaga                                    40

<210> SEQ ID NO 19
<211> LENGTH: 40
<212> TYPE: DNA
<213> ORGANISM: UNKNOWN
<220> FEATURE:
<223> OTHER INFORMATION: GENOMIC

<400> SEQUENCE: 19
cgcgacctac ttctgcgcgc gtcgcggttt ctacgcgatg                                    40

<210> SEQ ID NO 20
<211> LENGTH: 41
<212> TYPE: DNA
<213> ORGANISM: UNKNOWN
<220> FEATURE:
<223> OTHER INFORMATION: GENOMIC

<400> SEQUENCE: 20
gcgcccttgg ccccagtaat ccatcgcgta gaaaccgcga c                                  41

<210> SEQ ID NO 21
<211> LENGTH: 25
<212> TYPE: DNA
<213> ORGANISM: UNKNOWN
<220> FEATURE:
<223> OTHER INFORMATION: GENOMIC

<400> SEQUENCE: 21
cgcgcagccg ctggattgtt attac                                              25

<210> SEQ ID NO 22
<211> LENGTH: 21
<212> TYPE: DNA
<213> ORGANISM: UNKNOWN
<220> FEATURE:
<223> OTHER INFORMATION: GENOMIC

<400> SEQUENCE: 22
gcgcccttgg ccccagtaat c                                                  21

<210> SEQ ID NO 23
<211> LENGTH: 48
<212> TYPE: DNA
<213> ORGANISM: UNKNOWN
<220> FEATURE:
<223> OTHER INFORMATION: GENOMIC

<400> SEQUENCE: 23
cgcggtatac tgacccagag cccggcgacc atgagcgcga gcccgggt                     48

<210> SEQ ID NO 24
<211> LENGTH: 40
<212> TYPE: DNA
<213> ORGANISM: UNKNOWN
<220> FEATURE:
<223> OTHER INFORMATION: GENOMIC

<400> SEQUENCE: 24
caggtcaggg taacacgttc acccgggctc gcgctcatgg                              40

<210> SEQ ID NO 25
<211> LENGTH: 40
<212> TYPE: DNA
<213> ORGANISM: UNKNOWN
<220> FEATURE:
<223> OTHER INFORMATION: GENOMIC

<400> SEQUENCE: 25
gaacgtgtta ccctgacctg cagcgcgagc tctagcatca                              40

<210> SEQ ID NO 26
<211> LENGTH: 40
<212> TYPE: DNA
<213> ORGANISM: UNKNOWN
<220> FEATURE:
<223> OTHER INFORMATION: GENOMIC

<400> SEQUENCE: 26
atgataccag aacatatagc tgatgctaga gctcgcgctg                              40

<210> SEQ ID NO 27
<211> LENGTH: 40
<212> TYPE: DNA
<213> ORGANISM: UNKNOWN
<220> FEATURE:
<223> OTHER INFORMATION: GENOMIC

<400> SEQUENCE: 27
gctatatgtt ctggtatcat cagcgtccgg gtcagagccc                              40

<210> SEQ ID NO 28

```
<211> LENGTH: 40
<212> TYPE: DNA
<213> ORGANISM: UNKNOWN
<220> FEATURE:
<223> OTHER INFORMATION: GENOMIC

<400> SEQUENCE: 28
tatcatagat caacagacgc gggctctgac ccggacgctg                        40

<210> SEQ ID NO 29
<211> LENGTH: 40
<212> TYPE: DNA
<213> ORGANISM: UNKNOWN
<220> FEATURE:
<223> OTHER INFORMATION: GENOMIC

<400> SEQUENCE: 29
gcgtctgttg atctatgata ccagcaacct ggcgagcggt                        40

<210> SEQ ID NO 30
<211> LENGTH: 40
<212> TYPE: DNA
<213> ORGANISM: UNKNOWN
<220> FEATURE:
<223> OTHER INFORMATION: GENOMIC

<400> SEQUENCE: 30
ccgctgaaac gcgccggaac accgctcgcc aggttgctgg                        40

<210> SEQ ID NO 31
<211> LENGTH: 40
<212> TYPE: DNA
<213> ORGANISM: UNKNOWN
<220> FEATURE:
<223> OTHER INFORMATION: GENOMIC

<400> SEQUENCE: 31
gttccggcgc gtttcagcgg tagcggtagc ggtaccagct                        40

<210> SEQ ID NO 32
<211> LENGTH: 40
<212> TYPE: DNA
<213> ORGANISM: UNKNOWN
<220> FEATURE:
<223> OTHER INFORMATION: GENOMIC

<400> SEQUENCE: 32
acggctgatg gtcaggctat agctggtacc gctaccgcta                        40

<210> SEQ ID NO 33
<211> LENGTH: 40
<212> TYPE: DNA
<213> ORGANISM: UNKNOWN
<220> FEATURE:
<223> OTHER INFORMATION: GENOMIC

<400> SEQUENCE: 33
atagcctgac catcagccgt atggaaccgg aagatttcgc                        40

<210> SEQ ID NO 34
<211> LENGTH: 40
<212> TYPE: DNA
<213> ORGANISM: UNKNOWN
<220> FEATURE:
<223> OTHER INFORMATION: GENOMIC

<400> SEQUENCE: 34
```

-continued tctgatggca gaaataggtc gcgaaatctt ccggttccat                    40

<210> SEQ ID NO 35
<211> LENGTH: 40
<212> TYPE: DNA
<213> ORGANISM: UNKNOWN
<220> FEATURE:
<223> OTHER INFORMATION: GENOMIC

<400> SEQUENCE: 35
gacctatttc tgccatcaga gctctagcta tccgttcacc                    40

<210> SEQ ID NO 36
<211> LENGTH: 48
<212> TYPE: DNA
<213> ORGANISM: UNKNOWN
<220> FEATURE:
<223> OTHER INFORMATION: GENOMIC

<400> SEQUENCE: 36
cgcgctcgag tttggtaccc tgaccgaagg tgaacggata gctagagc           48

<210> SEQ ID NO 37
<211> LENGTH: 21
<212> TYPE: DNA
<213> ORGANISM: UNKNOWN
<220> FEATURE:
<223> OTHER INFORMATION: GENOMIC

<400> SEQUENCE: 37
cgcggtatac tgacccagag c                                       21

<210> SEQ ID NO 38
<211> LENGTH: 22
<212> TYPE: DNA
<213> ORGANISM: UNKNOWN
<220> FEATURE:
<223> OTHER INFORMATION: GENOMIC

<400> SEQUENCE: 38
cgcgctcgag tttggtaccc tg                                      22

<210> SEQ ID NO 39
<211> LENGTH: 26
<212> TYPE: DNA
<213> ORGANISM: UNKNOWN
<220> FEATURE:
<223> OTHER INFORMATION: GENOMIC

<400> SEQUENCE: 39
tcgagatcaa acggtaatag ccatgg                                  26

<210> SEQ ID NO 40
<211> LENGTH: 26
<212> TYPE: DNA
<213> ORGANISM: UNKNOWN
<220> FEATURE:
<223> OTHER INFORMATION: GENOMIC

<400> SEQUENCE: 40
aattccatgg ctattaccgt ttgatc                                  26

<210> SEQ ID NO 41
<211> LENGTH: 32
<212> TYPE: DNA

<213> ORGANISM: UNKNOWN
<220> FEATURE:
<223> OTHER INFORMATION: GENOMIC

<400> SEQUENCE: 41
tcgaagctta gtactgtggc tgcaccatct gt         32

<210> SEQ ID NO 42
<211> LENGTH: 32
<212> TYPE: DNA
<213> ORGANISM: UNKNOWN
<220> FEATURE:
<223> OTHER INFORMATION: GENOMIC

<400> SEQUENCE: 42
gtcgaattct gcgcactctc ccctgttgaa gc         32

<210> SEQ ID NO 43
<211> LENGTH: 48
<212> TYPE: DNA
<213> ORGANISM: UNKNOWN
<220> FEATURE:
<223> OTHER INFORMATION: GENOMIC

<400> SEQUENCE: 43
ctagaattct gcgcatccac caagggccca tcggtcttcc ccctggca    48

<210> SEQ ID NO 44
<211> LENGTH: 36
<212> TYPE: DNA
<213> ORGANISM: UNKNOWN
<220> FEATURE:
<223> OTHER INFORMATION: GENOMIC

<400> SEQUENCE: 44
gtaaagcttg agctcttacc cggagacagg gagagg         36

<210> SEQ ID NO 45
<211> LENGTH: 40
<212> TYPE: DNA
<213> ORGANISM: UNKNOWN
<220> FEATURE:
<223> OTHER INFORMATION: GENOMIC

<400> SEQUENCE: 45
gtcccccggg tacctctaga atggattttc aagtgcagat         40

<210> SEQ ID NO 46
<211> LENGTH: 40
<212> TYPE: DNA
<213> ORGANISM: UNKNOWN
<220> FEATURE:
<223> OTHER INFORMATION: GENOMIC

<400> SEQUENCE: 46
tttcagcttc ctgctaatca gtgcctcagt catactctcg         40

<210> SEQ ID NO 47
<211> LENGTH: 40
<212> TYPE: DNA
<213> ORGANISM: UNKNOWN
<220> FEATURE:
<223> OTHER INFORMATION: GENOMIC

<400> SEQUENCE: 47
ctctgggtca gctcgatgtc cgagagtatg actgaggcac         40

<210> SEQ ID NO 48
<211> LENGTH: 40
<212> TYPE: DNA
<213> ORGANISM: UNKNOWN
<220> FEATURE:
<223> OTHER INFORMATION: GENOMIC

<400> SEQUENCE: 48
tgattagcag gaagctgaaa atctgcactt gaaaatccat       40

<210> SEQ ID NO 49
<211> LENGTH: 23
<212> TYPE: DNA
<213> ORGANISM: UNKNOWN
<220> FEATURE:
<223> OTHER INFORMATION: GENOMIC

<400> SEQUENCE: 49
gtcccccggg tacctctaga atg       23

<210> SEQ ID NO 50
<211> LENGTH: 21
<212> TYPE: DNA
<213> ORGANISM: UNKNOWN
<220> FEATURE:
<223> OTHER INFORMATION: GENOMIC

<400> SEQUENCE: 50
ctctgggtca gctcgatgtc c       21

<210> SEQ ID NO 51
<211> LENGTH: 27
<212> TYPE: DNA
<213> ORGANISM: UNKNOWN
<220> FEATURE:
<223> OTHER INFORMATION: GENOMIC

<400> SEQUENCE: 51
gacatcgagc tgacccagag cccggcg       27

<210> SEQ ID NO 52
<211> LENGTH: 22
<212> TYPE: DNA
<213> ORGANISM: UNKNOWN
<220> FEATURE:
<223> OTHER INFORMATION: GENOMIC

<400> SEQUENCE: 52
cgcgctcgag tttggtaccc tg       22

<210> SEQ ID NO 53
<211> LENGTH: 38
<212> TYPE: DNA
<213> ORGANISM: UNKNOWN
<220> FEATURE:
<223> OTHER INFORMATION: GENOMIC

<400> SEQUENCE: 53
gcgcctcgag atcaaacgga ctgtggctgc accatctg       38

<210> SEQ ID NO 54
<211> LENGTH: 32
<212> TYPE: DNA
<213> ORGANISM: UNKNOWN
<220> FEATURE:

<223> OTHER INFORMATION: GENOMIC

<400> SEQUENCE: 54
gccggaattc ctagcactct ccctgttga ag                32

<210> SEQ ID NO 55
<211> LENGTH: 40
<212> TYPE: DNA
<213> ORGANISM: UNKNOWN
<220> FEATURE:
<223> OTHER INFORMATION: GENOMIC

<400> SEQUENCE: 55
ctctgcacca gctgcacctg cgagagtatg actgaggcac                40

<210> SEQ ID NO 56
<211> LENGTH: 21
<212> TYPE: DNA
<213> ORGANISM: UNKNOWN
<220> FEATURE:
<223> OTHER INFORMATION: GENOMIC

<400> SEQUENCE: 56
ctctgcacca gctgcacctg c                21

<210> SEQ ID NO 57
<211> LENGTH: 26
<212> TYPE: DNA
<213> ORGANISM: UNKNOWN
<220> FEATURE:
<223> OTHER INFORMATION: GENOMIC

<400> SEQUENCE: 57
caggtgcagc tggtgcagag cggtag                26

<210> SEQ ID NO 58
<211> LENGTH: 45
<212> TYPE: DNA
<213> ORGANISM: UNKNOWN
<220> FEATURE:
<223> OTHER INFORMATION: GENOMIC

<400> SEQUENCE: 58
cgccggctcg agacggtgac cgtggtccct tggccccagt aatcc                45

<210> SEQ ID NO 59
<211> LENGTH: 21
<212> TYPE: DNA
<213> ORGANISM: UNKNOWN
<220> FEATURE:
<223> OTHER INFORMATION: GENOMIC

<400> SEQUENCE: 59
cgccggctcg agacggtgac c                21

<210> SEQ ID NO 60
<211> LENGTH: 26
<212> TYPE: DNA
<213> ORGANISM: UNKNOWN
<220> FEATURE:
<223> OTHER INFORMATION: GENOMIC

<400> SEQUENCE: 60
gccgctcgag cgcatccacc aagggc                26

```
<210> SEQ ID NO 61
<211> LENGTH: 39
<212> TYPE: DNA
<213> ORGANISM: UNKNOWN
<220> FEATURE:
<223> OTHER INFORMATION: GENOMIC

<400> SEQUENCE: 61
gccggaattc gctaaagctt acccggagac agggagagg                39

<210> SEQ ID NO 62
<211> LENGTH: 26
<212> TYPE: DNA
<213> ORGANISM: UNKNOWN
<220> FEATURE:
<223> OTHER INFORMATION: GENOMIC

<400> SEQUENCE: 62
gccctcccag cctccatcga gaaaac                              26

<210> SEQ ID NO 63
<211> LENGTH: 26
<212> TYPE: DNA
<213> ORGANISM: UNKNOWN
<220> FEATURE:
<223> OTHER INFORMATION: GENOMIC

<400> SEQUENCE: 63
gttttctcga tggaggctgg gagggc                              26

<210> SEQ ID NO 64
<211> LENGTH: 15
<212> TYPE: DNA
<213> ORGANISM: UNKNOWN
<220> FEATURE:
<223> OTHER INFORMATION: GENOMIC

<400> SEQUENCE: 64
taatacgact cacta                                          15

<210> SEQ ID NO 65
<211> LENGTH: 18
<212> TYPE: DNA
<213> ORGANISM: UNKNOWN
<220> FEATURE:
<223> OTHER INFORMATION: GENOMIC

<400> SEQUENCE: 65
atttaggtga cactatag                                       18

<210> SEQ ID NO 66
<211> LENGTH: 1404
<212> TYPE: DNA
<213> ORGANISM: UNKNOWN
<220> FEATURE:
<223> OTHER INFORMATION: GENOMIC

<400> SEQUENCE: 66
atggattttc aagtgcagat tttcagcttc ctgctaatca gtgcctcagt catactctcg     60
caggtgcagc tggtgcagag cggtagcgaa ctgaaaaaac cgggtgcgag cgttaagatc    120
agctgcaaag cgagcggtta taccttcacc gattacggta tgaactgggt taaacaggcg    180
ccgggtcaag gtctgaaatg gatgggttgg atcaacacct acaccggtga agcacctac     240 gttgacgatt tcaaaggtcg tttcgttttc agcctggata ccagcgttag cgcggcctac    300
```

-continued

```
ctgcagatca gctctctgaa agcggaagac accgcgacct acttctgcgc gcgtcgcggt      360
ttctacgcga tggattactg gggccaaggg accacggtca ccgtctcgag cgcatccacc      420
aagggcccat cggtcttccc cctggcaccc tcctccaaga gcacctctgg ggcacagcg       480
gccctgggct gcctggtcaa ggactacttc cccgaaccgg tgacggtgtc gtggaactca      540
ggcgccctga ccagcggcgt gcacaccttc ccggctgtcc tacagtcctc aggactctac      600
tccctcagca gcgtggtgac cgtgccctcc agcagcttgg gcacccagac ctacatctgc      660
aacgtgaatc acaagcccag caacaccaag gtggacaaga gagttgagcc caaatcttgt      720
gacaaaactc acacatgccc accgtgccca gcacctgaac tcctgggggg accgtcagtc      780
ttcctcttcc ccccaaaacc caaggacacc ctcatgatct cccggacccc tgaggtcaca      840
tgcgtggtgg tggacgtgag ccacgaagac cctgaggtca agttcaactg gtacgtggac      900
ggcgtggagg tgcataatgc caagacaaag ccgcgggagg agcagtacaa cagcacgtac      960
cgtgtggtca gcgtcctcac cgtcctgcac caggactggc tgaatggcaa ggagtacaag     1020
tgcaaggtct ccaacaaagc cctcccagcc tccatcgaga aaaccatctc aaaagccaaa     1080
gggcagcccc gagaaccaca ggtgtacacc ctgcccccat cccgggagga gatgaccaag     1140
aaccaggtca gcctgacctg cctggtcaaa ggcttctatc ccagcgacat cgccgtggag     1200
tgggagagca atgggcagcc ggagaacaac tacaagacca cgcctcccgt gctggactcc     1260
gacggctcct tcttcctcta tagcaagctc accgtggaca agagcaggtg gcagcagggg     1320
aacgtcttct catgctccgt gatgcatgag gctctgcaca accactacac gcagaagagc     1380
ctctccctgt ctccgggtaa gctt                                            1404
```

<210> SEQ ID NO 67
<211> LENGTH: 468
<212> TYPE: PRT
<213> ORGANISM: Artificial Sequence
<220> FEATURE:
<223> OTHER INFORMATION: SYNTHETIC

<400> SEQUENCE: 67

```
Met Asp Phe Gln Val Gln Ile Phe Ser Phe Leu Leu Ile Ser Ala Ser
1               5                   10                  15

Val Ile Leu Ser Gln Val Gln Leu Val Gln Ser Gly Ser Glu Leu Lys
            20                  25                  30

Lys Pro Gly Ala Ser Val Lys Ile Ser Cys Lys Ala Ser Gly Tyr Thr
        35                  40                  45

Phe Thr Asp Tyr Gly Met Asn Trp Val Lys Gln Ala Pro Gly Gln Gly
    50                  55                  60

Leu Lys Trp Met Gly Trp Ile Asn Thr Tyr Thr Gly Glu Ser Thr Tyr
65                  70                  75                  80

Val Asp Asp Phe Lys Gly Arg Phe Val Phe Ser Leu Asp Thr Ser Val
                85                  90                  95

Ser Ala Ala Tyr Leu Gln Ile Ser Ser Leu Lys Ala Glu Asp Thr Ala
            100                 105                 110

Thr Tyr Phe Cys Ala Arg Arg Gly Phe Tyr Ala Met Asp Tyr Trp Gly
        115                 120                 125

Gln Gly Thr Thr Val Thr Val Ser Ser Ala Ser Thr Lys Gly Pro Ser
    130                 135                 140

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
```

```
                  165                 170                 175
        Ser Trp Asn Ser Gly Ala Leu Thr Ser Gly Val His Thr Phe Pro Ala
                        180                 185                 190

Val Leu Gln Ser Ser Gly Leu Tyr Ser Leu Ser Val Val Thr Val
                        195                 200                 205

Pro Ser Ser Leu Gly Thr Gln Thr Tyr Ile Cys Asn Val Asn His
                        210                 215                 220

Lys Pro Ser Asn Thr Lys Val Asp Lys Arg Val Glu Pro Lys Ser Cys
        225                 230                 235                 240

Asp Lys Thr His Thr Cys Pro Pro Cys Pro Ala Pro Glu Leu Leu Gly
                        245                 250                 255

Gly Pro Ser Val Phe Leu Phe Pro Pro Lys Pro Lys Asp Thr Leu Met
                        260                 265                 270

Ile Ser Arg Thr Pro Glu Val Thr Cys Val Val Val Asp Val Ser His
                        275                 280                 285

Glu Asp Pro Glu Val Lys Phe Asn Trp Tyr Val Asp Gly Val Glu Val
                        290                 295                 300

His Asn Ala Lys Thr Lys Pro Arg Glu Glu Gln Tyr Asn Ser Thr Tyr
        305                 310                 315                 320

Arg Val Val Ser Val Leu Thr Val Leu His Gln Asp Trp Leu Asn Gly
                        325                 330                 335

Lys Glu Tyr Lys Cys Lys Val Ser Asn Lys Ala Leu Pro Ala Ser Ile
                        340                 345                 350

Glu Lys Thr Ile Ser Lys Ala Lys Gly Gln Pro Arg Glu Pro Gln Val
                        355                 360                 365

Tyr Thr Leu Pro Pro Ser Arg Glu Glu Met Thr Lys Asn Gln Val Ser
                        370                 375                 380

Leu Thr Cys Leu Val Lys Gly Phe Tyr Pro Ser Asp Ile Ala Val Glu
        385                 390                 395                 400

Trp Glu Ser Asn Gly Gln Pro Glu Asn Asn Tyr Lys Thr Thr Pro Pro
                        405                 410                 415

Val Leu Asp Ser Asp Gly Ser Phe Phe Leu Tyr Ser Lys Leu Thr Val
                        420                 425                 430

Asp Lys Ser Arg Trp Gln Gln Gly Asn Val Phe Ser Cys Ser Val Met
                        435                 440                 445

His Glu Ala Leu His Asn His Tyr Thr Gln Lys Ser Leu Ser Leu Ser
            450                 455                 460

Pro Gly Lys Leu
        465

<210> SEQ ID NO 68
<211> LENGTH: 699
<212> TYPE: DNA
<213> ORGANISM: UNKNOWN
<220> FEATURE:
<223> OTHER INFORMATION: GENOMIC

<400> SEQUENCE: 68
atggattttc aagtgcagat tttcagcttc ctgctaatca gtgcctcagt catactctcg      60
gacatcgagc tgacccagag cccggcgacc atgagcgcga gccgggtgaa cgtgttacc     120 ctgacctgca gcgcgagctc tagcatcagc tatatgttct ggtatcatca gcgtccgggt    180
cagagcccgc gtctgttgat ctatgatacc agcaacctgg cgagcggtgt tccggcgcgt    240
ttcagcggta gcggtagcgg taccagctat agcctgacca tcagccgtat ggaaccggaa    300
```

```
gatttcgcga cctatttctg ccatcagagc tctagctatc cgttcacctt cggtcagggt    360
accaaactcg agatcaaacg gactgtggct gcaccatctg tcttcatctt cccgccatct    420
gatgagcagt tgaaatctgg aactgcctct gttgtgtgcc tgctgaataa cttctatccc    480
agagaggcca agtacagtg gaaggtggat aacgccctcc aatcgggtaa ctcccaggag     540
agtgtcacag agcaggacag caaggacagc acctacagcc tcagcagcac cctgacgctg    600
agcaaagcag actacgagaa acacaaagtc tacgcctgcg aagtcaccca tcagggcctg    660
agctcgcccg tcacaaagag cttcaacagg ggagagtgc                            699
```

<210> SEQ ID NO 69
<211> LENGTH: 233
<212> TYPE: PRT
<213> ORGANISM: Artificial Sequence
<220> FEATURE:
<223> OTHER INFORMATION: SYNTHETIC

<400> SEQUENCE: 69

```
Met Asp Phe Gln Val Gln Ile Phe Ser Phe Leu Leu Ile Ser Ala Ser
1               5                   10                  15

Val Ile Leu Ser Asp Ile Glu Leu Thr Gln Ser Pro Ala Thr Met Ser
            20                  25                  30

Ala Ser Pro Gly Glu Arg Val Thr Leu Thr Cys Ser Ala Ser Ser Ser
        35                  40                  45

Ile Ser Tyr Met Phe Trp Tyr His Gln Arg Pro Gly Gln Ser Pro Arg
    50                  55                  60

Leu Leu Ile Tyr Asp Thr Ser Asn Leu Ala Ser Gly Val Pro Ala Arg
65                  70                  75                  80

Phe Ser Gly Ser Gly Ser Gly Thr Ser Tyr Ser Leu Thr Ile Ser Arg
                85                  90                  95

Met Glu Pro Glu Asp Phe Ala Thr Tyr Phe Cys His Gln Ser Ser Ser
            100                 105                 110

Tyr Pro Phe Thr Phe Gly Gln Gly Thr Lys Leu Glu Ile Lys Arg Thr
        115                 120                 125

Val Ala Ala Pro Ser Val Phe Ile Phe Pro Pro Ser Asp Glu Gln Leu
    130                 135                 140

Lys Ser Gly Thr Ala Ser Val Val Cys Leu Leu Asn Asn Phe Tyr Pro
145                 150                 155                 160

Arg Glu Ala Lys Val Gln Trp Lys Val Asp Asn Ala Leu Gln Ser Gly
                165                 170                 175

Asn Ser Gln Glu Ser Val Thr Glu Gln Asp Ser Lys Asp Ser Thr Tyr
            180                 185                 190

Ser Leu Ser Ser Thr Leu Thr Leu Ser Lys Ala Asp Tyr Glu Lys His
        195                 200                 205

Lys Val Tyr Ala Cys Glu Val Thr His Gln Gly Leu Ser Ser Pro Val
    210                 215                 220

Thr Lys Ser Phe Asn Arg Gly Glu Cys
225                 230
```

<210> SEQ ID NO 70
<211> LENGTH: 41
<212> TYPE: DNA
<213> ORGANISM: UNKNOWN
<220> FEATURE:
<223> OTHER INFORMATION: GENOMIC

<400> SEQUENCE: 70

```
cgcgctcgag atcaaacgga ccccgctggg tgataccact c              41

<210> SEQ ID NO 71
<211> LENGTH: 40
<212> TYPE: DNA
<213> ORGANISM: UNKNOWN
<220> FEATURE:
<223> OTHER INFORMATION: GENOMIC

<400> SEQUENCE: 71
cagttcacct ccggaggtat gagtggtatc acccagcggg                40

<210> SEQ ID NO 72
<211> LENGTH: 40
<212> TYPE: DNA
<213> ORGANISM: UNKNOWN
<220> FEATURE:
<223> OTHER INFORMATION: GENOMIC

<400> SEQUENCE: 72
atacctccgg aggtgaactg gaagagctgt tgaaacatct                40

<210> SEQ ID NO 73
<211> LENGTH: 40
<212> TYPE: DNA
<213> ORGANISM: UNKNOWN
<220> FEATURE:
<223> OTHER INFORMATION: GENOMIC

<400> SEQUENCE: 73
gacctttcag cagttctttc agatgtttca acagctcttc                40

<210> SEQ ID NO 74
<211> LENGTH: 40
<212> TYPE: DNA
<213> ORGANISM: UNKNOWN
<220> FEATURE:
<223> OTHER INFORMATION: GENOMIC

<400> SEQUENCE: 74
gaaagaactg ctgaaaggtc cgcggaaagg tgaactggag                40

<210> SEQ ID NO 75
<211> LENGTH: 40
<212> TYPE: DNA
<213> ORGANISM: UNKNOWN
<220> FEATURE:
<223> OTHER INFORMATION: GENOMIC

<400> SEQUENCE: 75
ttcaggtgct tcagcaattc ctccagttca cctttccgcg                40

<210> SEQ ID NO 76
<211> LENGTH: 40
<212> TYPE: DNA
<213> ORGANISM: UNKNOWN
<220> FEATURE:
<223> OTHER INFORMATION: GENOMIC

<400> SEQUENCE: 76
gaattgctga agcacctgaa agagctgttg aaaggtaccc                40

<210> SEQ ID NO 77
<211> LENGTH: 40
<212> TYPE: DNA
<213> ORGANISM: UNKNOWN
```

```
<220> FEATURE:
<223> OTHER INFORMATION: GENOMIC

<400> SEQUENCE: 77
atgggtagta tcacctaggg gggtaccttt caacagctct                              40

<210> SEQ ID NO 78
<211> LENGTH: 40
<212> TYPE: DNA
<213> ORGANISM: UNKNOWN
<220> FEATURE:
<223> OTHER INFORMATION: GENOMIC

<400> SEQUENCE: 78
ccctaggtga tactacccat accagcggtc aggtgcaact                              40

<210> SEQ ID NO 79
<211> LENGTH: 42
<212> TYPE: DNA
<213> ORGANISM: UNKNOWN
<220> FEATURE:
<223> OTHER INFORMATION: GENOMIC

<400> SEQUENCE: 79
cgcggaattc gcgttcgcga ctagttgcac ctgaccgctg gt                           42

<210> SEQ ID NO 80
<211> LENGTH: 21
<212> TYPE: DNA
<213> ORGANISM: UNKNOWN
<220> FEATURE:
<223> OTHER INFORMATION: GENOMIC

<400> SEQUENCE: 80
cgcggtatac tgacccagag c                                                  21

<210> SEQ ID NO 81
<211> LENGTH: 22
<212> TYPE: DNA
<213> ORGANISM: UNKNOWN
<220> FEATURE:
<223> OTHER INFORMATION: GENOMIC

<400> SEQUENCE: 81
cgcgctcgag tttggtaccc tg                                                 22

<210> SEQ ID NO 82
<211> LENGTH: 29
<212> TYPE: DNA
<213> ORGANISM: UNKNOWN
<220> FEATURE:
<223> OTHER INFORMATION: GENOMIC

<400> SEQUENCE: 82
cgcgactagt gcagagcggt agcgaactg                                          29

<210> SEQ ID NO 83
<211> LENGTH: 26
<212> TYPE: DNA
<213> ORGANISM: UNKNOWN
<220> FEATURE:
<223> OTHER INFORMATION: GENOMIC

<400> SEQUENCE: 83
gccagtgaat tctattagtg gtgatg                                             26
```

```
<210> SEQ ID NO 84
<211> LENGTH: 1626
<212> TYPE: DNA
<213> ORGANISM: UNKNOWN
<220> FEATURE:
<223> OTHER INFORMATION: GENOMIC

<400> SEQUENCE: 84
caggtgcagc tggtgcagag cggtagcgaa ctgaaaaaac cgggtgcgag cgttaagatc      60
agctgcaaag cgagcggtta taccttcacc gattacggta tgaactgggt taaacaggcg     120
ccgggtcaag gtctgaaatg gatgggttgg atcaacacct acaccggtga agcacctac      180
gttgacgatt tcaaaggtcg tttcgttttc agcctggata ccagcgttag cgcggcctac    240
ctgcagatca gctctctgaa agcggaagac accgcgacct acttctgcgc gcgtcgcggt    300
ttctacgcga tggattactg gggccaaggg accacggtca ccgtctcctc aggtggaggc    360
ggttcaggcg gaggtggctc tggcggtggc ggatcggaca tcgtactgac ccagagcccg    420
gcgaccatga gcgcgagccc gggtgaacgt gttaccctga cctgcagcgc gagctctagc    480
atcagctata tgttctggta tcatcagcgt ccgggtcaga gcccgcgtct gttgatctat    540
gataccagca acctgcgag cggtgttccg gcgcgtttca gcggtagcgg tagcggtacc      600
agctatagcc tgaccatcag ccgtatggaa ccggaagatt tcgcgaccta tttctgccat    660
cagagctcta gctatccgtt caccttcggt cagggtacca aactcgagat caaacggacc    720
ccgctgggtg ataccactca tacctccgga ggtgaactgg aagagctgtt gaaacatctg    780
aaagaactgc tgaaaggtcc gcggaaaggt gaactggagg aattgctgaa gcacctgaaa    840
gagctgttga aggtaccccc cctgggtgat actacccata ccagcggtca ggtgcaacta    900
gtgcagagcg gtagcgaact gaaaaaaccg ggtgcgagcg ttaagatcag ctgcaaagcg    960
agcggttata ccttcaccga ttacggtatg aactgggtta acaggcgcc gggtcaaggt    1020
ctgaaatgga tgggttggat caacacctac accggtgaaa gcacctacgt tgacgatttc    1080
aaaggtcgtt tcgttttcag cctggatacc agcgttagcg cggcctacct gcagatcagc    1140
tctctgaaag cggaagacac cgcgacctac ttctgcgcgc gtcgcggttt ctacgcgatg    1200
gattactggg gccaagggac cacggtcacc gtctcctcag gtggaggcgg ttcaggcgga    1260
ggtggctctg gcggtggcgg atcggacatc gtactgaccc agagcccggc gaccatgagc    1320
gcgagcccgg gtgaacgtgt taccctgacc tgcagcgcga gctctagcat cagctatatg    1380
ttctggtatc atcagcgtcc gggtcagagc ccgcgtctgt tgatctatga taccagcaac    1440
ctggcgagcg gtgttccggc gcgtttcagc ggtagcggta gcggtaccag ctatagcctg    1500
accatcagcc gtatggaacc ggaagatttc gcgacctatt tctgccatca gagctctagc    1560
tatccgttca ccttcggtca gggtaccaaa ctcgagatca acggcacca tcaccatcac    1620
cactaa                                                              1626

<210> SEQ ID NO 85
<211> LENGTH: 541
<212> TYPE: PRT
<213> ORGANISM: Artificial Sequence
<220> FEATURE:
<223> OTHER INFORMATION: SYNTHETIC

<400> SEQUENCE: 85

Gln Val Gln Leu Val Gln Ser Gly Ser Glu Leu Lys Lys Pro Gly Ala
 1               5                  10                  15
```

-continued

```
Ser Val Lys Ile Ser Cys Lys Ala Ser Gly Tyr Thr Phe Thr Asp Tyr
             20                  25                  30

Gly Met Asn Trp Val Lys Gln Ala Pro Gly Gln Gly Leu Lys Trp Met
             35                  40                  45

Gly Trp Ile Asn Thr Tyr Thr Gly Glu Ser Thr Tyr Val Asp Asp Phe
 50                  55                  60

Lys Gly Arg Phe Val Phe Ser Leu Asp Thr Ser Val Ser Ala Ala Tyr
 65                  70                  75                  80

Leu Gln Ile Ser Ser Leu Lys Ala Glu Asp Thr Ala Thr Tyr Phe Cys
                 85                  90                  95

Ala Arg Arg Gly Phe Tyr Ala Met Asp Tyr Trp Gly Gln Gly Thr Thr
                100                 105                 110

Val Thr Val Ser Ser Gly Gly Gly Gly Ser Gly Gly Gly Gly Ser Gly
             115                 120                 125

Gly Gly Gly Ser Asp Ile Val Leu Thr Gln Ser Pro Ala Thr Met Ser
 130                 135                 140

Ala Ser Pro Gly Glu Arg Val Thr Leu Thr Cys Ser Ala Ser Ser Ser
 145                 150                 155                 160

Ile Ser Tyr Met Phe Trp Tyr His Gln Arg Pro Gly Gln Ser Pro Arg
                 165                 170                 175

Leu Leu Ile Tyr Asp Thr Ser Asn Leu Ala Ser Gly Val Pro Ala Arg
                 180                 185                 190

Phe Ser Gly Ser Gly Ser Gly Thr Ser Tyr Ser Leu Thr Ile Ser Arg
             195                 200                 205

Met Glu Pro Glu Asp Phe Ala Thr Tyr Phe Cys His Gln Ser Ser Ser
 210                 215                 220

Tyr Pro Phe Thr Phe Gly Gln Gly Thr Lys Leu Glu Ile Lys Arg Thr
225                 230                 235                 240

Pro Leu Gly Asp Thr Thr His Thr Ser Gly Gly Glu Leu Glu Glu Leu
                 245                 250                 255

Leu Lys His Leu Lys Glu Leu Leu Lys Gly Pro Arg Lys Gly Glu Leu
                 260                 265                 270

Glu Glu Leu Leu Lys His Leu Lys Glu Leu Leu Lys Gly Thr Pro Leu
             275                 280                 285

Gly Asp Thr Thr His Thr Ser Gly Gln Val Gln Leu Val Gln Ser Gly
 290                 295                 300

Ser Glu Leu Lys Lys Pro Gly Ala Ser Val Lys Ile Ser Cys Lys Ala
305                 310                 315                 320

Ser Gly Tyr Thr Phe Thr Asp Tyr Gly Met Asn Trp Val Lys Gln Ala
                 325                 330                 335

Pro Gly Gln Gly Leu Lys Trp Met Gly Trp Ile Asn Thr Tyr Thr Gly
                 340                 345                 350

Glu Ser Thr Tyr Val Asp Asp Phe Lys Gly Arg Phe Val Phe Ser Leu
             355                 360                 365

Asp Thr Ser Val Ser Ala Ala Tyr Leu Gln Ile Ser Ser Leu Lys Ala
 370                 375                 380

Glu Asp Thr Ala Thr Tyr Phe Cys Ala Arg Arg Gly Phe Tyr Ala Met
385                 390                 395                 400

Asp Tyr Trp Gly Gln Gly Thr Thr Val Thr Val Ser Ser Gly Gly Gly
                 405                 410                 415

Gly Ser Gly Gly Gly Gly Ser Gly Gly Gly Gly Ser Asp Ile Val Leu
             420                 425                 430

Thr Gln Ser Pro Ala Thr Met Ser Ala Ser Pro Gly Glu Arg Val Thr
```

```
                435              440                 445
Leu Thr Cys Ser Ala Ser Ser Ile Ser Tyr Met Phe Trp Tyr His
        450                 455             460

Gln Arg Pro Gly Gln Ser Pro Arg Leu Leu Ile Tyr Asp Thr Ser Asn
465             470                 475                 480

Leu Ala Ser Gly Val Pro Ala Arg Phe Ser Gly Ser Gly Ser Gly Thr
                485                 490                 495

Ser Tyr Ser Leu Thr Ile Ser Arg Met Glu Pro Glu Asp Phe Ala Thr
            500                 505                 510

Tyr Phe Cys His Gln Ser Ser Tyr Pro Phe Thr Phe Gly Gln Gly
            515                 520             525

Thr Lys Leu Glu Ile Lys Arg His His His His His
        530                 535             540

<210> SEQ ID NO 86
<211> LENGTH: 3423
<212> TYPE: DNA
<213> ORGANISM: UNKNOWN
<220> FEATURE:
<223> OTHER INFORMATION: GENOMIC

<400> SEQUENCE: 86
ttccggggat ctctcaccta ccaaacaatg ccccccctgca aaaataaat tcatataaaa      60 aacatacaga taaccatctg cggtgataaa ttatctctgg cggtgttgac ataaatacca    120
ctggcggtga tactgagcac atcagcagga cgcactgacc accatgaagg tgacgctctt    180
aaaaattaag ccctgaagaa gggcagggggt accaggaggt ttaaatcatg gtaagatcaa    240
gtagtcaaaa ttcgagtgac aagcctgtag cccacgtcgt agcaaccac caagtggagg    300 agcagtaacc atggttactg gagaagggggg accaactcag cgctgaggtc aatctgccca    360
agtctagagt cgacctgcag cccaagcttg gctgttttgg cggatgagag aagattttca    420
gcctgataca gattaaatca gaacgcagaa gcggtctgat aaaacagaat ttgcctggcg    480
gcagtagcgc ggtggtccca cctgaccca tgccgaactc agaagtgaaa cgccgtagcg    540
ccgatggtag tgtggggtct ccccatgcga gagtagggaa ctgccaggca tcaaataaaa    600
cgaaaggctc agtcgaaaga ctgggccttt cgttttatct gttgttttgtc ggtgaacgct    660 ctcctgagta ggacaaatcc gccgggagcg gatttgaacg ttgcgaagca acggcccgga    720
gggtggcggg caggacgccc gccataaact gccaggcatc aaattaagca gaaggccatc    780
ctgacggatg gccttttgc gtttctacaa actcttttgt ttattttttct aaatacattc    840 aaatatgtat ccgctcatga gacaataacc ctgataaatg cttcaataat aaaaggatct    900
aggtgaagat ccttttttgat aatctcatga ccaaaatccc ttaacgtgag ttttcgttcc    960
actgagcgtc agacccgta gaaaagatca aggatcttc ttgagatcct tttttttctgc   1020 gcgtaatctg ctgcttgcaa acaaaaaaac caccgctacc agcggtggtt tgtttgccgg   1080
atcaagagct accaactctt tttccgaagg taactggctt cagcagagcg cagataccaa   1140
atactgtcct tctagtgtag ccgtagttag gccaccactt caagaactct gtagcaccgc   1200
ctacataccc cgctctgcta atcctgttac cagtggctgc tgccagtggc gataagtcgt   1260
gtcttaccgg gttggactca agacgatagt taccggataa ggcgcagcgg tcgggctgaa   1320
cggggggttc gtgcacacag cccagcttgg agcgaacgac ctacaccgaa ctgagatacc   1380
tacagcgtga gcattgagaa agcgccacgc ttcccgaagg gagaaaggcg gacaggtatc   1440
cggtaagcgg cagggtcgga acaggagagc gcacgaggga gcttccaggg ggaaacgcct   1500
```

-continued

```
ggtatcttta tagtcctgtc gggtttcgcc acctctgact tgagcgtcga tttttgtgat      1560
gctcgtcagg ggggcggagc ctatggaaaa acgccagcaa cgcggccttt ttacggttcc      1620
tggccttttg ctggcctttt gctcacatgt tctttcctgc gttatcccct gattctgtgg      1680
ataaccgtat taccgccttt gagtgagctg ataccgctcg ccgcagccga acgaccgagc      1740
gcagcgagtc agtgagcgag gaagcggaag agcgctgact tccgcgtttc cagactttac      1800
gaaacacgga aaccgaagac cattcatgtt gttgctcagg tcgcagacgt tttgcagcag      1860
cagtcgcttc acgttcgctc gcgtatcggt gattcattct gctaaccagt aaggcaaccc      1920
cgccagccta gccgggtcct caacgacagg agcacgatca tgcgcacccg tggccaggac      1980
ccaacgctgc ccgagatgcg ccgcgtgcgg ctgctggaga tggcggacgc gatggatatg      2040
ttctgccaag ggttggtttg cgcattcaca gttctccgca agaattgatt ggctccaatt      2100
cttggagtgg tgaatccgtt agcgaggtgc cgccggcttc cattcaggtc gaggtggccc      2160
ggctccatgc accgcgacgc aacgcgggga ggcagacaag gtatagggcg cgcctacaa      2220 tccatgccaa cccgttccat gtgctcgccc aggcggcata aatcgccgtg acgatcagcg      2280
gtccagtgat cgaagttagg ctggtaagag ccgcgagcga tccttgaagc tgtccctgat      2340
ggtcgtcatc tacctgcctg gacagcatgg cctgcaacgc gggcatcccg atgccgccgg      2400
aagcgagaag aatcataatg gggaaggcca tccagcctcg cgtcgcgaac gccagcaaga      2460
cgtagcccag cgcgtcggcc gccatgccgg cgataatggc ctgcttctcg ccgaaacgtt      2520
tggtggcggg accagtgacg aaggcttgag cgagggcgtg caagattccg aataccgcaa      2580
gcgacaggcc gatcatcgtc gcgctccagc gaaagcggtc ctcgccgaaa atgacccaga      2640
gcgctgccgg cacctgtcct acgagttgca tgataaagaa gacagtcata agtgcggcga      2700
cgatagtcat gccccgcgcc caccggaagg agctgactgg gttgaaggct ctcaagggca      2760
tcggtcggcg ctctccctta tgcgactcct gcattaggaa gcagcccagt agtaggttga      2820
ggccgttgag caccgccgcc gcaaggaatg gtgcatgtaa ggagatggcg cccaacagtc      2880
ccccggccac ggggcctgcc accatacccca cgccgaaaca agcgctcatg agcccgaagt      2940
ggcgagcccg atcttcccca tcggtgatgt cggcgatata ggcgccagca accgcacctg      3000
tggcgccggt gatgccggcc acgatgcgtc cggcgtagag aatccacagg acgggtgtgg      3060
tcgccatgat cgcgtagtcg atagtggctc caagtagcga agcgagcagg actgggcggc      3120
ggccaaagcg gtcggacagt gctccgagaa cgggtgcgca tagaaattgc atcaacgcat      3180
atagcgctag cagcacgcca tagtgactgg cgatgctgtc ggaatggacg atatcccgca      3240
agaggcccgg cagtaccggc ataaccaagc ctatgcctac agcatccagg gtgacggtgc      3300
cgaggatgac gatgagcgca ttgttagatt tcatacacgg tgcctgactg cgttagcaat      3360
ttaactgtga taaactaccg cattaaagct aatcgatgat aagctgtcaa acatgagaat      3420
taa                                                                    3423
```

<210> SEQ ID NO 87
<211> LENGTH: 41
<212> TYPE: DNA
<213> ORGANISM: UNKNOWN
<220> FEATURE:
<223> OTHER INFORMATION: GENOMIC

<400> SEQUENCE: 87

```
cccaagcttg gcggaggctc acaggtgcag ctggtgcaga g                          41
```

<210> SEQ ID NO 88
<211> LENGTH: 30
<212> TYPE: DNA
<213> ORGANISM: UNKNOWN
<220> FEATURE:
<223> OTHER INFORMATION: GENOMIC

<400> SEQUENCE: 88
cggaattcta ccgtttgatc tcgagtttgg                                       30

<210> SEQ ID NO 89
<211> LENGTH: 2133
<212> TYPE: DNA
<213> ORGANISM: UNKNOWN
<220> FEATURE:
<223> OTHER INFORMATION: GENOMIC

<400> SEQUENCE: 89

| | |
|---|---|
| atggattttc aagtgcagat tttcagcttc ctgctaatca gtgcctcagt catactctcg | 60 |
| caggtgcagc tggtgcagag cggtagcgaa ctgaaaaaac cgggtgcgag cgttaagatc | 120 |
| agctgcaaag cgagcggtta taccttcacc gattacggta tgaactgggt taaacaggcg | 180 |
| ccgggtcaag gtctgaaatg gatgggttgg atcaacacct acaccggtga agcacctac | 240 |
| gttgacgatt tcaaaggtcg tttcgttttc agcctggata ccagcgttag cgcggcctac | 300 |
| ctgcagatca gctctctgaa agcggaagac accgcgacct acttctgcgc gcgtcgcggt | 360 |
| ttctacgcga tggattactg gggccaaggg accacgtca ccgtctcgag cgcatccacc | 420 |
| aagggcccat cggtcttccc cctggcaccc tcctccaaga gcacctctgg ggcacagcg | 480 |
| gccctgggct gcctggtcaa ggactacttc cccgaaccgg tgacggtgtc gtggaactca | 540 |
| ggcgccctga ccagcggcgt gcacaccttc ccggctgtcc tacagtcctc aggactctac | 600 |
| tccctcagca gcgtggtgac cgtgccctcc agcagcttgg gcacccagac ctacatctgc | 660 |
| aacgtgaatc acaagcccag caacaccaag gtggacaaga gagttgagcc caaatcttgt | 720 |
| gacaaaactc acacatgccc accgtgccca gcacctgaac tcctgggggg accgtcagtc | 780 |
| ttcctcttcc ccccaaaacc caaggacacc ctcatgatct cccggacccc tgaggtcaca | 840 |
| tgcgtggtgg tggacgtgag ccacgaagac cctgaggtca agttcaactg gtacgtggac | 900 |
| ggcgtggagg tgcataatgc caagacaaag ccgcgggagg agcagtacaa cagcacgtac | 960 |
| cgtgtggtca gcgtcctcac cgtcctgcac caggactggc tgaatggcaa ggagtacaag | 1020 |
| tgcaaggtct ccaacaaagc cctcccagcc tccatcgaga aaccatctc caaagccaaa | 1080 |
| gggcagcccc gagaaccaca ggtgtacacc ctgcccccat cccgggagga gatgaccaag | 1140 |
| aaccaggtca gcctgacctg cctggtcaaa ggcttctatc ccagcgacat cgccgtggag | 1200 |
| tgggagagca atgggcagcc ggagaacaac tacaagacca cgcctcccgt gctggactcc | 1260 |
| gacggctcct tcttcctcta tagcaagctc accgtggaca agagcaggtg gcagcagggg | 1320 |
| aacgtcttct catgctccgt gatgcatgag gctctgcaca accactacac gcagaagagc | 1380 |
| ctctccctgt ctccgggtaa gcttggcgga ggctcacagg tgcagctggt gcagagcggt | 1440 |
| agcgaactga aaaaccggg tgcgagcgtt aagatcagct gcaaagcgag cggttatacc | 1500 |
| ttcaccgatt acggtatgaa ctgggttaaa caggcgccgg gtcaaggtct gaaatggatg | 1560 |
| ggttggatca acacctacac cggtgaaagc acctacgttg acgatttcaa aggtcgtttc | 1620 |
| gttttcagcc tggataccag cgttagcgcg gcctacctgc agatcagctc tctgaaagcg | 1680 |
| gaagacaccg cgacctactt ctgcgcgcgt cgcggtttct acgcgatgga ttactggggc | 1740 |

```
caagggacca cggtcaccgt ctcctcaggt ggaggcggtt caggcggagg tggctctggc   1800
ggtggcggat cggacatcgt actgacccag agcccggcga ccatgagcgc gagcccgggt   1860
gaacgtgtta ccctgacctg cagcgcgagc tctagcatca gctatatgtt ctggtatcat   1920
cagcgtccgg gtcagagccc gcgtctgttg atctatgata ccagcaacct ggcgagcggt   1980
gttccggcgc gtttcagcgg tagcggtagc ggtaccagct atagcctgac catcagccgt   2040
atggaaccgg aagatttcgc gacctatttc tgccatcaga gctctagcta tccgttcacc   2100
ttcggtcagg gtaccaaact cgagatcaaa cgg                                2133
```

<210> SEQ ID NO 90
<211> LENGTH: 711
<212> TYPE: PRT
<213> ORGANISM: Artificial Sequence
<220> FEATURE:
<223> OTHER INFORMATION: SYNTHETIC

<400> SEQUENCE: 90

```
Met Asp Phe Gln Val Gln Ile Phe Ser Phe Leu Leu Ile Ser Ala Ser
1               5                   10                  15

Val Ile Leu Ser Gln Val Gln Leu Val Gln Ser Gly Ser Glu Leu Lys
            20                  25                  30

Lys Pro Gly Ala Ser Val Lys Ile Ser Cys Lys Ala Ser Gly Tyr Thr
        35                  40                  45

Phe Thr Asp Tyr Gly Met Asn Trp Val Lys Gln Ala Pro Gly Gln Gly
    50                  55                  60

Leu Lys Trp Met Gly Trp Ile Asn Thr Tyr Thr Gly Glu Ser Thr Tyr
65                  70                  75                  80

Val Asp Asp Phe Lys Gly Arg Phe Val Phe Ser Leu Asp Thr Ser Val
                85                  90                  95

Ser Ala Ala Tyr Leu Gln Ile Ser Ser Leu Lys Ala Glu Asp Thr Ala
            100                 105                 110

Thr Tyr Phe Cys Ala Arg Arg Gly Phe Tyr Ala Met Asp Tyr Trp Gly
        115                 120                 125

Gln Gly Thr Thr Val Thr Val Ser Ser Ala Ser Thr Lys Gly Pro Ser
    130                 135                 140

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Leu Gly Thr Gln Thr Tyr Ile Cys Asn Val Asn His
    210                 215                 220

Lys Pro Ser Asn Thr Lys Val Asp Lys Arg Val Glu Pro Lys Ser Cys
225                 230                 235                 240

Asp Lys Thr His Thr Cys Pro Pro Cys Pro Ala Pro Glu Leu Leu Gly
                245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser His
        275                 280                 285
```

-continued

```
Glu Asp Pro Glu Val Lys Phe Asn Trp Tyr Val Asp Gly Val Glu Val
    290                 295                 300

His Asn Ala Lys Thr Lys Pro Arg Glu Glu Gln Tyr Asn Ser Thr Tyr
305                 310                 315                 320

Arg Val Val Ser Val Leu Thr Val Leu His Gln Asp Trp Leu Asn Gly
                325                 330                 335

Lys Glu Tyr Lys Cys Lys Val Ser Asn Lys Ala Leu Pro Ala Ser Ile
            340                 345                 350

Glu Lys Thr Ile Ser Lys Ala Lys Gly Gln Pro Arg Glu Pro Gln Val
        355                 360                 365

Tyr Thr Leu Pro Pro Ser Arg Glu Glu Met Thr Lys Asn Gln Val Ser
    370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Val Leu Asp Ser Asp Gly Ser Phe Phe Leu Tyr Ser Lys Leu Thr Val
            420                 425                 430

Asp Lys Ser Arg Trp Gln Gln Gly Asn Val Phe Ser Cys Ser Val Met
        435                 440                 445

His Glu Ala Leu His Asn His Tyr Thr Gln Lys Ser Leu Ser Leu Ser
    450                 455                 460

Pro Gly Lys Leu Gly Gly Ser Gln Val Gln Leu Val Gln Ser Gly
465                 470                 475                 480

Ser Glu Leu Lys Lys Pro Gly Ala Ser Val Lys Ile Ser Cys Lys Ala
                485                 490                 495

Ser Gly Tyr Thr Phe Thr Asp Tyr Gly Met Asn Trp Val Lys Gln Ala
            500                 505                 510

Pro Gly Gln Gly Leu Lys Trp Met Gly Trp Ile Asn Thr Tyr Thr Gly
        515                 520                 525

Glu Ser Thr Tyr Val Asp Asp Phe Lys Gly Arg Phe Val Phe Ser Leu
    530                 535                 540

Asp Thr Ser Val Ser Ala Ala Tyr Leu Gln Ile Ser Ser Leu Lys Ala
545                 550                 555                 560

Glu Asp Thr Ala Thr Tyr Phe Cys Ala Arg Arg Gly Phe Tyr Ala Met
                565                 570                 575

Asp Tyr Trp Gly Gln Gly Thr Thr Val Thr Val Ser Ser Gly Gly Gly
            580                 585                 590

Gly Ser Gly Gly Gly Gly Ser Gly Gly Gly Gly Ser Asp Ile Val Leu
        595                 600                 605

Thr Gln Ser Pro Ala Thr Met Ser Ala Ser Pro Gly Glu Arg Val Thr
    610                 615                 620

Leu Thr Cys Ser Ala Ser Ser Ser Ile Ser Tyr Met Phe Trp Tyr His
625                 630                 635                 640

Gln Arg Pro Gly Gln Ser Pro Arg Leu Leu Ile Tyr Asp Thr Ser Asn
                645                 650                 655

Leu Ala Ser Gly Val Pro Ala Arg Phe Ser Gly Ser Gly Ser Gly Thr
            660                 665                 670

Ser Tyr Ser Leu Thr Ile Ser Arg Met Glu Pro Glu Asp Phe Ala Thr
        675                 680                 685

Tyr Phe Cys His Gln Ser Ser Ser Tyr Pro Phe Thr Phe Gly Gln Gly
    690                 695                 700

Thr Lys Leu Glu Ile Lys Arg
```

<210> SEQ ID NO 91
<211> LENGTH: 240
<212> TYPE: PRT
<213> ORGANISM: Artificial Sequence
<220> FEATURE:
<223> OTHER INFORMATION: SYNTHETIC

<400> SEQUENCE: 91

```
Gln Val Gln Leu Val Gln Ser Gly Ser Glu Leu Lys Lys Pro Gly Ala
1               5                   10                  15

Ser Val Lys Ile Ser Cys Lys Ala Ser Gly Tyr Thr Phe Thr Asp Tyr
            20                  25                  30

Gly Met Asn Trp Val Lys Gln Ala Pro Gly Gln Gly Leu Lys Trp Met
        35                  40                  45

Gly Trp Ile Asn Thr Tyr Thr Gly Glu Ser Thr Tyr Val Asp Asp Phe
    50                  55                  60

Lys Gly Arg Phe Val Phe Ser Leu Asp Thr Ser Val Ser Ala Ala Tyr
65                  70                  75                  80

Leu Gln Ile Ser Ser Leu Lys Ala Glu Asp Thr Ala Thr Tyr Phe Cys
                85                  90                  95

Ala Arg Arg Gly Phe Tyr Ala Met Asp Tyr Trp Gly Gln Gly Thr Thr
            100                 105                 110

Val Thr Val Ser Ser Gly Gly Gly Ser Gly Gly Gly Gly Ser Asp
        115                 120                 125

Ile Val Leu Thr Gln Ser Pro Ala Thr Met Ser Ala Ser Pro Gly Glu
    130                 135                 140

Arg Val Thr Leu Thr Cys Ser Ala Ser Ser Ser Ile Ser Tyr Met Phe
145                 150                 155                 160

Trp Tyr His Gln Arg Pro Gly Gln Ser Pro Arg Leu Leu Ile Tyr Asp
                165                 170                 175

Thr Ser Asn Leu Ala Ser Gly Val Pro Ala Arg Phe Ser Gly Ser Gly
            180                 185                 190

Ser Gly Thr Ser Tyr Ser Leu Thr Ile Ser Arg Met Glu Pro Glu Asp
        195                 200                 205

Phe Ala Thr Tyr Phe Cys His Gln Ser Ser Ser Tyr Pro Phe Thr Phe
    210                 215                 220

Gly Gln Gly Thr Lys Leu Glu Ile Lys Arg His His His His His
225                 230                 235                 240
```

<210> SEQ ID NO 92
<211> LENGTH: 702
<212> TYPE: DNA
<213> ORGANISM: UNKNOWN
<220> FEATURE:
<223> OTHER INFORMATION: GENOMIC

<400> SEQUENCE: 92

```
caggtgcagc tggtgcagag cggtagcgaa ctgaaaaaac cgggtgcgag cgttaagatc      60
agctgcaaag cgagcggtta taccttcacc gattacggta tgaactgggt taaacaggcg     120
ccgggtcaag gtctgaaatg gatgggttgg atcaacacct acaccggtga agcacctac      180 gttgacgatt tcaaaggtcg tttcgttttc agcctggata ccagcgttag cgcggcctac     240
ctgcagatca gctctctgaa agcggaagac accgcgacct acttctgcgc gcgtcgcggt     300
ttctacgcga tggattactg gggccaaggg accacggtca ccgtctcctc aggcggaggt     360
```

```
ggctctggcg gtggcggatc ggacatcgta ctgacccaga gcccggcgac catgagcgcg    420
agcccgggtg aacgtgttac cctgacctgc agcgcgagct ctagcatcag ctatatgttc    480
tggtatcatc agcgtccggg tcagagcccg cgtctgttga tctatgatac cagcaacctg    540
gcgagcggtg ttccggcgcg tttcagcggt agcggtagcg gtaccagcta tagcctgacc    600
atcagccgta tggaaccgga agatttcgcg acctatttct gccatcagag ctctagctat    660
ccgttcacct tcggtcaggg taccaaactc gagatcaaac gg                       702
```

<210> SEQ ID NO 93
<211> LENGTH: 235
<212> TYPE: PRT
<213> ORGANISM: Artificial Sequence
<220> FEATURE:
<223> OTHER INFORMATION: SYNTHETIC

<400> SEQUENCE: 93

```
Gln Val Gln Leu Val Gln Ser Gly Ser Glu Leu Lys Lys Pro Gly Ala
1               5                   10                  15

Ser Val Lys Ile Ser Cys Lys Ala Ser Gly Tyr Thr Phe Thr Asp Tyr
            20                  25                  30

Gly Met Asn Trp Val Lys Gln Ala Pro Gly Gln Gly Leu Lys Trp Met
        35                  40                  45

Gly Trp Ile Asn Thr Tyr Thr Gly Glu Ser Thr Tyr Val Asp Asp Phe
    50                  55                  60

Lys Gly Arg Phe Val Phe Ser Leu Asp Thr Ser Val Ser Ala Ala Tyr
65                  70                  75                  80

Leu Gln Ile Ser Ser Leu Lys Ala Glu Asp Thr Ala Thr Tyr Phe Cys
                85                  90                  95

Ala Arg Arg Gly Phe Tyr Ala Met Asp Tyr Trp Gly Gln Gly Thr Thr
            100                 105                 110

Val Thr Val Ser Ser Gly Gly Gly Ser Asp Ile Val Leu Thr Gln
            115                 120                 125

Ser Pro Ala Thr Met Ser Ala Ser Pro Gly Glu Arg Val Thr Leu Thr
    130                 135                 140

Cys Ser Ala Ser Ser Ile Ser Tyr Met Phe Trp Tyr His Gln Arg
145                 150                 155                 160

Pro Gly Gln Ser Pro Arg Leu Leu Ile Tyr Asp Thr Ser Asn Leu Ala
                165                 170                 175

Ser Gly Val Pro Ala Arg Phe Gly Ser Gly Ser Gly Thr Ser Tyr
            180                 185                 190

Ser Leu Thr Ile Ser Arg Met Glu Pro Glu Asp Phe Ala Thr Tyr Phe
        195                 200                 205

Cys His Gln Ser Ser Ser Tyr Pro Phe Thr Phe Gly Gln Gly Thr Lys
    210                 215                 220

Leu Glu Ile Lys Arg His His His His His
225                 230                 235
```

<210> SEQ ID NO 94
<211> LENGTH: 687
<212> TYPE: DNA
<213> ORGANISM: UNKNOWN
<220> FEATURE:
<223> OTHER INFORMATION: GENOMIC

<400> SEQUENCE: 94

```
caggtgcagc tggtgcagag cggtagcgaa ctgaaaaaac cgggtgcgag cgttaagatc    60
```

-continued

```
agctgcaaag cgagcggtta taccttcacc gattacggta tgaactgggt taaacaggcg      120
ccgggtcaag gtctgaaatg gatgggttgg atcaacacct acaccggtga agcacctac       180 gttgacgatt tcaaaggtcg tttcgttttc agcctggata ccagcgttag cgcggcctac      240
ctgcagatca gctctctgaa agcggaagac accgcgacct acttctgcgc gcgtcgcggt      300
ttctacgcga tggattactg gggccaaggg accacggtca ccgtctcctc aggcggtggc      360
ggatcggaca tcgtactgac ccagagcccg gcgaccatga gcgcgagccc gggtgaacgt      420
gttaccctga cctgcagcgc gagctctagc atcagctata tgttctggta tcatcagcgt      480
ccgggtcaga gcccgcgtct gttgatctat gataccagca acctggcgag cggtgttccg      540
gcgcgtttca gcgtagcgg tagcggtacc agctatagcc tgaccatcag ccgtatggaa       600
ccggaagatt tcgcgaccta tttctgccat cagagctcta gctatccgtt caccttcggt      660
cagggtacca aactcgagat caaacgg                                         687
```

<210> SEQ ID NO 95
<211> LENGTH: 34
<212> TYPE: DNA
<213> ORGANISM: UNKNOWN
<220> FEATURE:
<223> OTHER INFORMATION: GENOMIC

<400> SEQUENCE: 95

```
ggccgctctt cgaaatacct attgcctacg gcag                                  34
```

<210> SEQ ID NO 96
<211> LENGTH: 70
<212> TYPE: DNA
<213> ORGANISM: UNKNOWN
<220> FEATURE:
<223> OTHER INFORMATION: GENOMIC

<400> SEQUENCE: 96

```
ctgggtcagt acgatgtcag agccacctcc gcctgaaccg cctccacctg aggagacggt      60
gaccgtggtc                                                            70
```

<210> SEQ ID NO 97
<211> LENGTH: 67
<212> TYPE: DNA
<213> ORGANISM: UNKNOWN
<220> FEATURE:
<223> OTHER INFORMATION: GENOMIC

<400> SEQUENCE: 97

```
gtcaccgtct cctcaggtgg aggcggttca ggcggaggtg gctctgacat cgtactgacc      60
cagagcc                                                               67
```

<210> SEQ ID NO 98
<211> LENGTH: 26
<212> TYPE: DNA
<213> ORGANISM: UNKNOWN
<220> FEATURE:
<223> OTHER INFORMATION: GENOMIC

<400> SEQUENCE: 98

```
gccagtgaat tctattagtg gtgatg                                          26
```

<210> SEQ ID NO 99
<211> LENGTH: 55
<212> TYPE: DNA
<213> ORGANISM: UNKNOWN

-continued

<220> FEATURE:
<223> OTHER INFORMATION: GENOMIC

<400> SEQUENCE: 99

```
ctgggtcagt acgatgtctg aaccgcctcc acctgaggag acggtgaccg tggtc          55
```

<210> SEQ ID NO 100
<211> LENGTH: 52
<212> TYPE: DNA
<213> ORGANISM: UNKNOWN
<220> FEATURE:
<223> OTHER INFORMATION: GENOMIC

<400> SEQUENCE: 100

```
gtcaccgtct cctcaggtgg aggcggttca gacatcgtac tgacccagag cc             52
```

<210> SEQ ID NO 101
<211> LENGTH: 672
<212> TYPE: DNA
<213> ORGANISM: UNKNOWN
<220> FEATURE:
<223> OTHER INFORMATION: GENOMIC

<400> SEQUENCE: 101

```
caggtgcagc tggtgcagag cggtagcgaa ctgaaaaaac cgggtgcgag cgttaagatc     60
agctgcaaag cgagcggtta taccttcacc gattacggta tgaactgggt taaacaggcg   120
ccgggtcaag tctgaaatg gatgggttgg atcaacacct acaccggtga agcacctac     180
gttgacgatt tcaaaggtcg tttcgttttc agcctggata ccagcgttag cgcggcctac   240
ctgcagatca gctctctgaa agcggaagac accgcgacct acttctgcgc gcgtcgcggt   300
ttctacgcga tggattactg gggccaaggg accacggtca ccgtctcctc agacatcgta   360
ctgacccaga gccggcgac catgagcgcg agccgggtg aacgtgttac cctgacctgc    420
agcgcgagct ctagcatcag ctatatgttc tggtatcatc agcgtccggg tcagagcccg   480
cgtctgttga tctatgatac cagcaacctg gcgagcggtg ttccggcgcg tttcagcggt   540
agcggtagcg gtaccagcta tagcctgacc atcagccgta tggaaccgga agatttcgcg   600
acctatttct gccatcagag ctctagctat ccgttcacct tcggtcaggg taccaaactc   660
gagatcaaac gg                                                       672
```

<210> SEQ ID NO 102
<211> LENGTH: 230
<212> TYPE: PRT
<213> ORGANISM: Artificial Sequence
<220> FEATURE:
<223> OTHER INFORMATION: SYNTHETIC

<400> SEQUENCE: 102

Gln Val Gln Leu Val Gln Ser Gly Ser Glu Leu Lys Lys Pro Gly Ala
1               5                   10                  15

Ser Val Lys Ile Ser Cys Lys Ala Ser Gly Tyr Thr Phe Thr Asp Tyr
            20                  25                  30

Gly Met Asn Trp Val Lys Gln Ala Pro Gly Gln Gly Leu Lys Trp Met
        35                  40                  45

Gly Trp Ile Asn Thr Tyr Thr Gly Glu Ser Thr Tyr Val Asp Asp Phe
    50                  55                  60

Lys Gly Arg Phe Val Phe Ser Leu Asp Thr Ser Val Ser Ala Ala Tyr
65                  70                  75                  80

Leu Gln Ile Ser Ser Leu Lys Ala Glu Asp Thr Ala Thr Tyr Phe Cys

```
                          85                      90                      95
Ala Arg Arg Gly Phe Tyr Ala Met Asp Tyr Trp Gln Gly Thr Thr
            100                 105                 110
Val Thr Val Ser Ser Asp Ile Val Leu Thr Gln Ser Pro Ala Thr Met
            115                 120                 125
Ser Ala Ser Pro Gly Glu Arg Val Thr Leu Thr Cys Ser Ala Ser Ser
    130                 135                 140
Ser Ile Ser Tyr Met Phe Trp Tyr His Gln Arg Pro Gly Gln Ser Pro
145                 150                 155                 160
Arg Leu Leu Ile Tyr Asp Thr Ser Asn Leu Ala Ser Gly Val Pro Ala
                165                 170                 175
Arg Phe Ser Gly Ser Gly Ser Gly Thr Ser Tyr Ser Leu Thr Ile Ser
            180                 185                 190
Arg Met Glu Pro Glu Asp Phe Ala Thr Tyr Phe Cys His Gln Ser Ser
            195                 200                 205
Ser Tyr Pro Phe Thr Phe Gly Gln Gly Thr Lys Leu Glu Ile Lys Arg
    210                 215                 220
His His His His His His
225                 230

<210> SEQ ID NO 103
<211> LENGTH: 40
<212> TYPE: DNA
<213> ORGANISM: UNKNOWN
<220> FEATURE:
<223> OTHER INFORMATION: GENOMIC

<400> SEQUENCE: 103
ctgggtcagt acgatgtctg aggagacggt gaccgtggtc                              40

<210> SEQ ID NO 104
<211> LENGTH: 37
<212> TYPE: DNA
<213> ORGANISM: UNKNOWN
<220> FEATURE:
<223> OTHER INFORMATION: GENOMIC

<400> SEQUENCE: 104
gtcaccgtct cctcagacat cgtactgacc cagagcc                                 37
```

INTERFERON-GAMMA-BINDING MOLECULES FOR TREATING SEPTIC SHOCK, CACHEXIA, IMMUNE DISEASES AND SKIN DISORDERS

This application is a section 371 national stage filing of PCT/EP98/05165, filed Aug. 14, 1998 (published in English on Feb. 25, 1999 As WO 99/09055) and claiming priority to EP 97870122.5 filed Aug. 18, 1997; and EP 98870139.7 filed Jun. 18, 1998.

FIELD OF THE INVENTION

The present invention concerns molecules which bind and neutralize the cytokine interferon-gamma. More specifically, the present invention relates to sheep-derived antibodies and engineered antibody constructs, such as humanized single-chain Fv fragments, chimeric antibodies, diabodies, triabodies, tetravalent antibodies and peptabodies which can be used to treat diseases wherein interferon-gamma activity is pathogenic. Examples of such diseases are: septic shock, cachexia, multiple sclerosis and psoriasis.

BACKGROUND OF THE INVENTION

Interferon-gamma (IFNγ) is a member of the interferon family of immunomodulatory proteins and is produced by activated T helper type-1 cells (Th1 cells) and natural killer cells (NK cells). Apart from its potent antiviral activity, IFNγ is known to be involved in a variety of immune functions (for a review, see Billiau, 1996) and inflammatory responses. Indeed, IFNγ is the primary inducer of the expression of the major histocompatibility complex (MHC) class-II molecules (Steinman et al., 1980) by macrophages and other cell types and stimulates the production of inflammatory mediators such as tumor necrosis factor-alpha (TNFα), interleukin-1 (IL-1) and nitric oxide (NO) (Lorsbach et al., 1993). In this respect, IFNγ is shown to be important in the macrophage-mediated defence to various bacterial pathogens. Furthermore, IFNγ is also shown to be a potent inducer of the expression of adhesion molecules, such as the intercellular adhesion molecule-1 (ICAM-1, Dustin et al., 1988), and of important costimulators such as the B7 molecules on professional antigen presenting cells (Freedman et al., 1991). Moreover, IFNγ induces macrophages to become tumoricidal (Pace et al., 1983) and provokes Ig isotype switching (Snapper and Paul, 1987).

The anti-viral, tumoricidal, inflammatory- and immunomodulatory activity of IFNγ clearly has beneficial effects in a number of clinical conditions. However, there are a number of clinical situations in which IFNγ-activity has deleterious effects. These include cancer cachexia (Denz et al., 1993; Iwagaki et al., 1995), septic shock (Doherty et al., 1992), skin disorders such as psoriasis and bullous dermatoses (Van den Oord et al., 1995), allograft rejection (Landolfo et al., 1985; Gorczynski, 1995), chronic inflammations such as ulcerative colitis and Crohn's disease (WO 94/14467 to Ashkenazi & Ward), and autoimmune diseases such as multiple sclerosis (MS, Panitch et al., 1986), experimental lupus (Ozmen et al., 1995), arthritis (Jacob et al., 1989; Boissier et al., 1995) and autoimmune encephalomyelitis (Waisman et al., 1996).

Cachexia is a phenomenon often seen in cancer patients and is associated with losses of lean body mass, and altered carbohydrate and lipid metabolism. This so called 'chronic wasting syndrome' is often the immediate cause of death. In recent years, interest has focused on the role of proinflammatory cytokines in cancer related cachexia. Current data support the concept that cachexia is linked to the presence of certain cytokines among which IFNγ seems to play a central role. Denz et al. (1993) reported that increased neopterin and decreased tryptophan concentrations—which are closely related to IFNγ-activity—are detected in cachectic patients suffering from hematological disorders. Neopterin is synthesized and secreted by monocytes/macrophages upon stimulation by IFNγ from activated T cells. Tryptophan is an indispensable amino acid which can be catabolized by indoleamine 2,3-dioxygenase, an enzyme induced by IFN's, and which absence initiates mechanisms responsible for cachexia (Brown et al., 1991). The correlation between high neopterin levels, decreased tryptophan levels and weight loss was confirmed by Iwagaki et al. (1995). In experimental models, cancer-induced cachexia can be altered by the administration of IFNγ neutralizing antibodies (Matthys et al., 1991; Langstein et al., 1991)

Septic shock is the result of a severe bacterial infection, and remains a common cause of death among critically ill, hospitalized patients despite improvements in supportive care (Bone et al., 1992). Although septic shock may be associated with gram-positive infections, attention has focused on the more common pathogenesis of gram-negative sepsis and the toxic role of endotoxin (=lipopolysaccharide or LPS), a component of the outer membrane of gram-negative and some gram-positive bacteria. Many of the effects of LPS are mediated through the release of cytokines such as TNFα (Tracey, 1991), IL-1 (Wakabayashi et al., 1991) and IFNγ (Bucklin et al., 1994). Much of the evidence supporting the role of these cytokines as mediators of septic shock comes from lethality studies involving the blockade of individual cytokines, resulting in protection of experimental animals from otherwise lethal doses of endotoxin or gram-negative bacteria. One of the first events in septic shock is the activation of T cells by antigen presenting cells onto which bacterial superantigen is bound (Miethke et al., 1993). Upon activation, for which co-stimulation of CD28 is essential (Saha et al., 1996), these T cells proliferate and produce a surge of proinflammatory cytokines such as IL-2, TNFα and IFNγ eventuating in the clinical syndrome. Also, it is hypothesized that LPS induces the expression of the α1/β1 integrin (VLA-1) heterodimer on activated monocytes which then display an increased capacity to adhere to the endothelial basement membrane. Similar effects can be induced by incubation of monocytes with IFNγ (Rubio et al., 1995). VLA-1 might also contribute to further monocyte activation and potentiation of the production of monocyte-derived pro-inflammatory cytokines during sepsis (Rubio et al., 1995). Although very promising results were obtained with antibodies neutralising TNFα in experimental animal models, clinical trials with anti-TNFα antibodies revealed only a slight reduction or even no reduction in mortality rate of patients with septic shock (Wherry et al., 1993; Reinhart et al., 1996). A fusion protein containing the extracellular portion of the TNF receptor and the Fc portion of IgG1 also did not affect mortality (Fisher et al., 1996). Pentoxifylline (PTX), a methyl xanthine derivative, is currently being tested for its effect on the outcome of septic shock. PTX is known to lower the serum concentrations of at least TNFβ, IL-1 and IFNα (Bienvenu et al., 1995; Zeni et al., 1996). Initial data reveal that PTX leads to an improvement of the clinical status of septic patients (Mándi et al., 1995). There is evidence that IFNγ is a mediator of lethality during sepsis. Antibodies that either neutralize IFNγ or block the IFNγ-receptor are protecting against lethality (Bucklin et al., 1994; Doherty et al., 1992). A synergistic effect between IFNγ and TNFα has also been suggested (Doherty et al., 1992; Ozmen et al., 1994). Although not in itself lethal, IFNγ has been shown to be essential for the manifestation of TNF-induced lethality in the generalized Shwartzman reaction (Ozmen et al., 1994).

Bullous, inflammatory and neoplastic dermatoses are a heterogenous group of skin disorders during which IFNγ may play a pathogenic role. Bullous dermatoses encompass epidermolysis bullosa acquisita, bullous pemhigoid, dermatitis herpetiformes Duhring, linear IgA disease, herpes gestationis, cicatricial pemhigoid, bullous systemic lupus erythematosis, epidermolysis bullosa junctionalis, epidermolysis bullosa dystrophicans, porphyria cutanea tarda and Lyell-Syndrome (Megahed, 1996). Also erythema exsudativum multiform major (Kreutzer et al., 1996), IgG-mediated subepidermal bullous dermatosis (Chan & Cooper, 1994), bullous lichen planus (Willsteed et al., 1991) and paraneoplastic bullous dermatosis (Pantaleeva, 1990) can be classified among the bullous dermatoses. A pathogenic role of IFNγ during bullous dermatoses has been suggested by Van den Oord et al. (1995). The role of IFNγ during inflammatory and neoplastic dermatoses, compared to bullous dermatoses, has been more extensively investigated. Indeed, it has been demonstrated that IFNγ is involved during the pathogenesis of verrucosis (Asadullah et al., 1997), eosinophilic pustular folliculitis (Teraki et al., 1996), cutaneous T cell lymphoma (Wood et al., 1994), granuloma faciale (Smoller & Bortz, 1993), Sweet's syndrome (Reuss-Borst et al., 1993), atopic eczema (Arenberger et al., 1991), follicular mucinosis (Meisnerr et al., 1991), lichen-planus and psoriasis (Vowels et al., 1994). One of the most extensively studied inflammatory dermatoses is psoriasis. Psoriasis is a hyperproliferative skin disorder affecting approximately 2% of the population. Evidence is accumulating that the disease has a T-cell mediated autoimmune etiology. The role of T-cells in psoriasis has been demonstrated by Gottlieb et al. (1995). The latter authors suggested that, in most of the patients, clinical and histopathological features of psoriasis are primarily linked to skin infiltration by IL-2 receptor-positive leukocytes. Disease improvement can be induced by the administration of a fusion protein composed of human interleukin-2 and fragments of diphteria toxin, which selectively blocks the growth of activated lymphocytes. Other effective anti-psoriatic, T-cell suppressing agents include the immunosuppressive drugs cyclosporin and FK506 (Griffiths, 1986) and anti-CD4 monoclonal antibodies (Morel et al., 1992). More direct evidence for the role of T cells in the induction of the complex tissue alterations seen in psoriasis has been generated by Schön et al. (1997) using a model with scid/scid mice in which they transferred naive, minor histocompatibility mismatched CD4+ T-cells, resulting in the development of a skin disorder that resembles psoriasis. The autoimmune character of the disease has been proposed by Valdimarsson et al. (1995) who stated that products of activated T-cells can induce keratinocytes of individuals with psoriatic predisposition to express determinants that are recognized by T cells specific for epitopes on β-haemolytic streptococci. Several data suggest that IFNγ may play a crucial role in the pathogenesis of psoriasis. IFNγ, produced by activated T cells would be involved in the recruitment of lymphocytes (Nickoloff, 1988), in the induction of activation and adhesion molecules on epidermal keratinocytes (Dustin et al., 1988), as well as in the abnormal keratinocyte proliferation (Barker et al., 1993). Not only enhanced levels of IFNγ has been detected in psoriatic epidermis (Kaneko et al., 1990), also de novo suprabasal expression of IFNγ receptor in psoriasis has been demonstrated (Van den Oord et al., 1995).

Inflammatory bowel disease (IBD), which encompasses ulcerative colitis and Crohn's disease, is characterized by the appearance of lesions of unknown aetiology in most parts of the gut. IBD is rather common, with a prevalence in the range of 70–170 in a population of 100,000. The current therapy of IBD involves the administration of anti-inflammatory or immunosuppressive agents, which usually bring only partial results, and surgery. In view of the apparent shortcomings of the present treatment, Ashkenazi and Ward (WO 94/14467) suggested the usage of a bispecific antibody construct targeting IFNγ and another molecule, such as IL-1 and TNFα, to treat IBD. However, the exact role of IFNγ during IBD is not well understood.

MS is a severely disabling progressive neurological disease of unknown aetiology, but probably involving autoimmune responses and resulting in the appearance of focal areas of demyelinisation (Williams et al., 1994). MS affects 1 in 1000 persons in the USA and Europe, but due to improved diagnosis that number is increasing. Onset of disease is usually around 30 years of age and, on average, patients are in need of treatment for another 28 years. MS is among the most expensive chronic diseases of western society, based on duration and intensity of care. However, diagnosis of exacerbations and early identification of onset of exacerbations has improved greatly, allowing design of novel treatment strategies. Active multiple sclerosis lesions feature T-lymphocyte and monocyte-macrophage accumulations at plaque margins where myelin is being destroyed. The inflammatory cells that invade the white matter and the soluble mediators that they release are held primarily responsible for myelin breakdown. Population-based studies indicate that certain HLA-antigens occur with higher frequency in patients with MS (with predominant MHC being the Dw2(DR2)DQ1.2 haplotype (Olerup et al., 1991). Similar associations of class I and class II haplotypes have also been detected in other autoimmune disorders such as rheumatoid arthritis and insulin dependent diabetes (Nepom, 1993). The lesions of MS are comparable to those found in chronic relapsing experimental allergic encephalitis (EAE), an autoimmune disease that can be induced in animals by immunization with e.g. whole myelin (Allen et al., 1993) or with the myelin/oligodendrocyte glycoprotein (Genain et al., 1995b). The lesions associated with EAE are similar in appearance as the ones occurring in MS and also contain inflammatory infiltrates of T-cells and macrophages (Genain et al., 1995b). Furthermore, in adoptive transfer experiments, T cells sensitized to specific myelin antigens can transfer the disease state of EAE (Genain et al., 1995b; Waldburger et al., 1996). A few years ago, the American FDA approved the use of the immunosuppressive drug interferon (trade name Betaseron) for treatment of chronic relapsing MS. The effect of this drug—although modest—clearly demonstrates the involvement of the cytokine network in the pathophysiology of MS. In the last few years, a large number of studies have addressed the molecular mechanism by which Betaseron exerts its beneficial effects. Lately, it was shown that IFNβ dose-dependently inhibited T-cell proliferation, expression of IL-2 receptors and secretion of IFNγ, TNFα and IL-13 (Rep et al., 1996). Furthermore, it was demonstrated that IFNβ could specifically prevent the IFNγ-induced up regulation of MHC class II antigens and adhesion molecules on antigen-presenting cells (Jiang et al., 1995) and human brain microvessel endothelial cells (Huynh et al., 1995).

One of the earliest events in MS is damage of the blood brain barrier (BBB) by activated, encephalitogenic T-cells (Tsukada et al., 1993). The mechanism by which these cells destruct locally the BBB, which is mainly constituted of endothelial cells, is not elucidated, but it is known that at the systemic level, local production of certain cytokines such as IFNγ enhance the capability of lymphocytes to adhere to endothelial cells (Yu et al., 1985; Tsukada et al., 1993). Also, on choroid plexus epithelial cells of EAE animals, an increased expression of ICAM-1 and VCAM-1 (Steffen et al., 1994), for which LFA-1 and VLA-4 are the natural ligands on lymphocytes, has been observed. Mc Carron et al. (1993) reported that adhesion of MBP-specific T lymphocytes was significantly up regulated when cerebral endothelial cells were treated with IL-1, TNFα or IFNγ. That the adhesion of encephalitogenic T-cells to the endothelium is an early and very important event in the onset of MS is shown by the finding that anti LFA-1 therapy can completely block the induction of EAE (Gordon et al., 1995). Additional circumstantial evidence for a stimulatory role of IFNγ in the pathophysiology of MS comes from observations that disease exacerbations are induced by viral upper respiratory infections, known to stimulate the secretion of IFNγ by type-2 helper T cells (Panitch, 1994). The proinflammatory role of IFNγ in autoimmune disease is strengthened by an earlier finding that treatment of MS patients with hIFNγ resulted in an aggravation of the symptoms (Panitch et al., 1986). The role of IFNγ as proinflammatory cytokine in autoimmune disorders has been studied in several experimentally induced forms of autoimmunity. In experimental neuritis, induced by myelin or antigen-specific T cells in rat, IFNγ clearly acted as pro-inflammatory cytokine and administration of a monoclonal antibody to IFNγ suppressed the disease (Hartung et al., 1990). In the case of experimental autoimmune thyroiditis (EAT) in mice, induced by the injection of thyroglobulin, treatment of the animals with anti-IFNγ at 4 weeks after induction of EAT proved to be beneficial, since characteristic features of EAT such as the lymphocytic infiltrations of the thyroid glands and the serum levels of autoantibodies to thyroglobulin, were significantly reduced (Tang et al., 1993).

In the mouse EAE model for MS, where the disease can be induced by injection of either spinal cord homogenate or myelin basic protein, elevated concentrations of several cytokines, including IFNγ were observed both in serum and in the lesions in the CNS (Willenborg et al., 1995). However, administration of anti-IFNγ at the initiation of the disease, resulted in an exacerbation of the disease (Billiau et al., 1988; Duong et al., 1994; Willenborg et al., 1995). It must be noted, however, that in these experiments the effect of anti-IFNγ was determined at the onset of acute EAE rather than at the time of chronic relapse of the disease, which in fact is the only relevant situation for MS. Pathologically, typical acute EAE differs substantially from MS in that prominent inflammation occurs in gray, white and meningeal structures, but demyelisation is scant or absent (Genain et al., 1995b). In order to explain the findings with anti-IFNγ antibodies, the authors suggest a different action of IFNγ at the systemic level (anti-inflammatory action) compared to the local level (inflammatory action) (Billiau et al., 1988), or suggest an early role (within 24h after immunization) of IFNγ in disease resistance (Duong et al., 1994). Willenborg et al. (1995) conclude that the time of treatment plays a critical role on the outcome and suggest this to be the explanation for conflicting results in different autoimmune processes. Recently, Heremans et al. (1996) described facilitation of spontaneous relapses in chronic relapsing EAE in Biozzi ABH mice by administration of anti-IFNγ during the remission phase. The onset of relapses was delayed when animals were treated with IFNγ during the remission phase, results which are in contradiction to the excacerbation seen in humans who were treated with hIFNγ.

An experimental EAE model that more closely resembles the disease course and symptomatology of MS in humans can be found in marmosets. Indeed, in these animals a chronic relapsing-remitting form of EAE can be induced which is characterized by an initial, acute phase with clinically mild neurological signs, followed by recovery. A late spontaneous relapse occurs in these animals and chronic lesions resemble active plaques of chronic MS (Massacesi et al., 1995). This unique model can efficiently be employed to evaluate a prospective therapy for MS. In this model, a critical role for TNFα in demyelisation is suggested by the observation that rolipram, a selective inhibitor of the type IV phosphodiesterase, suppressed TNFα secretion and demyelisation (Genain et al., 1995a; Sommer et al., 1995) when administered shortly after immunization, thus interfering with acute EAE. The effect of anti-IFNγ on acute EAE or on disease relapse has to our knowledge never been investigated in marmoset.

Taken together, it is well established that there are a number of clinical situations in which IFNγ-activity has deleterious effects. Consequently, several potential therapies to neutralize IFNγ-activity have been proposed. Among the latter proposals are the use of: anti-IFNγ antibodies (Ozmen et al., 1995; Bucklin et al., 1994), recombinant anti-IFNγ Fv fragments (EP 0528469 to Billiau & Froyen), bispecific molecules (WO 94/14467 to Ashkenazi and Ward), drugs such as pentoxifylline (Bienvenu et al., 1995), synthetic polypeptides which inhibit binding of IFNγ to its receptor (U.S. Pat. No. 5,451,658 to Seelig; U.S. Pat. No. 5,632, 988 to Ingram et al.), Epstein-Barr virus derived proteins (U.S. Pat. No. 5,627,155 to Moore & Kastelein), soluble IFNγ receptors (EP 0393502 to Fountoulakis et al.; U.S. Pat. No. 5,578,707 to Novick & Rubinstein) and oligonucleotides which bind to IFNγ (WO95/00529 to Coppola et al.). However, these compounds are faced with problems such as suboptimal stability, affinity and clearance rates, lack of specificity, efficacy and tissue penetrance, toxic side effects and unwanted carrier effects. Indeed, the carrier effect of antibodies can limit their efficiency to block the target cytokine. For example, Montero-Julian et al. (1995) showed that during treatment of myeloma patients with anti-IL-6, accumulation of IL-6 in the serum in the form of monomeric immune complexes occurred, hereby stabilizing the cytokine. Furthermore, it has also been shown that the therapeutic efficacy of a cytokine can be prolonged by the formation of cytokine/antibody complexes, since the efficacy of recombinant human IL-2 treatment could be increased by prolonging its in vivo half-life by complexing with an anti-IL-2 antibody (Courtney et al., 1994). The carrier-effect of anti-cytokine antibodies can be overcome by the construction of monovalent scFv fragments, although their low MW (∀30.000) and the associated fast clearance rate, make them less suitable candidates for long-term treatment. However, the undesirable carrier effect can be avoided by the formation of higher immune complexes, as such increasing the clearance of the cytokine-antibody complexes (Montero-Julian et al., 1995). The use of monoclonal antibodies for diagnostic or therapeutic purposes in vivo is, besides the carrier effect, also limited because of their nature (i.e. the majority are murine mAb's and administration of antibodies of mouse origin inevitably results in a human anti-mouse antibody [HAMA] response), their suboptimal efficacy, stability and affinity and their large molecular size. Proposed solutions to some of these problems involve the use of F(ab')2, F(ab) and scFv derivatives or of humanized versions of the parent antibody, either by CDR grafting (Kettleborough et al., 1991) or by resurfacing of the antibodies (Roguska et al., 1994). Another proposed solution is the development of several modified antibodies or antibody constructs by bioengineering or chemical methods. Indeed, some mAb's were made more effective by conjugating chemotherapeutic drugs and other toxins to the antibodies (Ghetie and Vitetta, 1994) or by developing bispecific and/or multivalent antibody constructs capable of simultaneously binding several—or two different epitopes on the same—or different antigens. These antibody constructs have been produced using a variety of methods: a) antibodies of different specificities or univalent fragments of pepsin-treated antibodies of different specificities have been chemically linked (Fanger et al., 1992); b) two hybridomas secreting antibodies of different specificity have been fused and the resulting bispecific antibodies from the mixture of antibodies were subsequently isolated; c) genitically engineered single chain antibodies have been used to produce non-covalently linked bispecific antibodies (e.g. diabodies (Holliger et al., 1993), minibodies (Kostelny et al., 1992) and tetravalent antibodies (Pack et al; 1995; WO 96/13583 to Pack) or covalently-linked bispecific antibodies (e.g. chelating recombinant antibodies (Kranz et al., 1995), single chain antibodies fused to protein A or Streptavidin (Ito and Kurosawa, 1993; Kipriyanov et al., 1996) and bispecific tetravalent antibodies (EP 0517024 to Bosslet and Deeman). Recently, also trivalent antibody constructs, named triabodies (Kortt et al., 1997), and pentavalent constructs, named peptabodies (Terskikh et al., 1997), have been described. These constructs may have a higher avidity in comparison to bivalent constructs and may be useful for diagnostic or therapeutic purposes in vivo.

However, and despite the fact that several potential therapies to neutralize IFNγ-activity have been proposed, no prior art exists regarding the production and existence of engineered antibody constructs, such as humanized single-chain Fv fragments, diabodies, triabodies, tetravalent antibodies, peptabodies and hexabodies, and ruminant-derived antibodies such as sheep antibodies which overcome the above-indicated problems and which can efficiently be used to treat diseases wherein interferon-gamma activity is pathogenic.

SUMMARY OF THE INVENTION

It is clear from the prior art as cited above that problems such as suboptimal stability, affinity, clearance rate, specificity, efficacy, and an unwanted carrier effect and HAMA response hamper the successful usage of several therapeutics which, potentially, could neutralize the activity of IFNγ. Also suggested solutions to overcome some of these problems did not result in the development of effective products. Thus, unpredictable and unknown factors still appear to determine the success of these biologicals. Despite these unknown factors, the present inventors have been able to design and develop useful constructs which effectively neutralize IFNγ-activity. Indeed, the constructs have all a surprisingly high affinity for IFNγ, they do not provoke a HAMA or related response, and they do not result in a carrier effect. In addition, some of the constructs pass the blood brain barrier, whereas others have a very good clearance rate. Therefore, the present invention aims at providing a molecule which binds and neutralizes interferon-gamma and which is chosen from the group consisting of:

- a scFv comprising the humanized variable domain of the monoclonal antibody D9D10
- a chimeric antibody comprising the humanized variable domain of the monoclonal antibody D9D10
- a diabody comprising the humanized variable domain of the monoclonal antibody D9D10
- a multivalent antibody
- a ruminant antibody.

The present invention further aims at providing a multivalent antibody chosen from the group consisting of triabodies, tetravalent antibodies, peptabodies and hexabodies.

The present invention also aims at providing a triabody, tetravalent antibody, peptabody and hexabody which comprise 3, 4, 5 and 6 variable domains, respectively, of different anti-interferon-gamma antibodies.

The present invention further aims at providing a triabody as described above which comprises 3 identical variable domains of an anti-interferon-gamma antibody. A preferred variable domain used in the latter constructs is derived from the mouse anti-interferon-gamma antibody D9D10 which is described by Sandvig et al. (1987) and Froyen et al. (1993) or from the sheep anti-interferon-gamma antibody described in the present application. Therefore, the present invention aims at providing a triabody as described above which comprises 3 identical D9D10 scFv's, 3 identical humanized D9D10 scFv's, 3 identical sheep-derived anti-interferon-gamma scFv's or 3 identical humanized sheep-derived anti-interferon-gamma scFv's.

The present invention further aims at providing a tetravalent antibody (called MoTAb I) as described above which comprises 4 identical domains of an anti-interferon-gamma antibody. More specifically, the present invention aims at providing a tetravalent antibody as described above which comprises either 4 identical D9D10 scFv's or 4 identical sheep-derived anti-interferon-gamma scFv's in the format of a homodimer of 2 identical molecules, each containing 2 D9D10 scFv's or 2 humanized D9D10 scFv's or 2 sheep-derived anti-interferon-gamma scFv's or 2 humanized sheep-derived anti-interferon-gamma scFv's, and a dimerization domain, or, a full-size humanized D9D10 antibody or sheep-derived anti-interferon-gamma antibody to which 2 humanized D9D10 scFv's or 2 humanized sheep-derived anti-interferon-gamma scFv's, respectively, are attached at the carboxyterminus (called MoTAb II) (see FIG. 1).

The present invention further aims at providing a peptabody and hexabody as described above which comprise 5 and 6 identical variable domains of an anti-interferon-gamma antibody, respectively. A preferred variable domain used in the latter constructs is derived from the mouse anti-interferon-gamma antibody D9D10 which is described above or from the sheep anti-interferon-gamma antibody described in the present application. Therefore, the present invention aims at providing a peptabody and hexabody as described above which comprises 5 or 6 identical D9D10 scFv's, 5 or 6 identical humanized D9D10 scFv's, 5 or 6 identical sheep-derived anti-interferon-gamma scFv's, or, 5 or 6 identical humanized sheep-derived anti-interferon-gamma scFv's, respectively.

The present invention further aims at providing a molecule as described above, wherein said ruminant antibody is a sheep antibody.

The present invention also aims at providing a molecule as described above, wherein said sheep antibody is a monoclonal antibody. Furthermore, the present invention aims at providing a humanized antibody, a single-chain fragment or any other fragment which is derived from said monoclonal antibody and which has largely retained the specificity of said monoclonal antibody.

Moreover, the present invention aims at providing methods for producing the above-described molecules.

The present invention further aims at providing a pharmaceutical composition comprising a molecule as described above, or a mixture of said molecules, in a pharmaceutically acceptable excipient.

The present invention also aims at providing a molecule or a composition as described above for use as a medicament.

Furthermore, the present invention aims at providing a molecule or a composition as described above for preventing or treating septic shock, cachexia, immune diseases such as multiple sclerosis and Crohn's disease and skin disorders such as bullous, inflammatory and neoplastic dermatosis.

Finally, the present invention aims at providing a molecule as described above for determining interferon gamma levels in a sample.

All the aims of the present invention are considered to have been met by the embodiments as set out below.

BRIEF DESCRIPTION OF THE FIGURES

FIG. 2 shows the coding (SEQ ID NO 1) and amino acid sequence (SEQ ID NO 2) of humanized D9D10 scFv (containing a C-terminal 6-histidine tag (bold)). CDR regions are underlined. Mutations (murine->human) are bold and underlined. The N-terminal pelB signal sequence is put in bold.

FIG. 7 shows the cDNA sequence encoding the humanized D9D10 heavy chain fusion protein.
  bp 1–60: D9D10 Kappa-light chain signal sequence
  bp 61–411: humanized D9D10 heavy chain variable domain
  bp 412–1401: human IgG1 heavy chain constant domain ($C_H1$-Hinge-$C_H2$-$C_H3$)
  bp 1402–1404: leu codon added by PCR cloning strategy (SEQ ID NO 66)

FIG. 8 shows the cDNA sequence encoding the humanized D9D10 and MoTAbII light chain fusion protein.
  bp 1–60: D9D10 Kappa-light chain signal sequence
  bp 61–381: humanized D9D10 light chain variable domain
  bp 382–699: human kappa light chain constant domain (SEQ ID NO 68)

FIG. 9 shows the amino acid sequence of the humanized D9D10 heavy chain fusion protein.
  Aa 1–20: D9D10 light chain signal sequence
  Aa 21–137: humanized heavy chain variable domain of D9D10
  Aa138–467: human IgG1 heavy chain constant domain ($C_H1$-hinge-$C_H2$-$C_H3$)
  Aa 468: leu added by PCR cloning strategy
  Aa 351: pro was mutated to ser: inactivation C1q complement binding
  Number of residues: 468.
  Molecular weight (MW): 51413 (SEQ ID NO 67)

FIG. 15 shows the cDNA sequence of MoTAbI
- bp 1–351: $V_H$ D9D10
- bp 352–396: $(G_4S)_3$ linker
- bp 397–717: $V_L$ D9D10
- bp 718–750: human IgG3 upper hinge
- bp 751–855: helix-turn-helix dimerisation domain
- bp 856–888: human IgG3 upper hinge
- bp 889–1239: $V_H$D9D10
- bp 1240–1284: $(G_4S)_3$ linker
- bp 1285–1605: $V_L$ D9D10
- bp 1606–1623: His6 tag (SEQ ID NO 84)

FIG. 16 shows the AA sequence of MoTAbI
- aa 1–117: $V_H$ D9D10
- aa 118–132: $(G_4S)_3$ linker
- aa 133–239: $V_L$ D9D10
- aa 240–250: human IgG3 upper hinge
- aa 251–285: helix-turn-helix dimerisation domain
- aa 286–296: human IgG3 upper hinge
- aa 297–413: $V_H$ D9D10
- aa 414–428: $(G_4S)_3$ linker
- aa 429–525: $V_L$ D9D10
- aa 526–531: His6 tag (SEQ ID NO 85)

FIG. 17 shows a schematic representation of the mammalian expression plasmid pEE12MoTAbII used for expression of D9D10 MoTAbII recombinant antibody in (1) COS cells (2) stable recombinant Ns0 cell lines.

Major Plasmid Building Blocks:
- prokaryotic sequences for plasmid DNA preparation in E.coli (ori of replication and $amp^R$ ampicilline resistance expression unit)
- SV40 origin of replication (part of SV40E, SV40 early promoter) allowing transient expression in SV40 permissive, T-antigen producing cell lines (e.g. COS)
- human Cytomegalovirus major immediate early promoter/enhancer (hCMVprom+intron) controlled expression casette for D9D10MoTAbII heavy chain protein (MoTAbII-H)
- human Cytomegalovirus major immediate early promoter/enhancer (hCMVprom+intron) controlled expression casette for D9D10MoTAbII light chain protein (MoTAbII-L)
- SV40 early promoter (SV40E) controlled glutamine synthetase cDNA (GS) expression unit for selection/amplification
- polyA=SV40 early region poly-adenylation signal
- intron+polyA=SV40 t-antigen intron+SV40 early region poly-adenylation signal

Major Plasmid Building Blocks:
- prokaryotic sequences for plasmid DNA preparation in E.coli (ori of replication and $amp^R$ ampicilline resistance expression unit)
- SV40 origin of replication (part of SV40E, SV40 early promoter) allowing transient expression in SV40 permissive, T-antigen producing cell lines (e.g. COS)
- human Cytomegalovirus major immediate early promoter/enhancer (hCMVprom+intron) controlled expression casette for D9D10MoTAbII heavy chain protein (MoTAbII-H)
- human Cytomegalovirus major immediate early promoter/enhancer (hCMVprom+intron) controlled expression casette for D9D10MoTAbII light chain protein (MoTAbII-L)
- SV40 late promoter (SV40L) controlled glutamine synthetase mini gene (GS+intron) expression unit for selection/amplification
- polyA=SV40 early region poly-adenylation signal
- intron+polyA=SV40 t-antigen intron+SV40 early region poly-adenylation signal FIG. 19 shows the cDNA sequence encoding the MoTABII fusion protein
- bp 1–60: D9D10 Kappa-light chain signal sequence
- bp 61–411: humanized D9D10 heavy chain variable domain
- bp 412–1401: human IgG1 heavy chain constant domain ($C_H1$-Hinge-$C_H2$-$C_H3$)
- bp 1402–1404: leu codon added by PCR cloning strategy
- bp 1405–1416 : gly(3)-ser codon
- bp 1417–2133: humanized D9D10 ScFv (SEQ ID NO 8: 9)

Figure 20B:
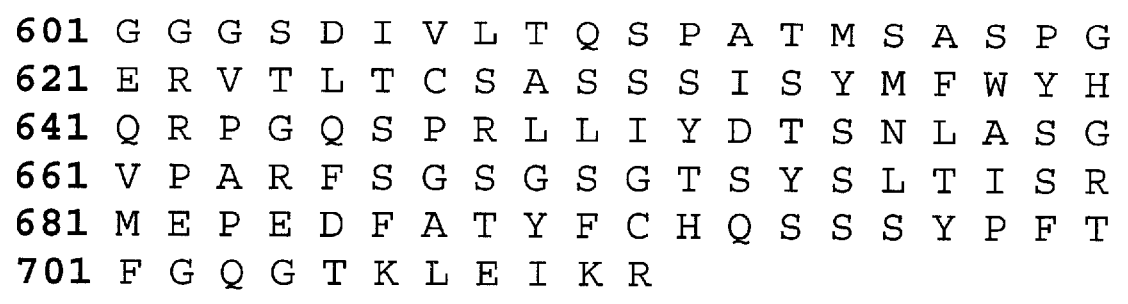

FIG. 20 shows the amino acid sequence of MoTABII fusion protein
- Aa 1–20: mouse D9D10 light chain signal sequence
- Aa 21–137: humanized heavy chain variable domain of D9D10
- Aa 138–467: human IgG1 heavy chain constant domain ($C_H1$-hinge-$C_H2$-$C_H3$)
- Aa 351: pro mutated to ser: inactivation C1q complement binding
- Aa 468: leu added by cloning strategy
- Aa 469–472: gly(3)-ser linker
- Aa 473–711: humanized D9D10 ScFv ($V_H$473–490/gly-ser linker/$V_L$605–711) (SEQ ID NO 90)

FIG. 22 shows the amino acid sequence of the D9D10 L10 diabody
- aa 1–117: $V_H$ D9D10
- aa 118–127: $(G_4S)_2$ linker
- aa 128–234: $V_L$ D9D10
- aa 235–240: His6-tag (SEQ ID NO 91)

FIG. 23 shows the coding sequence of the D9D10 L10 diabody
- bp 1–351: $V_H$ D9D10
- bp 352–381: $(G_4S)_2$ linker bp 382–702: $V_L$ D9D10 (SEQ ID NO 92)

FIG. 24 shows the amino acid sequence of the D9D10 L5 diabody aa 1–117: $V_H$ D9D10 aa 118–122: $G_4S$ linker aa 123–229: $V_L$ D9D10 aa 230–235: His6-tag 5SEQ ID NO 93)

FIG. 25 shows the coding sequence of the D9D10 L5 diabody bp 1–351: $V_H$ D9D10 bp 352–366: $G_4S$ linker bp 367–687: $V_L$ D9D10 (SEQ ID NO 94)

Figure 26:
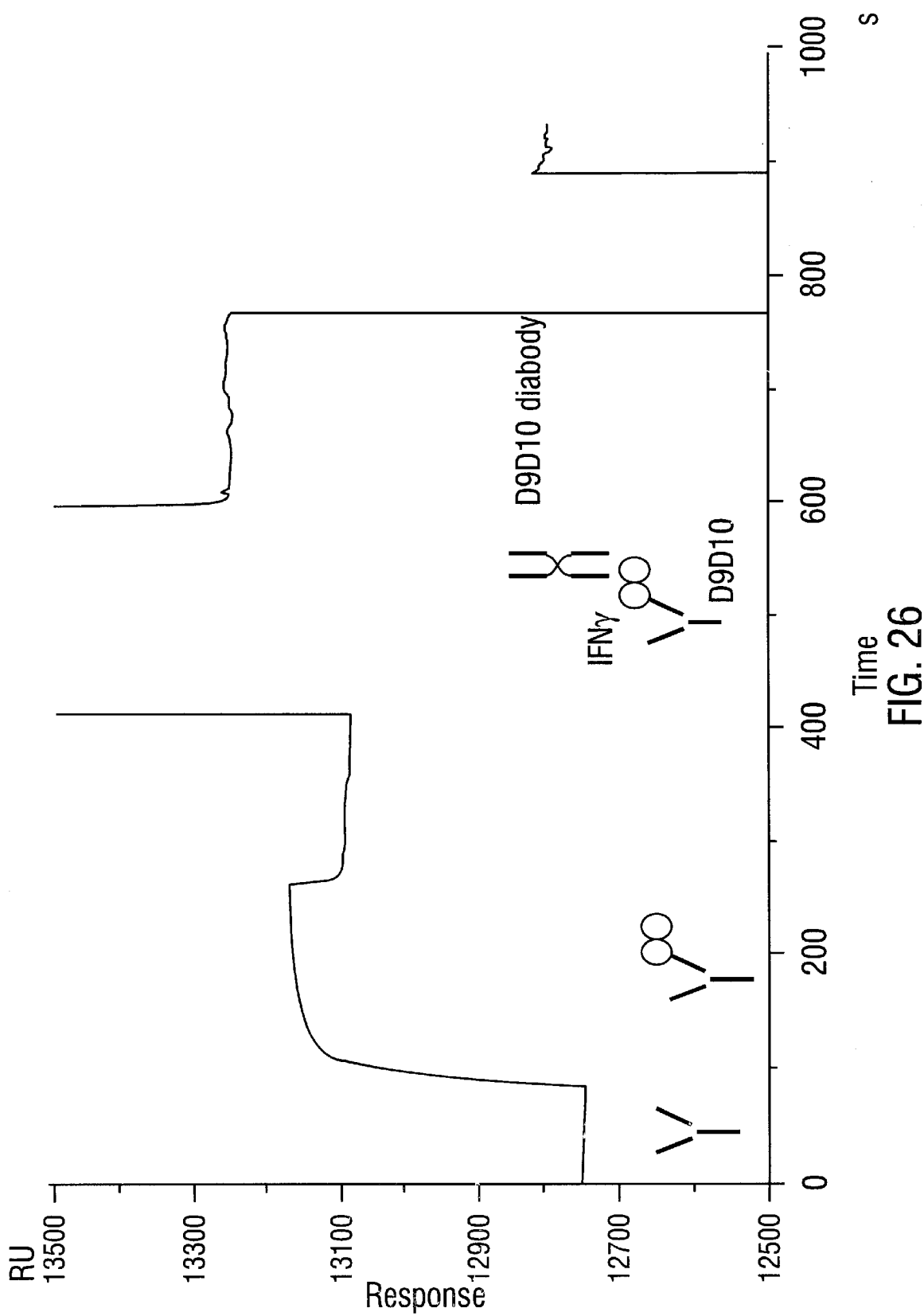

FIG. 26 shows the interaction of humanized L5 D9D10 diabody (=crude lysate from *E. coli*) with IFN using SPR analysis. The assay is performed as described in example 5.

FIG. 27 shows the coding sequence of the D9D10 triabody bp 1–351: $V_H$ D9D10 bp 352–672: $V_L$ D9D10 (SEQ ID NO 101)

FIG. 28 shows the amino acid sequence of the D9D10 L0 triabody aa 1–117: $V_H$ D9D10 aa 118–224: $V_L$ D9D10 aa 225–230: His6-tag (SEQ ID NO 102)

Figure 29:
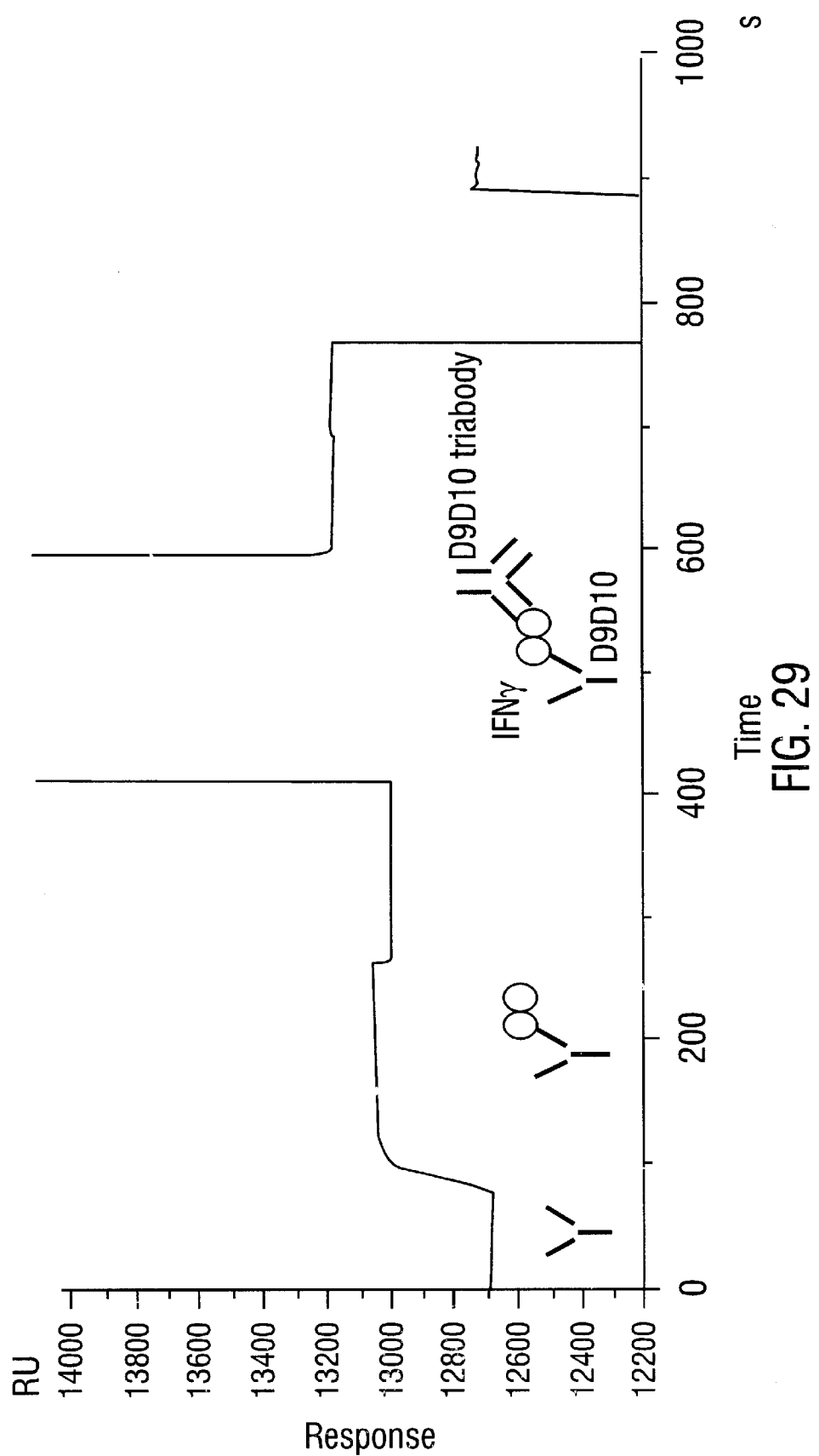

FIG. 29 shows the interaction of humanized L0 D9D10 triabody (=crude lysate from *E. coli*) with IFNγ using SPR analysis. The assay is performed as described in example 6.

Figure 30A:
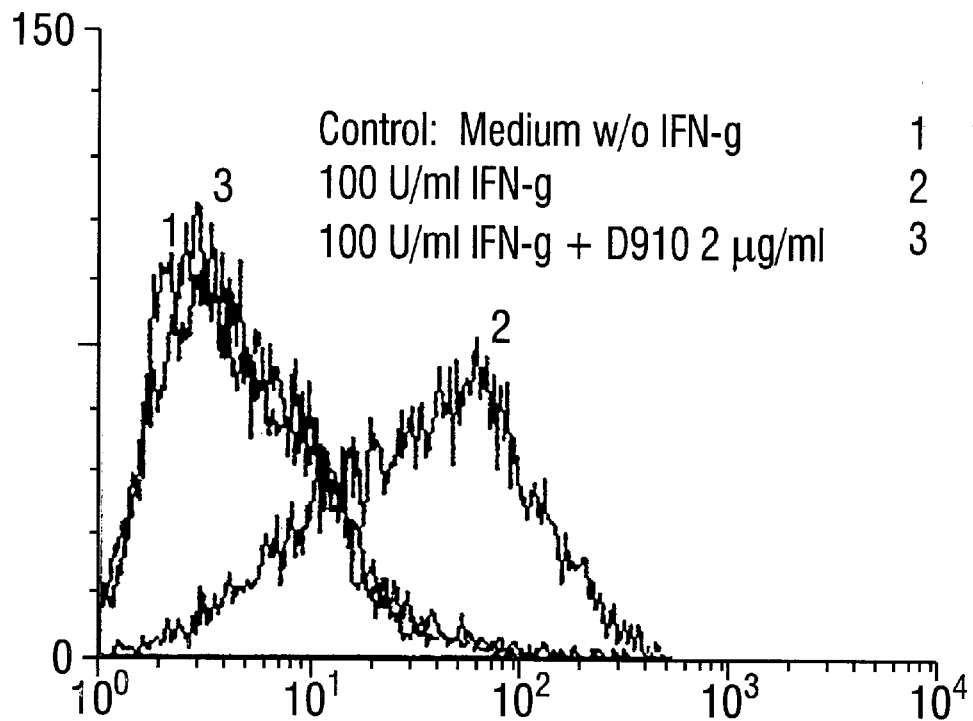
Figure 30B:
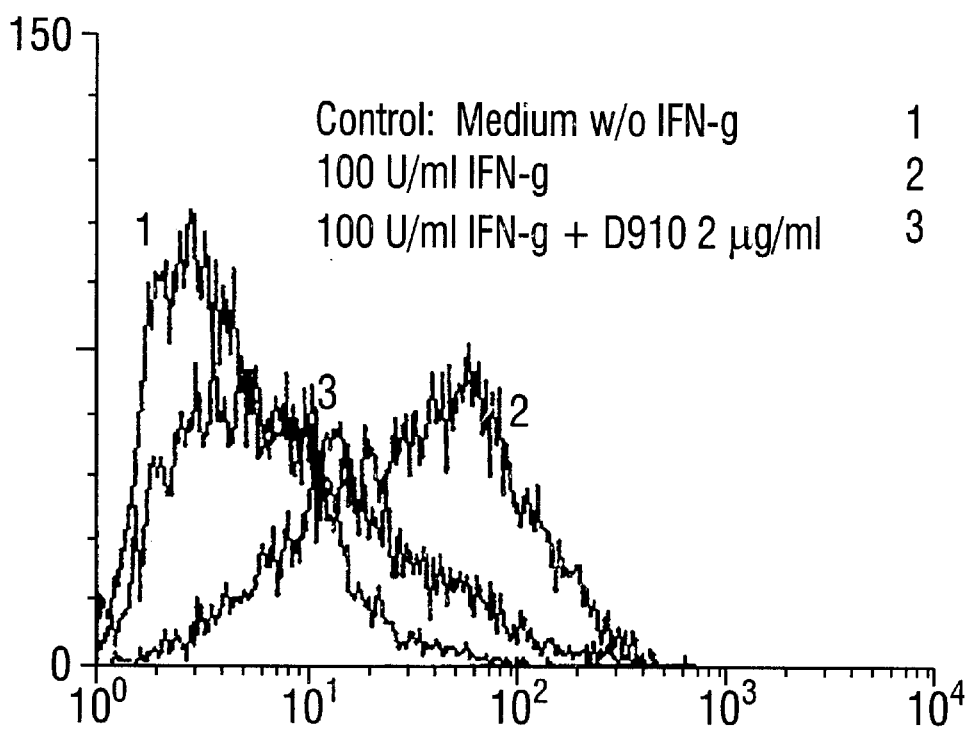
Figure 31A:
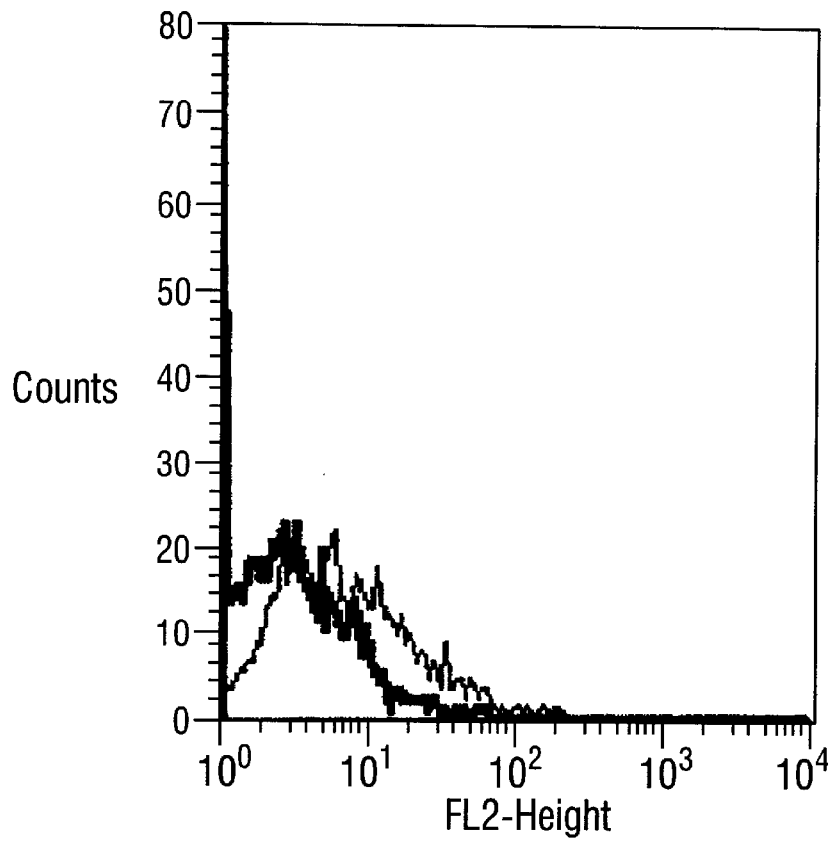
Figure 31B:
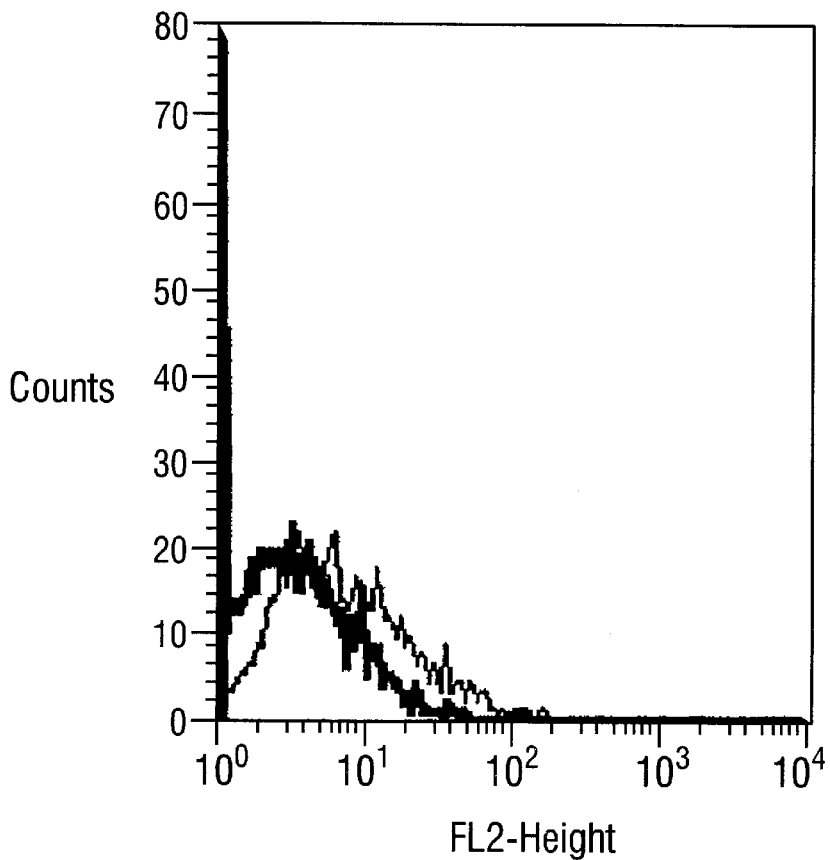
Figure 31C:
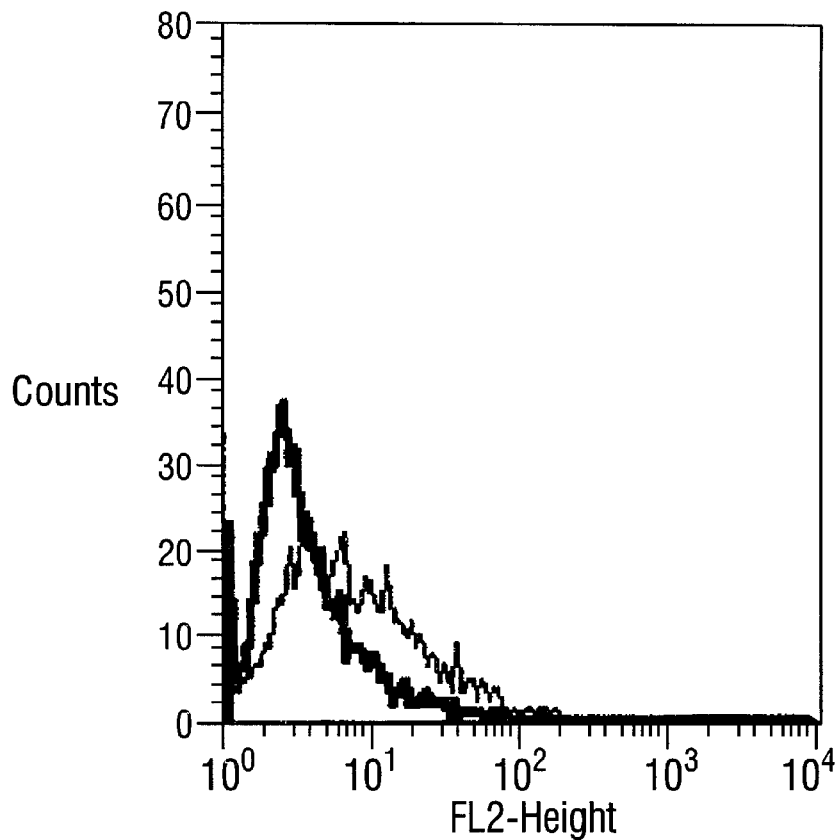
Figure 31D:
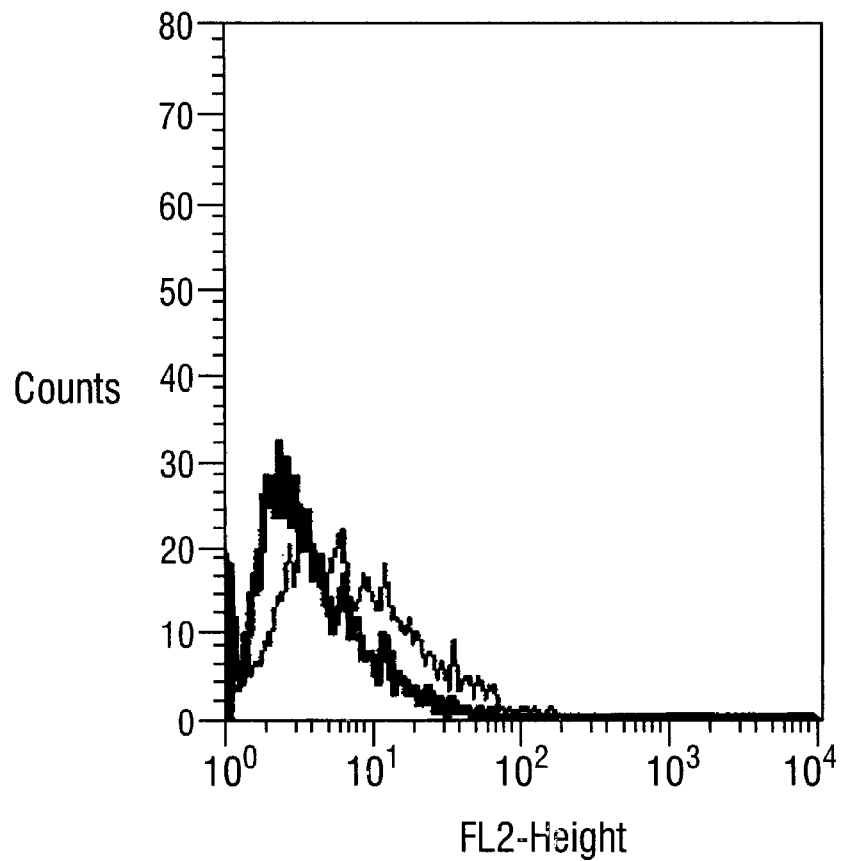

FIG. 30 shows the neutralization of IFN-gamma-induced MHC class II upregulation on human primary keratinocytes by D9D10 or D9D10 scFv. Human keratinocytes were cultured for 24 h with or without (not shown) 100 U/ml huIFN-gamma in the absence or the presence of D9D10 (2 μg/ml). Resting human keratinocytes do not express MHC class II. IFN-gamma induces expression of MHC class II in the keratinocytes and D9D10 (upper panel) or scFv D9D10 (lower panel) inhibit this IFN-gamma-induced MHC class II expression. See also further Example 7.1.

FIG. 31 shows the neutralization of IFN-gamma-induced MHC class II upregulation on human primary keratinocytes by crude COS supernatant containing either humanized D9D10 or MoTAbII. The experiment was performed as described in FIG. 30 thin line:
  human keratinocytes treated with human IFNγ
bold line:
  A: human keratinocytes not treated with human IFNγ
  B: effect of 400 ng/ml murine D9D10
  C: effect of humanized D9D10 (crude COS supernatant)
  D: effect of MoTAbII (crude COS supernatant)

Figure 32A:
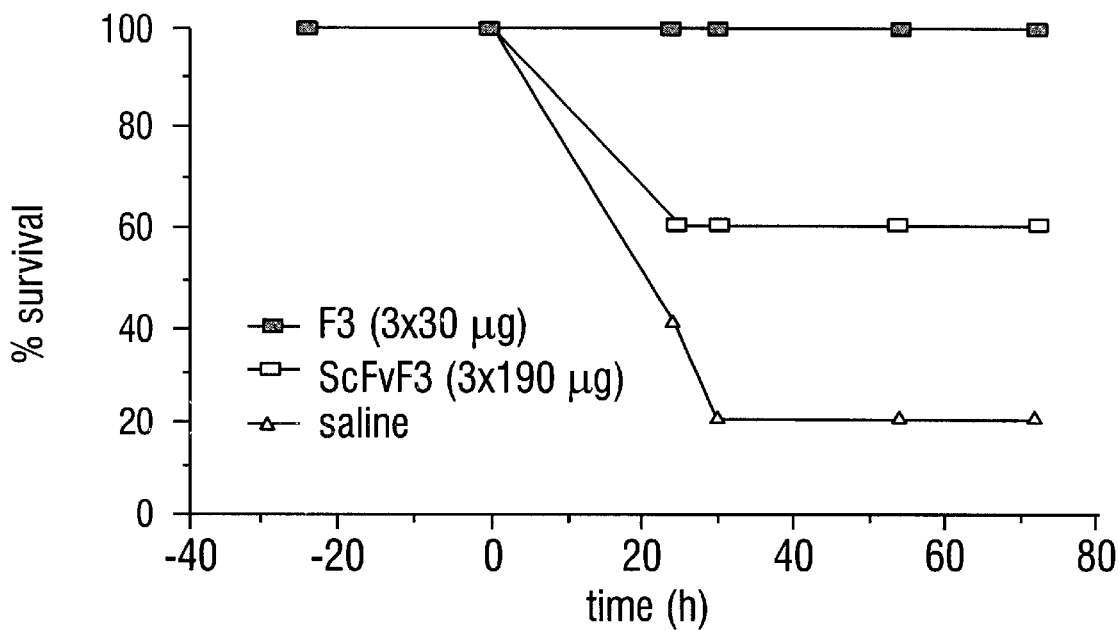
Figure 32B:
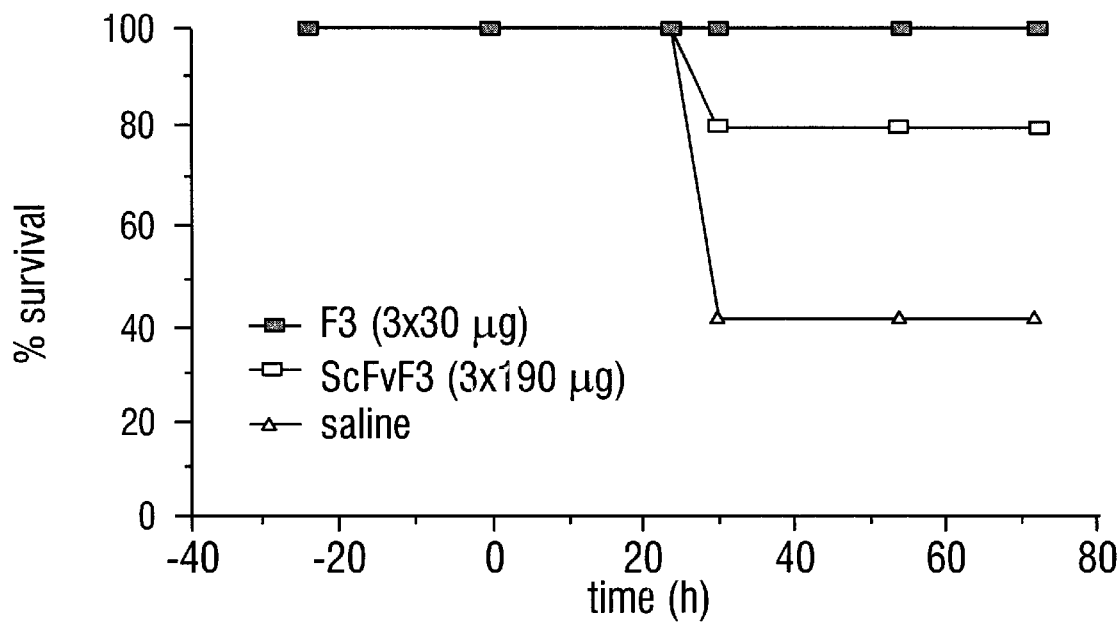

FIG. 32 shows the effect of the anti-IFN-gamma antibody F3 and scFvF3 on the survival of mice in which the lethal shock syndrome called "Shwartzman reaction" is induced. See also further Example 7.3.

Figure 33A:
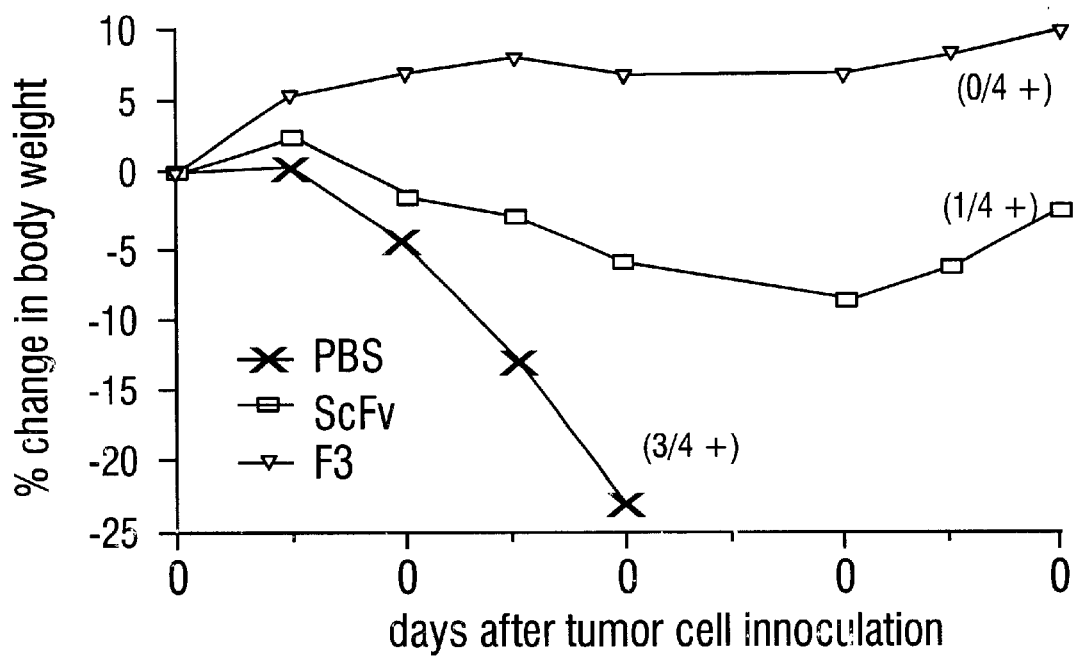
Figure 33B:
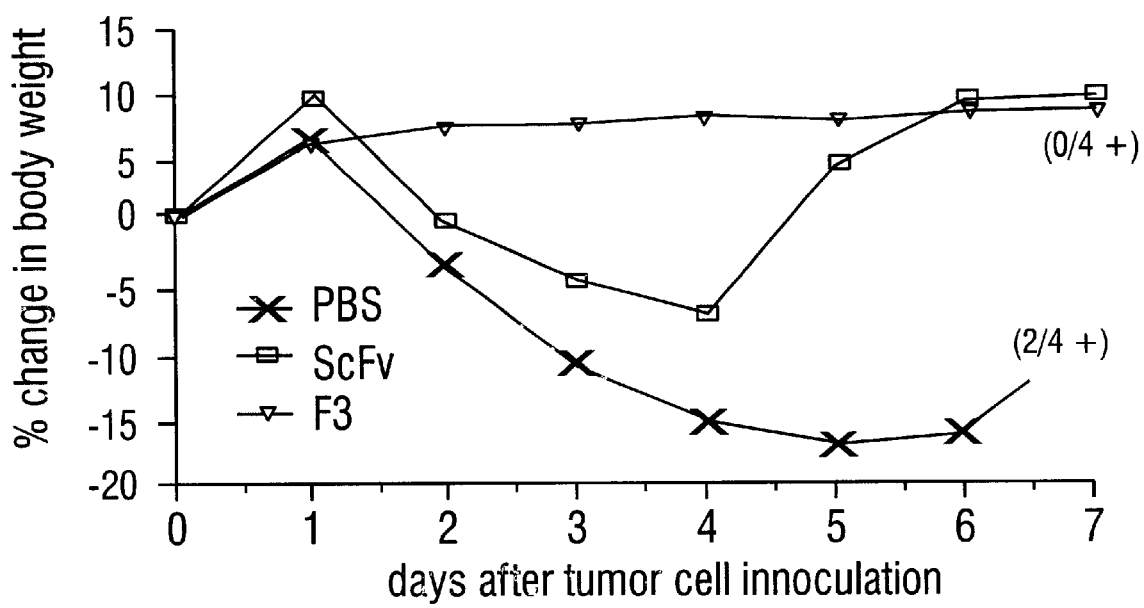

FIG. 33 shows the effect of the anti-IFN-gamma antibody F3 and scFvF3 on body weight of mice exhibiting IFN-gamma induced cachexia. Mortality (number of dead mice/total number of mice) is shown between brackets and the symbol "+". See also further Example 7.4.

DETAILED DESCRIPTION OF THE PREFERRED EMBODIMENTS

The invention described herein draws on previously published work and pending patent applications. By way of example, such work consists of scientific papers, patents or pending patent applications. All of these publications and applications, cited previously or below are hereby incorporated by reference.

The present invention is based on the finding that a molecule which binds and neutralizes human interferon-gamma and which is chosen from the group consisting of:

a scFv comprising the humanized variable domain of the monoclonal antibody D9D10 a chimeric antibody comprising the humanized variable domain of the monoclonal antibody D9D10 a diabody comprising the humanized variable domain of the monoclonal antibody D9D10 a multivalent antibody a ruminant antibody is useful to treat diseases where IFNγ activity is pathogenic.

As used herein the terms "molecule which binds and neutralizes IFNγ" refer to a molecule which recognizes and binds any particular epitope of IFNγ resulting in the neutralization of any bioactivity of IFNγ. Particular epitopes of IFNγ relate to the so-called E2 epitope recognized and bound by the mAb D9D10, the so-called E1 epitope (Kwok et al., 1993) or any other epitope. IFNγ specifically relates to human IFNγ but may also relate to non-human primate, mouse, rat, sheep, goat, camel, cow, llama or any other IFNγ. Furthermore, the term "bioactivity of IFNγ" relates to the antiviral activity (Billiau, 1996), the induction of the expression of MHC-class-II molecules by macrophages and other cell types (Steinman et al., 1980), the stimulation of the production of inflammatory mediators such as TNFα, IL-1 and NO (Lorsbach et al., 1993), the induction of the expression of adhesion molecules such as ICAM-1 (Dustin et al., 1988) and of important costimulators such as the B7 molecules on professional antigen presenting cells (Freedman et al., 1991), the induction of macrophages to become tumoricidal (Pace et al., 1983), the induction of Ig isotype switching (Snapper and Paul, 1987), any pathological and/or clinical activity during diseases where IFNγ is pathogenic (Billiau, 1996) or any other known bioactivity of IFNγ. In this regard, it should be clear that any assay system demonstrating the IFNγ-neutralizing capacity of a molecule, such as the ones described by Novelli et al. (1991), Lewis (1995) and Turano et al. (1992) can be used. Some of these assays are also described in the subsection Evaluation of anti-IFNγ neutralizing molecules in the Examples section of the present application (see further). It should be noted that the molecules which bind and neutralize IFN-γ as described above neutralize at least one bioactivity, but not necessarily all bioactivities, of IFN-γ.

The present invention further relates to a scFv comprising the humanized variable domain of the monoclonal antibody D9D10. As used herein, the term single-chain Fv, also termed single-chain antibody, refers to engineered antibody constructs prepared by isolating the binding domains (both heavy and light chain) of a binding antibody, and supplying a linking moiety which permits preservation of the binding function. This forms, in essence, a radically abbreviated antibody, having only the variable domain necessary for binding the antigen. Determination and construction of single chain antibodies are described in U.S. Pat. No. 4,946,778 to Ladner et al. and in the Examples section of the present application (see further). The term "humanized" means that at least a portion of the framework regions of an immunoglobulin or engineered antibody construct is derived from human immunoglobulin sequences. It should be clear that any method to humanize antibodies or antibody constructs, as for example by variable domain resurfacing as described by Roguska et al. (1994) or CDR grafting or reshaping as reviewed by Hurle and Gross (1994), can be used. The humanization of the scFv comprising the variable domain of the monoclonal antibody D9D10 is described further in the Examples section of the present application. The monoclonal antibody D9D10 was prepared essentially as described by Sandvig et al. (1987) and Froyen et al. (1993). It should also be noted that the process of humanization of an antibody or antibody construct is regularly accompanied by a significant loss in binding affinity of this antibody or antibody construct (Kettleborough et al., 1991; Park et al., 1996 and Mateo et al., 1997). In contrast, and surprisingly, the constructs humanized by the present inventors were not characterized by a significant loss in binding affinity in comparison to their non-humanized counterparts.

The present invention also relates to a chimeric antibody comprising the humanized variable domain of the monoclonal antibody D9D10. The term "chimeric antibody" refers to an engineered antibody construct comprising variable domains of one species (such as mouse, rat, goat, sheep, cow, llama or camel variable domains), which may be humanized or not, and constant domains of another species (such as non-human primate or human constant domains) (for review see Hurle and Gross (1994)). It should be clear that any method known in the art to develop chimeric antibodies or antibody constructs can be used. The generation of a chimeric antibody comprising the humanized variable domain of the monoclonal antibody D9D10 is described further in the Examples section of the present application.

The present invention also concerns a diabody comprising the humanized variable domain of the monoclonal antibody D9D10. The term "diabody" relates to two non-covalently-linked scFv's, which then form a so-called diabody, as described in detail by Holliger et al. (1993) and reviewed by Poljak (1994). It should be clear that any method to generate diabodies, as for example described by Holliger et al. (1993), Poljak (1994) and Zhu et al. (1996), can be used. The generation of diabodies comprising the variable domain of the monoclonal antibody D9D10 is described further in the Examples section of the present application.

It should also be clear that the scFv's, chimeric antibodies and diabodies described above are not limited to comprise the variable domain of the monoclonal antibody D9D10 but may also comprise variable domains of other anti-IFNγ antibodies, such as the sheep anti-IFNγ antibody described further in the present application, which efficiently neutralize the bioactivity of IFNγ.

Furthermore, the diabodies described above may also comprise two scFv's of different specificities. For example, the latter diabodies may simultaneously neutralize IFN on the one hand and may target another molecule, such as TNF-α, IL-1, IL-2, B7.1 or CD80, B7.2 or CD86, IL-12, IL-4, IL-10, CD40, CD40L, IL-6, tumour growth factor-beta (TGF-β), transferrin receptor, insulin receptor and prostaglandin E2 or any other molecule, on the other hand.

The present invention also concerns multivalent antibodies which bind and neutralize IFNγ. As used herein, the term multivalent antibody refers to any IFNγ-binding and IFNγ-neutralizing molecule which has more than two IFNγ-binding regions. Examples of such multivalent antibodies are triabodies, tetravalent antibodies, peptabodies and hexabodies which bind and neutralize IFNγ and which have three, four, five and six IFNγ-binding regions, respectively.

The present invention thus relates, as indicated above, to triabodies which bind and neutralize IFNγ. As used herein, the term "triabody" relates to trivalent constructs comprising 3 scFv's, and thus comprising 3 variable domains, as described by Kortt et al. (1997) and Iliades et al. (1997). A method to generate triabodies is described by Kortt et al. (1997) and the generation of triabodies comprising the variable domain of the monoclonal antibody D9D10 is described further in the Examples section of the present application. It should be noted that the triabodies of the present invention may comprise: 3 variable domains of 3 different anti-IFNγ Ab's (i.e. 3 anti-IFNγ Ab's which recognize and bind a different epitope on IFNγ [see also above]), 3 variable domains of 3 identical anti-IFNγ Ab's such as 3 variable domains of D9D10 or 3 variable domains of humanized D9D10 or 3 variable domains of sheep anti-IFNγ Ab's or 3 humanized variable domains of sheep anti-IFNγ Ab's, 1 or 2 variable domain(s) of anti-IFNγ Ab's in combination with 2 or 1 variable domain(s) of an Ab which binds to any other molecule than IFNγ, respectively. Examples of such other molecules comprise TNFα, IL-1, IL-2, B7.1 or CD80, B7.2 or CD86, IL-12, IL-4, IL-10, CD40, CD40L, IL-6, tumour growth factor-beta (TGF-β), transferrin receptor, insulin receptor and prostaglandin E2.

The present invention further relates to tetravalent antibodies which bind and neutralize IFNγ. As used herein, the term "tetravalent antibody" refers to engineered antibody constructs comprising 4 antigen-binding regions as described by Pack et al. (1995) and Coloma & Morrison (1997). Methods to generate these tetravalent antibody constructs are also described by the latter authors. The generation of the following 2 different tetravalent antibodies comprising the variable domain of the monoclonal antibody D9D10 are described further in the Examples section of the present application: MoTabI which consists of 4 identical humanized D9D10 scFv's in the format of a homodimer of two identical molecules each containing two D9D10 scFv's which are linked together using a dimerization domain; the latter domain also drives the homodimerization of the molecule, and, MoTab II which consists of a full-size humanized D9D10 molecule to which two humanized D9D10 scFv's are attached at the carboxyterminus (CH3-domain). It should be noted that the tetravalent antibodies of the present invention may comprise: 4 variable domains of 4 different anti-IFNγ Ab's (i.e. anti-IFNγ Ab's which recognize and bind to a different epitope on IFNγ), 4 variable domains of 4 identical anti-IFNγ Ab's such as 4 variable domains of D9D10 or 4 variable domains of humanized D9D10 or 4 variable domains of sheep anti-IFNγ Ab's or 4 humanized variable domains of sheep anti-IFNγ Ab's, 2 variable domain(s) of one anti-IFNγ Ab in combination with 2 variable domain(s) of another anti-IFNγ Ab, 2 variable domain(s) of anti-IFNγ Ab's in combination with 2 variable domain(s) which binds to any other molecule than IFNγ. Examples of such other molecules comprise TNFα, IL-1, IL-2, B7.1 or CD80, B7.2 or CD86, IL-12, IL-4, IL-10, CD40, CD40L, IL-6, TGF-β, transferrin receptor, insulin receptor and prostaglandin E2.

Furthermore, the term "dimerization domain" of MoTab I refers to any molecule known in the art which is capable of coupling the two identical molecules. Examples of such domains are the leucine zipper domain (de Kruif & Logtenberg, 1996), the helix-turn-helix motif described by Pack et al. (1993), the max-interacting proteins and related molecules as described in U.S. Pat. No. 5,512,473 to Brent & Zervos and the polyglutamic acid-polylysine domains as described in U.S. Pat. No. 5,582,996 to Curtis.

The present invention thus relates, as indicated above, to peptabodies and hexabodies which bind and neutralize IFNγ.

As used herein, the term "peptabodies" relates to pentavalent constructs as described in detail by Terskikh et al. (1997). The term "hexabodies" relates to hexavalent constructs which are similar to the pentavalent constructs as described in detail by Terskikh et al. (1997) but wherein the pentamerization domain is replaced by any hexamerization domain known in the art. A method to generate peptabodies is also described by Terskikh et al. (1997) and a method to generate hexabodies can be derived from the description by the latter authors. It should be noted that the peptabodies and hexabodies of the present invention may comprise: 5 (relating to the peptabodies) or 6 (relating to the hexabodies) variable domains of 5 or 6 different anti-IFNγ Ab's (i.e. 5 or 6 anti-IFNγ Ab's which recognize and bind a different epitope on IFNγ [see also above]), 5 or 6 variable domains of identical anti-IFNγ Ab's such as 5 or 6 variable domains of D9D10, or, 5 or 6 variable domains of humanized D9D10, or, 5 or 6 variable domains of sheep anti-IFNγ Ab's, or, 5 or 6 humanized variable domains of sheep anti-IFNγ Ab's, less than 5 or 6 variable domain(s) of any anti-IFNγ Ab's in combination with less than 5 or 6 variable domain(s) of an Ab which binds to any other molecule than IFNγ, respectively. Examples of such other molecules comprise TNFα, IL-1, IL-2, B7.1 or CD80, B7.2 or CD86, IL-7.2, IL-4, IL-10, CD40, CD40L, IL-6, TGF-β, transferrin receptor, insulin receptor and prostaglandin E2.

The present in invention further relates to ruminant antibodies which bind and neutralize IFNγ. The term "ruminant" relates to animals belonging to the suborder Ruminantia of even-toed hoofed mammals (as sheep, goats, cows, giraffes, deer, llama, vicunas and camels) that chew the cud and have a complex 3- or 4-chambered stomach.

More specifically, the present invention relates to sheep antibodies which bind and neutralize IFNγ. The term "sheep" relates to any of numerous ruminant mammals belonging to the genus Ovis. The generation of sheep anti-IFNγ antibodies is described in the Examples section of the present application. The present invention also relates to sheep monoclonal antibodies. As used herein, the term "monoclonal antibody" refers to an antibody composition having a homogeneous antibody population. The term is not limited regarding the species or source of the antibody, nor is it intended to be limited by the manner in which it is made. Indeed, the monoclonal sheep antibodies of the present invention can be generated by any method known in the art. It should be noted that also humanized antibodies, scFv's or any other fragment thereof which has largely retained the specificity of said sheep antibody or sheep monoclonal antibody are covered by the present invention. As used herein, the term "fragment" refers to F(ab), F(ab')2, Fv, and other fragments which retain the antigen binding function and specificity of the parent antibody. It should also be understood that the variable domains of the sheep anti-IFNγ (monoclonal) antibodies or scFv of the sheep anti-IFNγ (monoclonal) antibodies may be part of the chimeric antibodies, diabodies, triabodies, tetravalent antibodies, peptabodies and hexabodies as described above.

The present invention further relates to scFv's, chimeric antibodies, diabodies, triabodies, tetravalent antibodies, peptabodies, hexabodies and sheep antibodies which bind and neutralize IFNγ and which are produced by the methods as described above and in the Examples section of the present application.

The present invention further relates to a composition comprising scFv's and/or chimeric antibodies and/or diabodies and/or triabodies and/or tetravalent antibodies and/or peptabodies and/or hexabodies and/or sheep antibodies which bind and neutralize IFNγ in a pharmaceutically acceptable excipient, possibly in combination with other drugs or other antibodies, antibody derivatives or constructs for use as a medicament to prevent or treat septic shock, cachexia, immune diseases such as multiple sclerosis and Crohn's disease and skin disorders such as bullous, inflammatory and neoplastic dermatoses. Examples of such other drugs or other antibodies, antibody derivatives or constructs are, with regard to septic shock: an isotonic crystalloid solution such as saline, dopamine, adrenaline and antibiotics; with regard to cachexia: anti-TNF-alpha antibodies; with regard to multiple sclerosis: ACTH and corticosteroids, interferon beta-1b (Betaseron), interferon beta-1a (Avonex), immunosuppressive drugs such as azathioprine, methotrexate, cyclophosphamide, cyclosporin A and cladribine (2-CdA), copolymer 1 (composed of 4 amino acids common to myelin basic proteins), myelin antigens, roquinimex A, the mAb CAMPATH-1H and potassium channel blockers; with regard to Crohn's disease: sulfasalazine, corticosteroids, 6 mercaptopurine/azathioprine and cyclosporin A; with regard to psoriasis: cyclosporin A, methotrexate, calcipotriene (Dovonex), zidovudine (Retrovir), histamine2 receptor antagonists such as ranitidine (Zantac) and cimetidine (Tagamet), propylthiouracil, acitretin (Soriatane), fumaric acid, vitamin D derivates, tazarotene (Tazorac), IL-2 fusion toxin, tacrolimus (Prograf), CTLA4Ig, anti-CD4 mAb's and T-cell receptor peptide vaccines. It should also be clear that any possible mixture of the above-indicated IFN-γ-binding molecules may be part of the above-indicated pharmaceutical composition.

As used herein, the term "composition" refers to any composition comprising as an active ingredient scFv's and/or chimeric antibodies and/or diabodies and/or triabodies and/or tetravalent antibodies and/or peptabodies and/or hexabodies and/or sheep antibodies which bind and neutralize IFNγ according to the present invention possibly in the presence of suitable excipients known to the skilled man. The scFv's and/or chimeric antibodies and/or diabodies and/or triabodies and/or tetravalent antibodies and/or peptabodies and/or hexabodies and/or sheep antibodies which bind and neutralize IFNγ of the invention may thus be administered in the form of any suitable composition as detailed below by any suitable method of administration within the knowledge of a skilled man. The preferred route of administration is parenterally. In parenteral administration, the compositions of this invention will be formulated in a unit dosage injectable form such as a solution, suspension or emulsion, in association with a pharmaceutically acceptable excipient. Such excipients are inherently nontoxic and nontherapeutic. Examples of such excipients are saline, Ringer's solution, dextrose solution and Hank's solution. Nonaqueous excipients such as fixed oils and ethyl oleate may also be used. A preferred excipient is 5% dextrose in saline. The excipient may contain minor amounts of additives such as substances that enhance isotonicity and chemical stability, including buffers and preservatives.

The scFv's and/or chimeric antibodies and/or diabodies and/or triabodies and/or tetravalent antibodies and/or peptabodies and/or hexabodies and/or sheep antibodies which bind and neutralize IFNγ of the invention are administered at a concentration that is therapeutically effective to treat or prevent septic shock, cachexia, immune diseases such as multiple sclerosis and Crohn's disease and skin disorders such as bullous, inflammatory and neoplastic dermatoses. The dosage and mode of administration will depend on the individual. Generally, the compositions are administered so that the scFv's and/or chimeric antibodies and/or diabodies and/or triabodies and/or tetravalent antibodies and/or peptabodies and/or hexabodies and/or sheep antibodies which bind and neutralize IFNγ are given at a dose between 1 μg/kg and 10 mg/kg, more preferably between 10 μg/kg and 5 mg/kg, most preferably between 0.1 and 2 mg/kg for each IFN-γ-binding molecule. Preferably, they are given as a bolus dose. Continuous short time infusion (during 30 minutes) may also be used. If so, the scFv's and/or chimeric antibodies and/or diabodies and/or triabodies and/or tetravalent antibodies and/or peptabodies and/or hexabodies and/or sheep antibodies which bind and neutralize IFNγ or compositions comprising the same may be infused at a dose between 5 and 20 μg/kg/minute, more preferably between 7 and 15 μg/kg/minute (for each IFN-γ-binding molecule).

According to the specific case, the "therapeutically effective amount" of a scFv's and/or chimeric antibodies and/or diabodies and/or triabodies and/or tetravalent antibodies and/or peptabodies and/or hexabodies and/or sheep antibodies which bind and neutralize IFNγ needed should be determined as being the amount sufficient to cure the patient in need of treatment or at least to partially arrest the disease and its complications. Amounts effective for such use will depend on the severity of the disease and the general state of the patient's health. Single or multiple administrations may be required depending on the dosage and frequency as required and tolerated by the patient.

The present invention further relates to scFv's and/or chimeric antibodies and/or diabodies and/or triabodies and/or tetravalent antibodies and/or peptabodies and/or hexabodies and/or sheep antibodies which bind and neutralize IFNγ for determining IFNγ levels in a biological sample, comprising:

1) contacting the biological sample to be analysed for the presence of IFNγ with a scFv and/or chimeric antibody and/or diabody and/or triabody and/or tetravalent antibody and/or peptabodies and/or hexabodies and/or sheep antibody as defined above, 2) detecting the immunological complex formed between IFNγ and said scFv and/or chimeric antibody and/or diabody and/or triabody and/or tetravalent antibody and/or peptabodies and/or hexabodies and/or sheep antibody.

As used herein, the term "a method to detect" refers to any immunoassay known in the art such as assays which utilize biotin and avidin or streptavidin, ELISA's and immunoprecipitation, immunohistochemical techniques and agglutination assays. A detailed description of these assays is given in WO 96/13590 to Maertens & Stuyver. The immunohistochemical detection of IFNγ in cryosections of spinal cord and brain of non-human primates suffering from experimental autoimmune encephalomyelitis is described in detail in the Examples section of the present application. The term "biological sample" relates to any possible sample taken from a mammal including humans, such as blood (which also encompasses serum and plasma samples), sputum, cerebrospinal fluid, urine, lymph or any possible histological section, wherein IFNγ might be present.

The present invention will now be illustrated by reference to the following examples which set forth particularly advantageous embodiments. However, it should be noted that these embodiments are illustrative and are not to be construed as restricting the invention in any way.

EXAMPLES

1. Generation of Humanized scFvD9D10

As the use of mouse monoclonals in humans induces a HAMA response, a humanized antibody or antibody derivative is the alternative. Humanized scFvD9D10 need to have similar binding and neutralization properties as their original mouse counterparts, but will elicit hardly any immune response in humans as compared to the parent mouse scFv.

1.1. Modelling

We used computer modelling techniques for the construction of a humanized scFvD9D10 in order to develop an active scFv with retained structure and affinity. The as humanized using a resurfacing strategy which includes the replacement of 'non-human' residues without significant structural changes of the scFv molecule. This work consisted of 2 main parts. In the first part, a 3D-structure of the mouse scFv was constructed. For this purpose, we have homology-modeled D9D10 using Ig $V_L$ and $V_H$ domains with a similar sequence and a known structure. In the second part (the actual humanization step), we have aligned D9D10 with similar human sequences to identify 'typically human residues'. After verifying their structural compatibility with the D9D10 model, they have been proposed as residues-to-be-humanized.

Part 1: 3D-structure of scFvD9D10

Identification of Known Structures with the Most Resembling Sequence

Different BLAST-searches were performed by entering the D9D10 sequence of either $V_K$ or $V_H$, by using the 'BLASTP' search program and by selecting the Brookhaven Protein Data Bank as the database to be searched. This search was performed 4 times, namely for $V_K$ with and without CDR-loops and for VH with and without CDR-loops. The obtained data are summarized in Table 1.

TABLE 1

Summary of BLAST-search results

A) BLAST-search using D9D10-$V_K$ sequence

| rank | PDB Code | score + CDR ident./sim. | score − CDR ident./sim. | rank for $V_H$ | source | I. D. |
|---|---|---|---|---|---|---|
| 1 | 1BAF | 87%/92% | 90%/95% | >50 | mouse | Fab frag. mAb An02 compl. w. its hapten (2,2,6,6-Tetramethyl-1-Piperidinyloxy-Dinitrophenyl) |
| 2 | 1FOR | 80%/90% | 85%/93% | 16 | mouse | Igg2a Fab frag. (Fab17-Ia) |
| 3 | 2IFF | 78%/86% | 84%/90% | 15 | mouse | Igg1 Fab Frag. (Hyhel-5) compl. w. Chicken Lysozyme mutant R68K |
| 4 | 1FIG | 75%/86% | 80%/90% | 28 | mouse | Chain L, Immunogl G1 (Kappa Light Chain) Fab' frag, Mouse |

TABLE 1-continued

Summary of BLAST-search results

| | | | | | | |
|---|---|---|---|---|---|---|
| 5 | 1FVB | 80%/87% | 83%/89% | >50 | mouse | IgA Fv frag. (Anti-Alpha(1->6) Dextran) (Theoret. Model) |
| 6 | 2HFL | 77%/85% | 83%/89% | 14 | mouse | IgG1 Fab frag. (HyHEL-5) compl. w. Chicken Lysozyme |
| — | — | — | — | — | — | — |
| 19 | 1NCA | 60%/73% | 70%/84% | 1 | mouse | N9 neuraminidase-NC41 compl. w. Influenza Virus |
| — | — | — | — | — | — | — |

B) BLAST-search using D9D10-$V_H$ sequence

| rank | PDB Code | score + CDR ident./sim. | score – CDR ident./sim. | rank for $V_K$ | source | I. D. |
|---|---|---|---|---|---|---|
| 1 | 1NCA | 83%/89% | 91%/95% | 19 | mouse? | N9 neuraminidase-NC41 compl. w. Influenza Virus |
| 2 | 1NCB | 80%/88% | 87%/94% | >50 | mouse? | N9 Neuraminidase-Nc41 Mut. N329D compl. w. Fab, Influenza Virus |
| 3 | 1TET | 80%/86% | 87%/92% | 38 | mouse | Igg1 Monocl. Fab frag (Te33) compl. w. Cholera Toxin Peptide 3 |
| 4 | 1DBA | 80%/87% | 86%/92% | >50 | mouse | Fab' frag. of the Db3 Anti-Steroid Monocl. Ab |
| — | — | — | — | — | — | — |
| 16 | 1FOR | 58%/76% | 63%/83% | 2 | mouse | Igg2a Fab frag. (Fab17-Ia) |
| — | — | — | — | — | — | — |

A sequence similarity of more than 70% guarantees a strong structural similarity. For $V_K$, at least 6 very good matching structures (all murine proteins) could be identified: 1BAF, 1FOR, 2IFF, 1FIG, 1FVB and 2HFL. The scores for the search with CDR-loops varied from 87% to 77% for identical residues, and from 92% to 85% for chemically similar residues. The scores for the search without CDR-loops ranged from 90% to 83% identical residues and from 95% to 89% similar residues. The small difference in homology between the searches with and without CDR-loops suggests that even some of the CDR-loops are structurally similar. For $V_H$, analogous results were obtained. Four very well matching structures could be identified: 1NCA, 1NCB, 1TET and 1DBA with scores varying from 83% to 80% identical residues and from 89% to 87% similar residues when CDR-loops are included. If CDR-loops were not taken into account, significantly higher scores were obtained: from 91% to 86% for identical residues and 95% to 92% for similar residues. The latter was due to the fact that CDR-H3 from D9D10 was not matching well with any sequence.

Three-dimensional Fitting of the Best Candidates

From these scores, it was clear that the $V_K$-fragment from 1FOR resembled very well $V_K$ from D9D10 (rank nr 2). A reasonably well homology was also found for its $V_H$ counterpart (rank nr 16). For the heavy domain, 1NCA had a very high score for $V_H$ (rank nr 1) and an acceptable score for its $V_K$-domain (rank nr 19). Since the β-barrels of Fv fragments are well conserved, and since for both $V_K$ and $V_H$ we dispose of two very good resembling fragments with fairly well matching counterparts, we had enough information to start the construction of the D9D10 model.

When superimposing (fitting) the complete main chain of 1FOR and 1NCA we obtained a root-mean-square (rms) deviation of 1.1 Å (values around or less than 1 Å indicate a strong structural similarity). Fitting on $V_K$ alone gave 1.0 Å and on $V_H$ we obtained 0.8 Å. This means that both the complete structures and the separate V-domains are nearly identical. In order to obtain an even smaller rms-deviation, we fitted all β-stands of the central β-barrel, giving an rms-deviation of 0.52 Å. When the C-terminal strands and certain diverging residues were not taken into account, an rms-deviation as low as 0.37 Å was obtained. The high structural resemblance of the central β-barrel of both 1FOR and 1NCA ensures us that we have correctly positioned the two domains relative to each other.

In the next step, only the $V_K$ fragment of 1FOR and the $V_H$ of 1NCA were retained and CDR-loops of 1FOR and 1NCA were adopted without further modeling.

Modeling of the D9D10 Sequence onto the Constructed Framework

When the sequences of D9D10 were compared with those of 1FOR-$V_K$ and 1NCA-$V_H$, 21 and 20 mutations were necessary to mutate 1FOR and 1NCA into D9D10, respectively. These mutations were done simultaneously using the Dead-End Elimination method (Desmet et al., 1992) which found the globally best conformation for all 41 mutations. For both $V_K$ and $V_H$, the mutations could be done without inducing sterical or energetical conflicts. As a consequence, we have obtained a very reliable 3D-model for the variable domains of D9D10 (except for CDR-H3).

PART 2: Humanization of D9D10

Identification of Residues to be Humanized

In order to identify typical D9D10 'murine' residues, $V_K$ and $V_H$ sequences were again subjected to a BLASTP-search, but this time the entire 'non-redundant Genbank' database (PDB+SwissProt+SPupdate+PIR) was searched for similar sequences. Out of the resulting matches, only human and humanized sequences were retained and aligned with D9D10.

The alignment revealed several systematic differences in sequence between the murine D9D10 molecule and the best matching human $V_K$ and $V_H$ fragments. From this comparison, we have derived a consensus list of human residues.

Each of these residues was then placed onto the D9D10 model and the following properties were examined: (i) the compatibility with the framework and with neighboring residues, (ii) the solvent accessibility and (iii) the proximity to the CDR-loops. In general, only D9D10 residues which were not found in any human sequence, which were structurally compatible with the D9D10 framework (and CDR's), and which were clearly solvent exposed, were selected for humanization.

For the $V_K$ domain we proposed 8 mutations, which were spatially clustered into 2 surface patches of 3 residues each plus two isolated residues. For the $V_H$ domain we pinpointed 9 residues to be humanized. The latter residues formed a surface cluster of 5 residues, one of 2 residues and 2 additional isolated residues. For neither of the two domains, buried residues were retained in the mutation list. The reason for this is that we explicitly wanted to preserve the D9D10 framework structure and, also, that buried residues are not 'visible' to the immune system anyway.

Finally, the side-chain conformation of the 8+9 mutations was modeled using the Dead-End Elimination algorithm. We found that all mutations were energetically favorable. This strengthened the hypothesis that the humanization procedure would not affect the antigen binding properties of D9D10.

1.2. Construction, Expression, Purification and Evaluation of Humanized scFvD9D10

Eight substitutions in $V_H$D9D10 and 9 in $V_L$D9D10 had to be carried out as shown in FIG. 2. Since the different mutations were spread among the whole $V_H$ and $V_L$ sequences, it was decided to assemble the whole $V_H$ and $V_L$ sequences out of synthetic oligonucleotides, hereby including all necessary substitutions during the oligonucleotide synthesis as an alternative to mutagenesis. During the oligonucleotide synthesis, non-optimal E. coli codons were substituted for more optimal ones coding for the same amino acid. Both $V_H$ and $V_L$ regions were assembled separately according to the PCR assembly method described by Stemmer et al. (1995). The assembled $V_H$ and $V_L$ regions were first subcloned in pGEM-T vectors ( PROMEGA Corp., Madison Wis. US) and their correct sequence was confirmed by DNA sequencing. Both humanised regions were subsequently introduced into the pscFvD9D10H6 expression vector (Froyen et al., 1993). For the assembly of the heavy chain, we synthesized 18 oligo's, 40 nucleotides in length, which collectively encode both strands of the $V_H$ region from the AlwNI site to the StyI site. The plus strand as well as the minus strand consist of 9 oligo's configured in such a way that, upon assembly, complimentary oligo's will overlap by 20 nucleotides. In these oligo's we included mutations both leading to "humanised" amino acids at the predetermined sites and to "optimised" E. coli codons.

| Oligo No. | Oligo Seq. | |
|---|---|---|
| 1s | 5'-CGCGCAGCCGCTGGATTGTTATTACTCGCTGCCCAACCAG-3' | (SEQ ID NO 3) |
| 2as | 5'-CAGCTGCACCTGGGCCATCGCTGGTTGGGCAGCGAGTAAT-3' | (SEQ ID NO 4) |
| 3s | 5'-CGATGGCCCAGGTGCAGCTGGTGCAGAGCGGTAGCGAACT-3' | (SEQ ID NO 5) |
| 4as | 5'-CGCTCGCACCCGGTTTTTTCAQTTCGCTACCGCTCTGCAC-3' | (SEQ ID NO 6) |
| 5s | 5'-GAAAAAACCGQGTGCGAGCGTTAAGATCAGCTGCAAAGCG-3' | (SEQ ID N0 7) |
| 6as | 5'-TCGGTGAAGGTATAACCGCTCGCTTTGCAGCTGATCTTAA-3' | (SEQ ID NO 8) |
| 7s | 5'-AGCGGTTATACCTTCACCGATTACGGTATGAACTGGGTTA-3' | (SEQ ID NO 9) |
| 8as | 5'-ACCTTGACCCGGCGCCTGTTTAACCCAGTTCATACCGTAA-3' | (SEQ ID NO 10) |
| 9s | 5'-AACAGGCGCCGGGTCAAGGTCTGAAATGGATGGGTTGGAT-3' | (SEQ ID NO 11) |
| 10as | 5'-TTTCACCGGTGTAGGTGTTGATCCAACCCATCCATTTCAG-3' | (SEQ ID NO 12) |
| 11s | 5'-CAACACCTACACCGGTGAAAGCACCTACGTTGACGATTTC-3' | (SEQ ID NO 13) |
| 12as | 5'-CTGAAAACGAAACGACCTTTGAAATCGTCAACGTAGGTGC-3' | (SEQ ID NO 14) |
| 13s | 5'-AAAGGTCGTTTCGTTTTCAGCCTGGATACCAGCGTTAGCG-3' | (SEQ ID NO 15) |
| 14as | 5'-GCTGATCTGCAGGTAQGCCGCQCTAACGCTGGTATCCAGG-3' | (SEQ ID NO 16) |
| 15s | 5'-CGGCCTACCTGCAGATCAGCTCTCTGAAAGCGGAAGACAC-3' | (SEQ ID NO 17) |
| 16as | 5'-GCGCGCAGAAGTAGGTCGCGGTGTCTTCCGCTTTCAGAGA-3' | (SEQ ID NO 18) |
| 17s | 5'-CGCGACCTACTTCTGCGCGCGTCGCGGTTTCTACGCGATG-3' | (SEQ ID NO 19) |
| 18as | 5'-GCGCCCTTGGCCCCAGTAATCCATCGCGTAGAAACCGCGAC-3' | (SEQ ID NO 20) |

After assembly of the 18 40-mer oligonucleotides, the desired fragment was PCR amplified using 2 oligonucleotides complementary to the 5' and 3' end of the fragment respectively.

| Oligo No. | Oligo Seq. |
|---|---|
| 1s | 5'-CGCGCAGCCGCTGGATTGTTATTAC-3' (SEQ ID NO 21) |

-continued

| Oligo No. | Oligo Seq. | |
|---|---|---|
| 2as | 5'-GCGCCCTTGGCCCCAGTAATC-3' | (SEQ ID NO 22) |

The resulting 381 bp fragment was cloned into a pGEM-T vector, resulting in pGEM-TV$_H$H and several clones were sequenced. A similar approach was followed for the light chain. Hereby 14 oligos were synthesized, 2 48-mers and 12 40-mers, which collectively encode both strands of the V$_L$ region from the SacI site to the XhoI site. However, since the SacI site was present exactly on an amino acid substitution site, this restriction site could not be retained in the synthetic V$_L$ gene. As an alternative, a Bst1107I site was created which will, after ligation with the blunted SacI site, restore the exact V$_L$ reading frame.

process, cycling with Taq DNA polymerase resulted in the formation of increasingly larger DNA fragments until the full-length gene was obtained. It can be noted that DNA ligase has not been used in the process. After assembly, the desired fragments were amplified using 5' and 3' end complementary primers. The resulting fragments were subsequently cloned into a suitable cloning vector such as pGEM-T, giving pGEM-TV$_L$H and pGEM-TV$_H$H. The final vector, pscFvD9D10V$_{Hum}$, was constructed by ligating a 310 bp Bst1107/XhoI fragment originating from vector pGEM-TV$_L$H with a 3180 bp SacIblunt/XhoI fragment

| Oligo No. | Oligo Seq. | |
|---|---|---|
| 1s | 5'-GCGGTATACTGACCCAGAGCCCGGCGACCATGAGCGCGAGCCCGGGT-3' | (SEQ ID NO 23) |
| 2as | 5'-CAGGTCAGGGTAACACGTTCACCCGGGCTCGCGCTCATGG-3' | (SEQ ID NO 24) |
| 3s | 5'-GAACGTGTTACCCTGACCTGCAGCGCGAGCTCTAGCATCA-3' | (SEQ ID NO 25) |
| 4as | 5'-ATGATACCAGAACATATAGCTGATGCTAGAGCTCGCGCTG-3' | (SEQ ID NO 26) |
| 5s | 5'-GCTATATGTTCTGGTATCATCAGCGTCCGGGTCAGAGCCC-3' | (SEQ ID NO 27) |
| 6as | 5'-TATCATAGATCAACAGACGCGGGCTCTGACCCGGACGCTG-3' | (SEQ ID NO 28) |
| 7s | 5'-GCGTCTGTTGATCTATGATACCAGCAACCTGGCGAGCGGT-3' | (SEQ ID NO 29) |
| 8as | 5'-CCGCTGAAACGCGCCGGAACACCGCTCGCCAGGTTGCTGG-3' | (SEQ ID NO 30) |
| 9s | 5'-GTTCCGGCGCGTTTCAGCGGTAGCGGTAGCGGTACCAGCT-3' | (SEQ ID NO 31) |
| 10as | 5'-ACGGCTGATGGTCAGGCTATAGCTGGTACCGCTACCGCTA-3' | (SEQ ID NO 32) |
| 11s | 5'-ATAGCCTGACCATCAGCCGTATGGAACCGGAAGATTTCGC-3' | (SEQ ID NO 33) |
| 12as | 5'-TCTGATGGCAGAAATAGGTCGCGAAATCTTCCGGTTCCAT-3' | (SEQ ID NO 34) |
| 13s | 5'-GACCTATTTCTGCCATCAGAGCTCTAGCTATCCGTTCACC-3' | (SEQ ID NO 35) |
| 14as | 5'-CGCGCTCGAGTTTGGTACCCTGACCGAAGGTGAACGGATAGCTAGAGC-3' | (SEQ ID NO 36) |

After assembly of the 2 48-mer and 12 40-mer oligonucleotides, the desired fragment was again PCR amplified using 2 oligonucleotides complementary to the 5' and 3' end of the fragment respectively.

| Oligo No. | Oligo Seq. | |
|---|---|---|
| 1s | 5'-CGCGGTATACTGACCCAGAGC-3' | (SEQ ID NO 37) |
| 2as | 5'-CGCGCTCGAGTTTGGTACCCTG-3' | (SEQ ID NO 38) |

The resulting 316 bp fragment was cloned into a pGEM-T vector, resulting in pGEM-TV$_L$H and several clones were sequenced. The assembly PCR protocol (Stemmer et al., 1995) consisted of 3 steps: gene assembly, gene amplification and cloning. Since single-stranded ends of complementary DNA fragments were filled-in during the gene assembly originating from vector pscFvD9D10H6V$_H$H (=pscFvD9D10H6 in which V$_H$ was replaced by the humanized V$_H$ obtained from pGEM-TV$_H$H).

Induction of the humanised scFv D9D10 was carried out in E. coli strain JM83. Detection of His6-tagged scFv's on western blot was done with an anti D9D10 rabbit polyclonal antibody and an anti His6 monoclonal antibody (Babco, Richmond, Calif., USA). Compared to the non-humanized scFvD9D10 (Froyen et al., 1993), the humanized scFvD9D10 was expressed at approximately 3–5 times higher levels (30–40 mg/l). This increase in expression level can be due to the fact that during assembly the humanized scFvD9D10 coding sequence was codon-optimised for E. coli expression. Alternatively, one or several of the humanized amino acids can have a beneficial effect on the expression level; or the increase in expression level can be caused by a combination of the two. As with the non-humanized scFv, most of the expressed protein was still present intracellularly (70–80%), with 5–10% present in the periplasmic fraction and 10–20% secreted to the medium.

The cells were harvested and lysed in the presence of protease inhibitors at 4° C. by the French press (2 passages at 14.000 psi). The cell lysate was clarified by centrifugation and the supernatant was used for purification. The supernatant was loaded on $Zn^{2+}$-IDA Sepharose FF and the resin was washed by applying an imidazole step gradient. The different pools were analysed by SDS-PAGE under reducing and non reducing conditions.

The humanized scFv bound and eluted as expected in the 150 mM imidazole elution pool and SDS-PAGE showed that the recovered scFv was >90% pure in a single step. The shift in relative migration under reducing conditions showed that the scFv was purified in an oxidized form. However, in contrast to the mouse scFv, the humanized scFv showed a high tendency for non specific adsorption, because only 40–50% of the initial product was recovered after dialysis.

The humanized scFvD9D10 was shown to have the same biological activity as the mouse scFvD9D10 for neutralizing the antiviral activity of human IFNγ (described in example 7).

Affinity could be calculated for murine and humanized scFv using Surface Plasmon Resonance(SPR)-analysis with the BIACORE® (Biacore AB, Uppsala, Sweden). This technology permits real-time mass measurements using surface plasmon resonance. SPR is an optical phenomenon, seen as a sharp dip in the intensity of light reflected from a thin metal film coated onto a glass support. The position of this dip depends on the concentration of solutes close to the metal surface. In general, a protein (e.g. antibody) is coupled to the dextran layer (covering the gold film) of a sensor chip and solutions containing different concentrations of a binding protein (e.g. antigen) are allowed to flow across the chip. Binding (association and dissociation) is monitored with mass sensitive detection.

In order to determine the affinity of the D9D10 derivatives for hIFNγ, BIACORE® experiments were performed in which the murine D9D10 was immobilized onto a CM5 sensorchip (Biacore AB). D9D10 was immobilized using amine coupling according to the manufacturer's procedure. To decrease the non specific interaction of human IFNγ with the carboxylic groups of the dextran layer, the sensorchip was pretreated with 4 cycles of EDC/NHS—thus reducing the amount of unblocked carboxylic groups remaining on the sensor surface—before immobilizing D9D10. Then, immobilization of D9D10 was carried out using a continuous flow of 5 l/min on a sensor chip surface initially activated with 17 l of an 0.05M NHS/ 0.2M EDC mixture. 35 L of typically 3 g/ml D9D10 was injected over the activated surface. Residual unreacted ester groups were blocked by injecting 17 l of 0.1M ethanolamine pH 8.5. D9D10 was immobilised directly on a CM5 chip at an optimal concentration of 3 g/ml in an acetate buffer pH 5.4 resulting in an immobilization level of about 600 RU. Most accurate affinity data were obtained by injecting human IFNγ and monitoring the subsequent binding of scFvD9D10; the latter interacting with remaining free epitopes on human IFNγ. On and off rates were calculated using the BIAevaluation software (Biacore AB).

Results of a typical experiment are shown in FIG. 3 for murine scFvD9D10 and in FIG. 4 for humanized scFvD9D10 (These data were generated in separate experiments). Calculated data were in good agreement. As off rates were hardly detectable for both constructs in most experiments, only on rates are shown for the concentrations tested. These data clearly indicated that the humanization did not hamper the binding characteristics of the scFv fragment.

Monoclonal antibodies were generated against the humanized scFvD9D10. A female BALB/c mouse was immunized (injected intraperitoneally) 3 times with humanized scFvD9D10 (i.e., at days 0 (50 μg), 32(25 μg) and 56(25 μg)). Three months after, a final boost of 25 μg was given. Three days after this last injection, spleen cells were retrieved from the immunized mouse and used for cell fusion. Dissociated splenocytes from the immunized mouse were fused with murine myeloma cells SP2/0-Ag14 (ATCC, CRL-1581) at a ratio of 10:3 using a polyethylene glycol/DMSO solution mainly according the procedure as described by Köhler and Milstein (1975). The fused cells were mixed up and resuspended in DMEM medium supplemented with hypoxanthine, sodium pyruvate, glutamine, a non-essential amino acid solution, 20% heat-inactivated fetalclone (Hyclone Lab., Utah) and 10% BM-Condimed (Boehringer Mannheim). The cells were then distributed to 96 well plates to which aminopterin was added 24 hours after the cell fusion. Each well contained between 1 to 5 growing hybridoma clones at the average. After 8 days supernatant of the wells was collected and screened in an ELISA for binding to humanized scFvD9D10. The antibodies of the hybridomas thus generated were further tested for their binding capacity to murine and humanized scFvD9D10 and human IgG. Certain monoclonal antibodies derived from this hyper immune mouse did recognize not only humanized scFvD9D10 but also human IgG, indicating the quality of the humanization strategy. Using the antibodies which specifically interact with humanized scFvD9D10 (1D5C5; 11E2G6; 10F12A2 available at Innogenetics N.V., Industriepark Zwijnaarde 7, Box 4, B-9052 Ghent, Belgium) and do not cross react with the yet tested human IgG preparations, an ELISA is generated for detecting and quantifying D9D10 derived constructs in human and primate serum.

Immunization experiments in rabbit and mouse with his-tagged proteins including the humanized scFvD9D10 revealed weak to fairly high immunogenic responses of the his tail. Consequently, we made a new construct and removed the C-terminal hexahistidinetag from the scFvD9D10 (humanized scFvD9D10 $H6^-$). This was done by cutting vector pscFvD9D10$V_{Hum}$ with XhoI and EcoRI and substituting the His6-tail with a tandem stop codon and a unique NcoI site for easy identification. This was accomplished using two synthetic oligo's (oligo 1:5'-TCGAGATCAAACGGTAATAGCCATGG-3' (SEQ ID NO 39); oligo 2:5'-AATTCCATGGCTATTACCGTTTGATC-3' (SEQ ID NO 40)) which, when annealed, reconstitute the D9D10 $V_L$ coding sequence, followed by tandem stop codons and a unique NcoI site for identification. The annealed double-stranded oligo has sticky ends corresponding to a XhoI site at the 5' end and EcoRI site at the 3' end. The oligo was ligated into the XhoI/EcoRI opened pscFvD9D10$V_{Hum}$ vector resulting in pscFvD9D10$V_{Hum}$ [$H6^-$]. Expression analysis showed identical expression levels and localisation compared to the His6-tagged D9D10 in *E. coli*.

2. Generation of Humanized, Chimeric D9D10

Two fusion cDNA-genes respectively coding for the heavy and light chain fusion-proteins of the humanized D9D10 whole antibody were constructed. The light chain fusion cDNA consists of the cDNA encoding the mouse D9D10 light chain leader sequence (Ldr), needed for efficient transport of the fusion protein in the host cell, the humanized D9D10 light chain variable domain cDNA($V_{Lh}$), followed by a human immunoglobulin kappa-light chain constant domain ($C_L$).

The heavy chain fusion cDNA consists of the mouse D9D10 light chain leader cDNA-sequence (Ldr), followed by the humanized D9D10 heavy chain variable domain cDNA ($V_{Hh}$) and a human IgG1 heavy chain constant domain ($C_H$=$C_H$1-Hinge-$C_H$2-$C_H$3) cDNA, in which the C1q-complement binding site in the $C_H$2 region, known to induce complement activation upon injection of the recombinant antibody, was mutated (Pro$_{331}$→Ser) (Xu et al., 1994).

PCR Cloning of Human Immunoglobulin Cγ1 and $C_K$ cDNA

Total RNA was isolated from human tonsil cells (frozen pellet of ±$10^7$ cells) following the Chomczynski GuSCN/acid phenol isolation method (Chomczynski and Sacchi, 1987). 140 μg total RNA was obtained. cDNA was prepared by annealing 700 ng total RNA to 300 ng random hexamers (Pharmacia, Upsala, Sweden) and reverse transcription for 90 min at 42° C. using AMV reverse transcriptase (RT-Stratagene) in a final volume of 20 μl (50 mM Tris pH 8.3, 40 mM KCl, 6 mM MgCl2, 5 mM DTT). The reaction was inactivated by heating at 90° C. for 15 min.

Cloning of the Human CK cDNA:

The cDNA was used as template for PCR amplification of the human $C_K$ cDNA using primer sequences based on the Genbank database sequence , accession # V00557 and # J00241.

```
oligo #7061 (C sense primer):        (SEQ ID NO 41)
              ThrValAla...
5'-TCGAAGCTTAGTACTGTGGCTGCACCATCTGT-3'
         HindIII ScaI oligo #7060 (C_K antisense primer):   (SEQ ID NO 42)
              CysGluGly...
5'-GTCGAATTCTfGCGCACTCTCCCCTGTTGAAGC-3'
         EcoRI FspI
```

PCR amplification using the 7060/7061 primers is expected to yield a fragment of 342 basepairs. ScaI/FspI digestion of this fragment should yield a blunt fragment starting at the first AA, Thr of $C_K$ and ending at the last AA, Cys. A stop codon is not present.

PCR reaction was carried out in a final volume of 50 μl, using 2 μl of the RT reaction, 10 pmol of each primer and 5U of either Taq DNA polymerase (Stratagene, La Jolla, Calif., USA). dNTPs were present at a final concentration of 200 μM in 1×Taq buffer as provided by the supplier. Reactions were overlaid with 75 μl paraffin oil. Cycling conditions were as follows. After an initial denaturation of 5 min at 95° C. 40 PCR cycles (1 min 94° C., 1 min at appropriate annealing temperature of 60° C. and 1 min at 72° C.) were carried out. There was a final extension phase of 10 min at 72° C. 5 μl amounts of the reaction were run on agarose gels.

The PCR reaction with the 7060/7061 primer pair yielded a single band of ±300 bases, which was purified using the Geneclean® kit (Bio101, Vista, Calif, USA), digested with EcoRI/HindIII, phenol:CHCl$_3$ extracted and ligated into EcoRI/HindIII digested pBSK(-) vector (Stratagene). The ligation mix was electroporated into the DH5αF' bacterial strain. Transformed bacteria were plated onto X-gal/IPTG LB agar plates for blue/ white selection of recombinants. Four white colonies were selected for further analysis and plasmid DNA was prepared. EcoRI/HindIII restriction analysis showed that all 4 $C_K$ transformants contained an insert of the correct length. The 4 inserts were entirely sequenced. One clone was completely identical to the database sequence (accession nrs V00557 and J00241). The corresponding plasmid was named pBLSKIGkappaC.

Cloning of the Human Cγ1 Heavy Chain Constant Domain cDNA:

The cDNA was used as template for PCR amplification using primer sequences based on the Genbank database sequence: accession # Z17370.

```
oligo #7601 (Cγ1 sense primer; 48-mer, should only be Cγ1 specific)
              AlaSerThr...
5'-CTAGAATTCTGCGCATCCACCAAGGGCCCATCGGTCTTCCCCCTGGCA-3'    (SEQ ID NO 43)
         Ec6RI FspI oligo #7600 (C 1 antisense primer):
              LysGlyProSer...
5'-GTAAAGCTTGAGCTCTTACCCGGAGACAGGGAGAGG-3'                (SEQ ID NO 44)
         HindIII SacI
```

PCR amplification using the 7601/7600 primer couple is expected to yield a fragment of 1016 basepairs. FspI/SacI cleavage of this fragment followed by removal of the SacI 3' overhang should yield a blunt fragment starting with the first AA, Ala of Cγ1 and ending with the last AA, Lys. A stop codon is not included. PCR reactions were carried out in a final volume of 50 μl, using 2 μl of the RT reaction, 10 pmol of each primer and 5U of Taq DNA polymerase (Stratagene). dNTPs were present at a final concentration of 200 μM in 1×Taq buffer as provided by the supplier. Reactions were overlaid with 75 μl paraffin oil. Cycling conditions were as follows: after an initial denaturation of 5 min at 95° C. 40 PCR cycles (1 min 94° C., 1 min at appropriate annealing temp. 55° C. and 1 min at 72° C.) were carried out. There was a final extension phase of 10 min at 72° C. 10 μl amounts of the reaction were run on agarose gels. A single band of around 1 kb was obtained. The 1 kb band, obtained with the 7601/7600 primer pair, was purified using the Qiaquick™-kit (Qiagen, Hilden, Germany) and ligated into pGEM-T-vector. The ligation mix was transformed into the DH5αF' bacterial strain. Transformed bacteria were plated onto X-gal/IPTG LB agar plates for blue/white selection of recombinants.

Eight white colonies were selected for further analysis and plasmid DNA was prepared. Restriction analysis with BstXI (=specific for IgG-1; absent in IgG-2) showed that 6 transformants contained a Cγ1 insert of the correct length. One clone was entirely sequenced and was shown to be identical to the database sequence, except for 3 codon switches, wich correspond to a described allotypic variant Gm(-1,4) of the human IgG1 (lys214->arg214, asp356->glu356 and leu358->met358 respectively). Since the Gm(-1) ("nonmarker"), glu356/met358, also occurs on Cγ2, this marker will likely not be immunogenic when introduced in humans. The cloned sequence also contained two silent base switches in comparison to the database sequence Z17370. The final construct was named pGEMThIGG1c.

The C1q-complement binding site present in the $C_H$2 region of the human IgG1, known to induce complement activation upon injection of the recombinant antibody (Xu et al., 1994), was later mutated (Pro$_{331}$→Ser) as described further during the assembly of the humanized D9D10 fusion cDNA.

Construction of Fusion cDNAs

In order to assemble the light—and heavy chain fusion genes, several intermediate cloning constructs, generated by PCR-assembly and amplification, were needed.

Assembly of the Light Chain Fusion cDNA

The mouse D9D10 $V_K$ leader sequence cDNA was cloned by PCR-assembly (Stemmer et al., 1995) of four partially overlapping synthetic oligonucleotides [IG8180, IG8179, IG8178 and IG8176] of each 40 bps, and subsequent PCR-amplification with two specific outside primers [IG 8175 and 8174]. The resulting 100 bp PCR fragment I, named Ldr, consist of a 5' untranslated region of 20 bp, including an XbaI cloning site, and the cDNA encoding the complete D9D10 $V_K$ leader peptide (20 AA) and 20 bp of the humanized D9D10 light chain variable domain cDNA encoding the first 6 AA.

```
Sense strand oligos:

XbaI
IG8180         5'-GTCCCCCGGGTACCTCTAGAATGGATTTTCAAGTGCAGAT-3'
               (SEQ ID NO 45)

IG8179         5'-TTTCAGCTTCCTGCTAATCAGTGCCTCAGTCATACTCTCG-3'
               (SEQ ID NO 46)

Antisense strand oligos:

IG8178         5'-CTCTGGGTCAGCTCGATGTC6GAGAGTATGACTGAGGCAC-3'
               (SEQ ID NO 47)

IG8176         5'-TGATTAGCAGGAAGCTGAAAATCTGCACTTGAAAATCCAT-3'
               (SEQ ID NO 48)

PCR amplification primers:

XbaI
IG8175 (sense)    5'-GTCCCCCGGGTACCTCTAGAATG-3'
                  (SEQ ID NO 49)

IG8174 (antisense) 5'-CTCTGGGTCAGCTCGATGTCC-3'
                   (SEQ ID NO 50)

IG81756
       IG8180                   IG8179
-------------------   ------------------

IG8176       IG8178
             -----------------  -----------------

IG81747
```

The humanised light chain variable domain as present in pGEM-T-$V_L$ H, described earlier, was PCR-amplified using primers [IG8172 and IG8171] designed to produce PCR fragment II containing the complete variable domain cDNA with exception of the last 3 amino acids (IKR), and flanked at the 3'-terminus by an XhoI-cloning site.

```
IG8172 (sense)  5'-GACATCGAGCTGACCCAGAGCCCGGCG-3'
                (SEQ ID NO 51)

XhoI
IG8171 (anti-   5'-CGCGCTCGAGTTTGGTACCCTG-3'
sense)          (SEQ ID NO 52)
```

Fusion of the two DNA fragments PCR-I (Ldr) and PCR-II ($V_{Lh}$), having 20 bp overlap, was performed by overlap PCR using primerset IG8175 and IG8171. The resulting PCR-III fragment was directly cloned in pGEM-T resulting in the pGEMLdrV$_{Lh}$ plasmid.

```
                           XbaI
IG8175 (sense)    5'-GTCCCCCGGGTACCTCTAGAATG-3'
                  (SEQ ID NO 49)

XhoI
IG8171 (antisense) 5'-CGCGCTCGAGTTTGGTACCCTG-3'
                   (SEQ ID NO 52)
```

The human $_K$-light chain constant domain was cloned by PCR-amplification using pBLSKIGkappaC as template with primers IG8170 and IG8169. The resulting PCR-IV fragment consists of the cDNA sequence encoding the last 3 AA of $V_{Lh}$ and the complete human Ckappa constant domain, followed by a stop codon and an EcoRI cloning site. The PCR-IV DNA was directly cloned in the pGEM-T vector resulting in the pGEM-TC$_L$ plasmid.

XhoI

```
                         -continued
IG8170(sense)      5'-GCGCCTCGAGATCAAACGGACTGTGGCTGCACCATCTG-3'
                      (SEQ ID NO 53)

EcoRI
IG8169(antisense)  5'-GCCGGAATTCCTAGCACTCTCCCCTGTTGAAG-3'
                      (SEQ ID NO 54)
```

Fusion of LdrV$_{Lh}$ and C$_L$ cDNA in the pGEM-T backbone was realised by insertion of the C$_L$-containing XhoI-SpeI fragment, isolated from pGEM-TC$_L$ plasmid, in the pGEMLdrV$_{Lh}$ plasmid. The resulting construct was named pGEMhD9D10$_L$.

Assembly of the Heavy Chain Fusion cDNA

The mouse D9D10 V$_K$ leader sequence cDNA was cloned by PCR-assembly (Stemmer et al., 1995) of four partially overlapping synthetic oligonucleotides [IG8180, IG8179, IG8176 and IG8177] of each 40 bps, and subsequent PCR-amplification with two specific outside primers [IG 8175 and 8173]. The resulting 100 bp PCR-V fragment, named Ldr-2, consist of a 5' untranslated region of 20 bp, including an XbaI cloning site, and the cDNA encoding the complete D9D10 V$_K$ leader peptide (20 AA) and 20 bp of the humanized D9D10 heavy chain variable domain cDNA encoding the first 6 AA.

Fusion of Ldr-2 and V$_{Hh}$ was performed by overlap PCR on a mixture of PCR-V and PCR-VI using sense primer IG 8175 and an antisense primer IG 8166, resulted in a PCR fragment (LdrV$_{Hh}$) which was directly cloned in a pGEM-T vector, resulting in PGEMLdrV$_{Hh}$.

```
Sense strand oligos:
                                                   XbaI
IG8180              5'-GTCCCCCGGGTACCTCTAGAATGGATTTTCAAGTGCAGAT-3'
                       (SEQ ID NO 45)
IG8179              5'-TTTCAGCTTCCTGCTAATCAGTGCCTCAGTCATACTCTCG-3'
                       (SEQ ID NO 46)
Antisense strand oligos IG8177              5'-CTCTGCACCAGCTGCACCTGCGAGAGTATGACTGAGGCAC-3'
                       (SEQ ID NO 55)
IG8176              5'-TGATTAGCAGGAAGCTGAAAATCTGCACTTGAAAATCCAT-3'
                       (SEQ ID NO 48)
PCR amplification primers:
                                                   XbaI
IG8175(sense)       5'-GTCCCCCGGGTACCTCTAGAATG-3'
                       (SEQ ID NO 49)
IG8173(antisense)   5'-CTCTGCACCAGCTGCACCTGC-3'
                       (SEQ ID NQ 56)
IG81756
       IG8180                IG8179

-------------------   ------------------

IG8176           IG8177

----------------  -----------------
                                       IG81737
```

The humanised variable heavy chain domain as present in pGEM-T-V$_H$H, described earlier, was PCR-amplified using primers (IG8168 and IG8167) designed to produce PCR-VI fragment containing the complete variable domain cDNA, and flanked at the 3'-terminus by an XhoI-cloning site.
IG8168(sense)

```
IG8168(sense)      5'-CAGGTGCAGCTGGTGCAGAGCGGTAG-3'
                      (SEQ ID NO 57)

XhoI
IG8167(antisense)  5'-CGCCGGCTCGAGACGGTGACCGTGGTCCCTTGGCCCCAGTAATCC-3'
                      (SEQ ID NO 58)
```

```
                        XbaI
IG8175(sense)     5'-GTCCCCCGGGTACCTCTAGAATG-3' (SEQ ID NO 49)

XhoI
IG8166(antisense) 5'-CGCCGGCTCGAGACGGTGACC-3'   (SEQ ID NO 59)
```

The human heavy chain constant domain cDNA was produced by PCR amplification on pGEMThIGG1c as template, using sense primer IG 8165, designed to introduce a XhoI restriction site and antisense primer IG 8164 that added an extra leucine to the $C_H$ sequence and introduced a STOP codon followed by an EcoRI cloning site. The introduction of a codon for a leucine provided, together with the codon for a lysine (normally the last amino acid), a HindIII restriction site. This HindIII site was used to insert a scFv-module (cfr MoTAbII expression plasmids, see below). The resulting fragment PCR-VII was inserted in the pGEM-T vector resulting in plasmid pGEM-TC$_H$.

```
                         XhoI
IG8165(sense)     5'-GCCGCTCGAGCGCATCCACCAAGGGC-3'
                  (SEQ ID NO 60)

EcoRI    HindIII
IG8164(antisense) 5'-GCCGGAATTCGCTAAAGCTTACCCGGAGACAGGGAGAGG-3'
                  (SEQ ID NO 61)
```

The amino acid Pro at position 331 in the $C_H2$ domain of both IgG1 and IgG4 immunoglobulins is described to contribute to their differential ability to bind and activate complement (Xu et al., 1994). The Pro331-codon CCC was therefore mutated to a Ser331-codon, TCC. Two specific primers IG 8460 and IG8459 were designed, to introduce this mutation by PCR mutagenesis.

Two separate PCR-amplifications were performed on pGEM-T-C$_H$ as template using (1) primers IG2617, matching with the T7-promoter region in pGEM-T and IG8460, resulting in a 733 bp PCR-VIII fragment, and (2) primers IG 8459 and IG3899, matching the SP6-promoter in pGEM-T, resulting in a 473 bp PCR-IX fragment. Overlap PCR was subsequently performed on a mixture of PCR-VIII and PCR-IX, using again the primers IG2617 and IG3899, resulting in a 1178 bp PCR-X fragment. The amplified PCR-X fragment was eventually inserted as an XhoI-SpeI fragment (1018 bp) in the pGEMLdrV$_{Hh}$ plasmid. The resulting pGEMhD9D10$_H$ plasmid contains the complete coding sequence of the humanized D9D10 heavy chain fusion protein.

lymphoid mammalian cell lines. Basically an expression plasmid(s), containing the immunoglobulin genes coding for respectively heavy and light chain proteins under transcriptional control of a promoter/enhancer unit recognized in mammalian cells, is introduced in the chosen host cells together with (as one plasmid or on separate plasmids) a drug-resistance gene expression unit by classical cell transfection techniques. Cells that have randomly integrated the foreign expression units in their cell genome are initially selected for their drug-resistant phenotype and secondly for high level, stable expression of the protein of interest, the immunoglobulin. After gene integration, an increase in the immunoglobulin expression level can be obtained by coamplification of the genes through further selection of isolated recombinant cell lines for increased resistance to the drug resistance marker.

One possible example of a successful strategy for mammalian cell expression is the glutamine synthetase based selection/amplification method shown to result in high level production of mammalian proteins in different cell types including Chinese hamster ovary cells (CHO) (Cockett et al., 1990) and myeloma cells, Ns0 (Bebbington et al., 1992). The use of the system is covered by patents WO87/04462 and WO89/10404 (Lonza Biologicals, Slough, UK).

Following the GS-expression method, the fusion genes coding for respectively the heavy- and light chain of the recombinant immunoglobulins were cloned in a mammalian expression plasmid (pEE12 or pEE14) under transcriptional control of the strong Cytomegalovirus major immediate early promoter /enhancer (CMV-MIE). This plasmid also carries a cloned glutamine synthetase (GS) gene expression element that can act as a dominant selectable marker in a variety of cells. GS indeed provides the only pathway for

```
IG8459 (sense)          5'-GCCCTCCCAGCCTCCATCGAGAAAAC-3'
                                       Ser331
                        (SEQ ID NO 62)

IG8460 (antisense)      5'-GTTTTCTCGATGGAGGCTGGGAGGGC-3'
                                       Ser331
                        (SEQ ID NO 63)

IG2617 (sense-T7)       5'-TAATACGACTCACTA-3'
                        (SEQ ID NO 64)
IG3899 (antisense-SP6)  5'-ATTTAGGTGACACTATAG-3'
                        (SEQ ID NO 65)
*Construction of mammalian expression plasmids
```

Successful high level expression of recombinant immunoglobulins has been reported in both lymphoid and non-synthesis of glutamine using glutamate and ammonia as substrates. The final fusion product LdrV$_{Lh}$C$_L$ or hD9D10$_L$ was directly cloned as an XbaI-EcoRI fragment isolated from the plasmid pGEMhD9D10$_L$ in the mammalian expression vectors pEE14 (for CHO) and pEE12 (for Ns0) (Lonza biologicals) under transcriptional control of the CMV promoter, resulting in the plasmids pEE12hD9D10$_L$ and pEE14hD9D10$_L$.

The cDNA encoding the heavy chain fusion protein LdrV$_{Hh}$C$_H$ or hD9D10$_H$ was first transferred from the pGEMhD9D10$_H$ construct as an XbaI-EcoRI fragment in the intermediate vector pEE6hCMV-BgIII (Lonza Biologicals), also behind the CMV promoter. From the latter construct pEE6hD9D10$_H$ a complete mammalian expression casette, consisting of CMV-promoter followed by the fusion gene and a polyadenylation site, were transferred as an BgIII-BamHI DNA fragment in the BamHI opened plasmids pEE12hD9D10$_L$ and pEE14hD9D10$_L$ expression plasmids already available. The final expression plasmids, named pEE12hD9D10 and pEE14hD9D10 then consists of the pEE-backbone plasmid containing the GS-selection unit, carrying the light chain fusion gene expression casette followed by a comparable heavy chain fusion gene expression casette.

The approach of assembling a single expression plasmid containing separate transcription units for both heavy and light chains and the selectable marker, is adviced in order to ensure coamplification with the marker gene.

Figure 5:
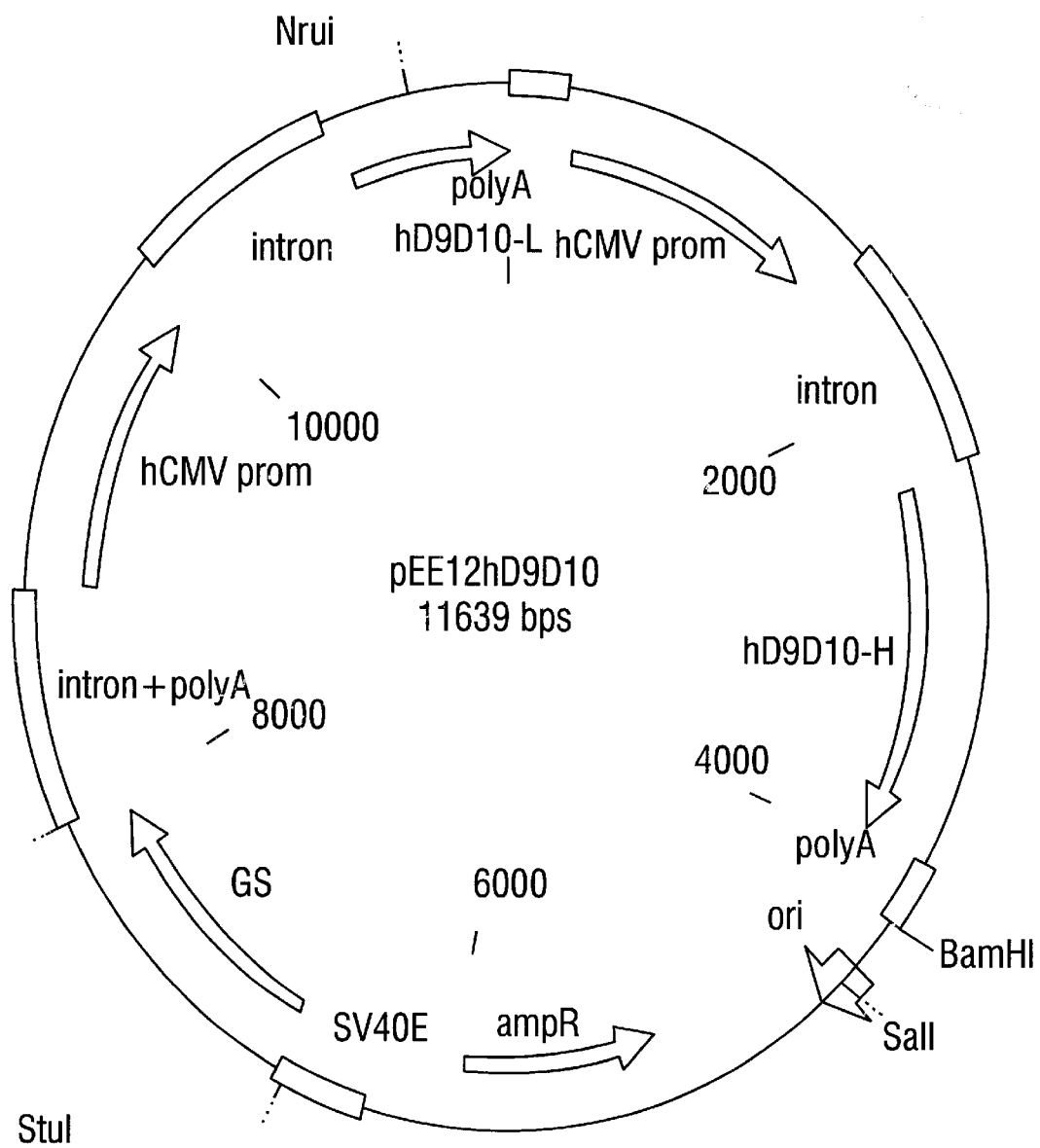
FIG. 5 shows a schematic representation of the mammalian expression plasmid pEE12hD9D10 used for expression of humanized D9D10 whole antibody in (1) COS cells (2) stable recombinant Ns0 cell lines.
Major Plasmid Building Blocks:
  prokaryotic sequences for plasmid DNA preparation in E.coli (ori of replication and amp$^R$ ampicilline resistance expression unit)
  SV40 origin of replication (part of SV40E, SV40 early promoter) allowing transient expression in SV40 permissive, T-antigen producing cell lines (e.g. COS)
  human Cytomegalovirus major immediate early promoter/enhancer (hCMVprom+intron) controlled expression casette for hD9D10 heavy chain protein (hD9D10-H)
  human Cytomegalovirus major immediate early promoter/enhancer (hCMVprom+intron) controlled expression casette for hD9D10 light chain protein (hD9D10-L)
  SV40 early promoter (SV40E) controlled glutamine synthetase cDNA (GS) expression unit for selection/amplification
  polyA=SV40 early region poly-adenylation signal intron+polyA=SV40 t-antigen intron +SV40 early region poly-adenylation signal
Figure 6:
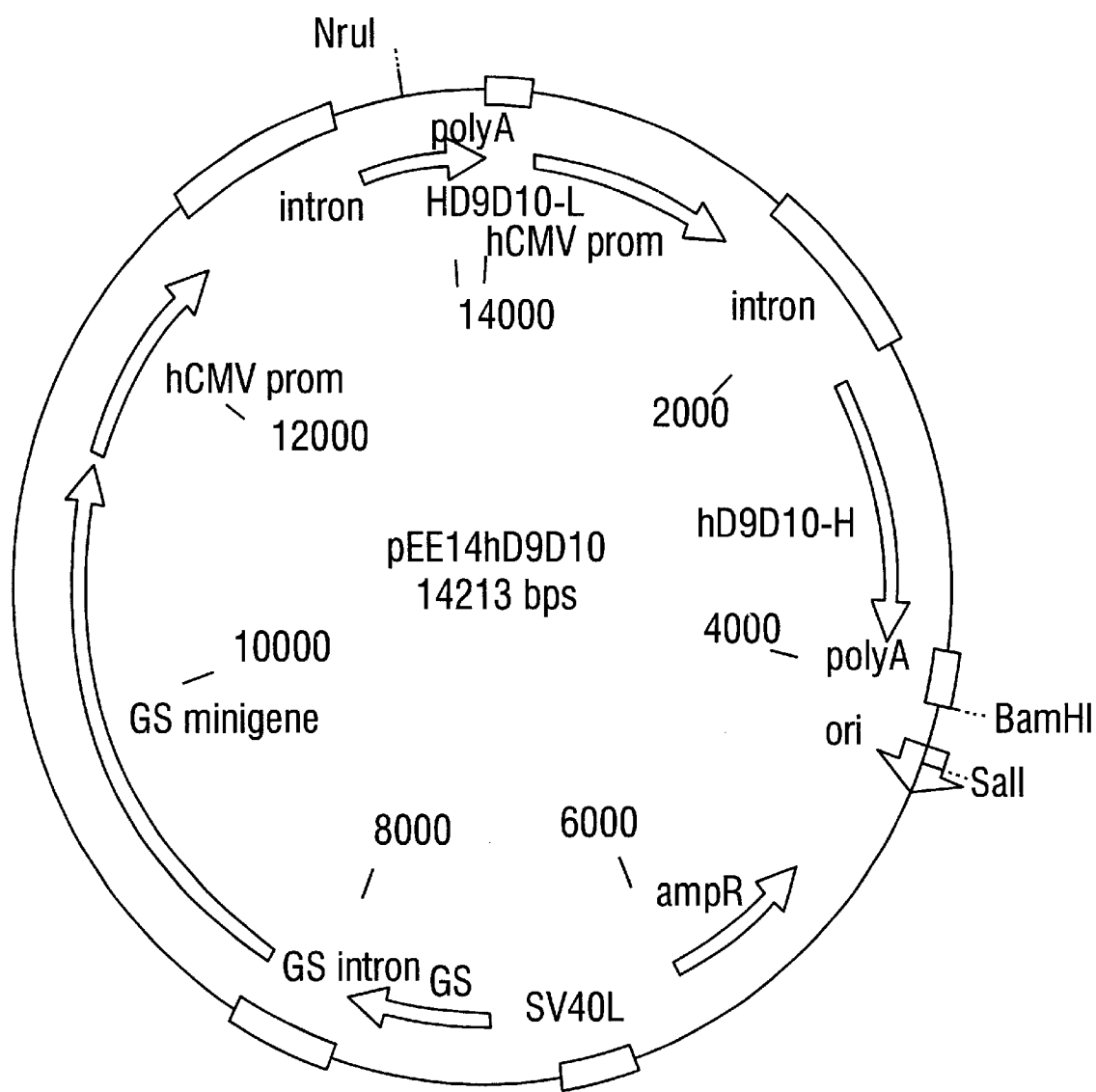
FIG. 6 shows a schematic representation of the mammalian expression plasmid pEE14hD9D10 used for expression of humanized D9D10 whole antibody in (1) COS cells (2) stable recombinant CHO-K1 cell lines.
Major Plasmid Building Blocks:
  prokaryotic sequences for plasmid DNA preparation in E. coli (ori of replication and amp$^R$ ampicilline resistance expression unit)
  SV40 origin of replication (part of SV40E, SV40 early promoter) allowing transient expression in SV40 permissive, T-antigen producing cell lines (e.g. COS)
  human Cytomegalovirus major immediate early promoter/enhancer (hCMVprom+intron) controlled expression casette for hD9D10 heavy chain protein (hD9D10-H)
  human Cytomegalovirus major immediate early promoter/enhancer (hCMVprom+intron) controlled expression casette for hD9D10 light chain protein (hD9D10-L)
  SV40 late promoter (SV40L) controlled glutamine synthetase mini gene (GS+intron) expression unit for selection/amplification
  polyA=SV40 early region poly-adenylation signal
  intron+polyA=SV40 t-antigen intron+SV40 early region poly-adenylation signal

A schematic representation of both plasmids is given in FIGS. 5 and 6.

The cDNA sequence encoding the complete humanized D9D10 heavy chain fusion protein is given in FIG. 7. (SEQ ID NO 66)

The cDNA sequence encoding the humanized D9D10 light chain fusion protein is given in FIG. 8. (SEQ ID NO 68)

The amino acid sequence of the humanized D9D10 heavy chain fusion protein is given in FIG. 9. (SEQ ID NO 67)

Figures 10, 11:
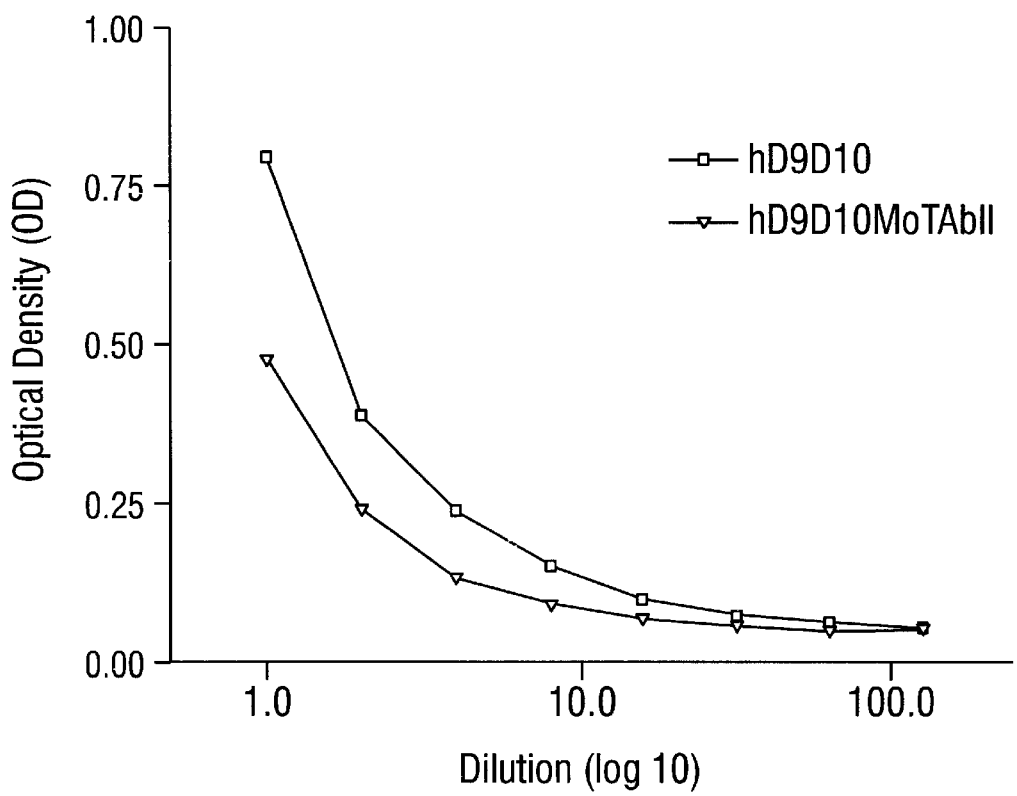
FIG. 10 shows the amino acid sequence of the humanized D9D10 and MoTAbII light chain fusion protein.
  Aa 1–20: D9D10 light chain signal sequence
  Aa 21–127: humanized light chain variable domain of D9D10
  Aa 128–233: human kappa light chain constant domain
  Number of residues: 233.
  Molecular weight (MW): 25582 (SEQ ID NO 69)
FIG. 11 shows the binding in ELISA of different concentrations of humanized D9D10 and humanized D9D10 MoTabII (=different dilutions of crude COS supernatant containing humanized D9D10 or humanized D9D10 MotabII) to immobilized human IFN. The assay is performed as described in example 2.

The aminoacid sequence of the humanized D9D10 light chain fusion protein is given in FIG. 10. (SEQ ID NO 69)

Small Scale Expression of Humanized D9D10 Chimeric Antibody in COS Cells

A quick way to determine the feasibility of expressing a recombinant protein in mammalian cells and to evaluate its functionality, is transient expression of the product in COS cells (Gluzmann, 1981). COS cells are Simian Virus 40 (SV40)-permissive CV1 cells (African monkey kidney) stably transformed with an origin-defective SV40 genome, thereby constitutively producing the SV40 T-antigen. In SV40-permissive cells, T-antigen initiates high copy number transient episomal replication of any DNA-vector that contains the SV40 origin of DNA replication. Both the pEE12 and pEE14 expression vectors contain an SV40 origin of replication in the SV40 early promoter region controlling the GS-selection gene, and thus permits efficient transient expression in COS cells.

Small amounts of functionally active antibody were made by transient expression in COS cells. COS7 cells (ATCC CRL 1651) were routinely cultured in DMEM supplemented with 0.03% glutamine and 10% fetal calf serum. For preparative scale transfection, an optimized DEAE-transfection protocol (McCutchan, 1968) was used. Alternatively, other well known transfection methods such as Ca-phosphate precipitation, electroporation, liposome-based transfection can be used. Briefly, exponentially growing COS7 cells were seeded in cell factories (Nunc, Rochester, N.Y., USA) at 3.5 $10^4$ cells/cm$^2$ about 18 h before transfection, after which the cells were washed twice with MEM-Hepes pH 7.1 (Gibco, Rockville, Md., USA) and allowed to cool to bench temperature. 0.5 $\mu$g/cm$^2$ cell surface of high quality plasmid DNA (CsCl-density purification) of the mammalian expression plasmids pEE12hD9D10 and pEE14hD9D10 was ethanol precipitated, redissolved in 25 $\mu$l/cm$^2$ MEM-Hepes pH 7.1 and slowly added to the same volume of 2 mg/ml DEAE-dextran MW 500.000 (Pharmacia) in MEM-Hepes pH 7.1. The DNA-DEAE-dextran precipitate (50 $\mu$l/cm$^2$) was allowed to form for 20–25 min, put on the cells for 25 min and removed to be stored at −20° C. (the same precipitate can be reused in a second transfection experiment with the same efficiency).

The cells were incubated during the next 3.5 hours in DMEM growth medium (Gibco) containing 0.1 mM chloroquine (Sigma) (0,3 ml /cm$^2$) in a CO$_2$-incubator at 37° C., then washed two times with growth medium and further incubated for 18 hrs in complete culture medium enriched with 0.1 mM sodium butyrate (Sigma) at 37° C. (0.3 ml/cm$^2$). The next day the cells were washed twice with serum free DMEM medium supplemented with 0.03% glutamine (Merck) and then incubated for 48h (determined in analytical scale experiments as the optimal harvest time) in 150 $\mu$l/cm$^2$ cell surface of the same medium at 37° C., after which conditioned medium was harvested and stored at −70° C. until purification. As negative control COS cells were also transfected with the empty expression vectors pEE12 and pEE14.

Quality control of the crude CM was performed by IFN$\gamma$-binding assay in ELISA format, by SPR-analysis and by measuring the inhibition of IFN$\gamma$ mediated MHC class II-induction.

Human Interferon—Coating Elisa 96 well ELISA culture plates (Nunc 469914) were coated with 100 ng/well hIFN$\gamma$ (Genzyme 80-3348-01, 1 mg/ml) diluted in 50 mM TrisHCl pH8.5, 150 mM NaCl, by 18 h incubation at 4° C. Blocking of nonspecific binding was performed in PBS/0.1% caseine (×200 $\mu$l/well, 1 h, 37° C.). All washing steps were performed with PBS/0.05% Tween-20 (3×200 $\mu$l/well). Purified mouse-human chimeric D9D10 whole antibody (EP 0 528 469 to Billiau and Froyen), produced by transient expression in COS cells, was used as positive control (concentration range 500 ng/well to 4 ng/well, ½ dilution series prepared in the sample diluent, 100 $\mu$l/well). Samples were diluted in a ½ dilution series in PBS/0.1% caseine, and incubated for 2 h at 37° C. Detection was performed using an alkaline-phophatase conjugated goat-anti-human IgG$_{H+L}$ (PromegaS3821), diluted 1/2000 in PBS/0.05% caseine, incubated for 2 h at 37° C. AP-substrate (SigmaN-2765) was used at a concentration of 1 mg/ml in 100 mM TrisCl pH9.5, 100 MM NaCl, 5 mM MgCl$_2$. Plates were analysed at 405/595 nm after resp. 15 and 30 min incubation at 37° C.

Results are shown in FIG. 11: humanized D9D10 clearly interacts with human IFN$\gamma$ coated onto the wells.

SPR Analysis

Figure 12:
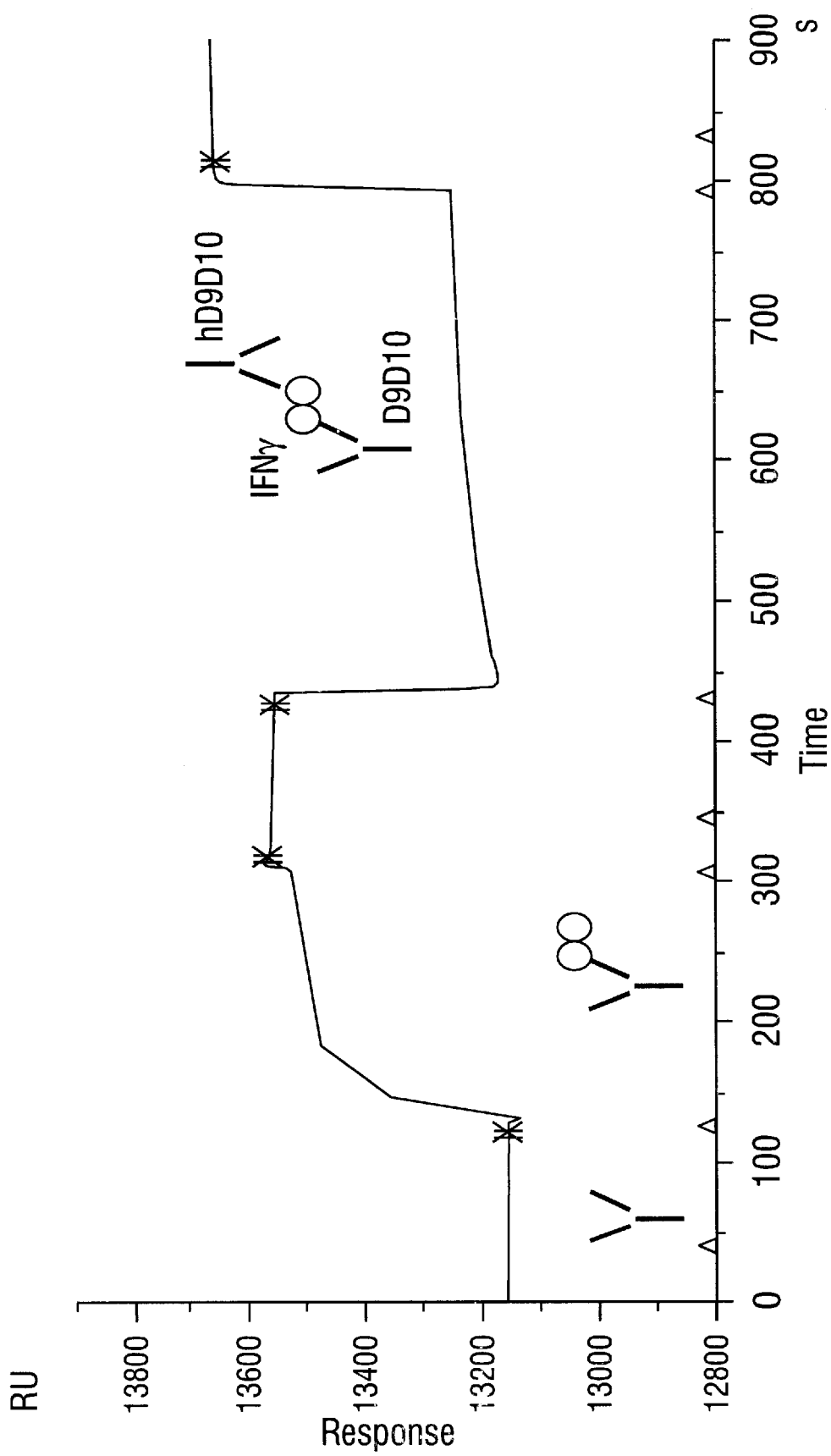
FIG. 12 shows the interaction of humanized D9D10 (=crude COS supernatant containing humanized D9D10) with IFN using SPR analysis. The assay is performed as described in example 2.

A comparable set up was used as described for the evaluation of the murine and humanized scFvD9D10 derivatives. Briefly, murine D9D10 was immobilized directly onto a B1 sensorchip (BIACORE AB)—containing less carboxylic groups and for which as such no pretreatment is necessary—at a concentration of 10 $\mu$g/ml D9D10 in an acetate buffer pH 4.8 using amine coupling. A fixed concentration of 8 $\mu$g/ml human IFN$\gamma$ was added, followed by the injection of either murine D9D10 (10 $\mu$g/ml; positive control) or crude COS supernatant containing humanized D9D10. Results are shown in FIG. 12. These data clearly illustrate the presence of active, IFN$\gamma$ binding molecules in the COS supernatant. As no exact concentrations were determined of the humanized D9D10, no affinity data were calculated.

Inhibition of MHC Class II-induction

See Example 8.1.

Purification of Humanized D9D10

Humanized D9D10 was purified using classical protein A chromatography (Perry and Kirby, 1990; Page and Thorpe, 1996). Quality control of the purified antibody construct was performed by Western Blot (classical technology) and ELISA. The latter is done as described above and results are shown in FIG. 13. From these results it is clear that purified, humanized D9D10 is specifically interacting with IFNγ coated onto the wells.

Generation of Stable Mammalian Expression Cell Lines

For generation of stable mammalian expression cell line, two host cell lines Ns0 (Galfre and Milstein, 1981; ECACC 85110503) and CHO-K1 (ATCC CCL61) were used.

The glutamine-dependent NS0 cells were routinely cultured in Lonza DME (JRH 51435)/200 mMglutamine/10%FCS. High quality plasmid DNA pEE12hD9D10, prepared by CsCl-density purification, and linearized by SalI digestion, was used for transfection of the NS0 cells by electroporation (40 μg DNA/$10^7$ cells). Transfected cells were then selected for the glutamine-independent phenotype by gradual reducing the glutamine concentration. Selection was performed in Lonza DME (JRH51435)/GS supplement (JRH58672)/10% dialysed FCS. Individual NS0 clones were isolated after±2 weeks of selection. The clones were analysed for recombinant antibody production and secretion by testing the cell conditioned medium in the IFNγ-coating ELISA described earlier.

Several positive cell lines were selected for subsequent vector amplification by growth in the presence of the GS-inhibitor MSX (methionine sulfoximine), resulting in increased humanized D9D10 antibody expression levels.

Large scale production of the recombinant antibody using high expressing NS0 recombinant cell lines is done in bioreactor systems (e.g. hollow fibre systems).

CHO-K1 cells were routinely cultured in GMEM-S (JRH51492)/200 mM glutamine/10%FCS. High quality plasmid DNA pEE14hD9D10, prepared by CsCl-density purification, was directly used for transfection of CHO-K1 cells by $Ca^{2+}$-phosphate transfection techniques (12μg/1.15 $10^6$ cells seeded 18 h before transfection on T-flasks). Selective medium, GMEM-S(JR51492)/GS supplement (JRH58672)/10% dialysed FCS/25 M MSX was added to the cells 24 h post-transfection. Individual clones could be isolated±2 weeks after transfection. Selected clones were analysed for recombinant antibody expression and secretion by testing the cell conditioned medium in the IFNγ-coating Elisa described earlier. Several positive cell lines were selected for subsequent vector amplification by growth in the presence of increased concentrations of the GS-inhibitor MSX, resulting in increased antibody expression levels.

Large scale production of the recombinant antibody using high expressing CHO-K1 recombinant cell lines is done in bioreactor systems (e.g. hollow fibre or ceramic core systems).

3. Generation of Humanized Sheep Anti-IFNγ Antibodies

Sheep antibodies were generated by immunizing sheeps according to standard immunization protocols. Briefly, sheeps were injected intradermally on multiple sites with the antigen (recombinant human IFNγ(procaryotic origin)) for several times over a timeframe of several months (day 0, 14, 28, 56, extra injections on a monthly basis). Serum is tested for its antiviral activity and its affinity (using SPR analysis).

As elution conditions necessary to elute an antigen from its antibody reflect the affinity of the antibody (McCloskey et al., 1997), experiments are performed in which the elution conditions of the sheep antibodies for human IFNγ were compared with those of the scFvD9D10 antibody.

Sheep monoclonal antibodies are generated by fusing B-lymphocytes isolated from peripheral blood with murine Sp2/0 myeloma cells according to the protocol as described in example 1. The affinity of the antibodies for human IFNγ is determined by SPR analysis as described in example 1.

4. Generation of Aanti-IFNγ Tetravalent Antibody Constructs 4.1. Generation of MoTAb I The MoTAb I (Monospecific Tetravalent Antibody) molecule is defined as a molecule which consists of 4 identical scFv molecules (e.g. humanized D9D10 scFv's) in the format of a homodimer of two identical molecules, each containing two scFv's. Both scFv's are linked together using a dimerisation domain, which drives the homodimerisation of the molecule (see FIG. 1). Comparable structures have already been described (Pack et al., 1995, Plückthun & Pack, 1997).

The humanized D9D10 scFv was used as a building block to generate the MoTAbI molecule using standard recombinant DNA techniques. A single MoTAb subunit started with a humanized D9D10 scFv followed by a dimerisation domain flanked by flexible linkers. The dimerisation domain was in turn linked C-terminally to a second D9D10 scFv. Finally a detection and purification tag was added to the extreme C-terminus of the molecule. However, in order to circumvent possible immunological reactions against the tag, MoTAb I was also produced in an untagged version. The sequence coding for the dimerisation domain and the flanking linkers were made synthetically using the method described by Stemmer et al. (1995). This synthetic domain was subsequently linked to both D9D10 scFv's. As linkers between the dimerisation domain and the scFv's, we have used the flexible and proteolysis-resistant truncated human IgG3 upper hinge region (Pack & Plückthun, 1992). As dimerisation domain we used either the helix-turn-helix motif described by Pack et al. (1993) or the leucine-zipper dimerisation domain originating from the human JEM-1 protein as described by Duprez et al. (1997). Optionally, an additional cysteine residue is inserted next to the dimerisation domain to provide extra stability. When applicable, a C-terminal detection and purification tag e.g. a hexahistidine sequence, is used. The sequences were assembled in such a way that functional domains were easily replaceable using unique restriction sites present in the molecule. For the construction of the pGEM-THDH vector, we synthesized 10 oligo's which collectively encode both strands of the HDH region (hinge region-dimerization domain-hinge region) flanked by a XhoI and a SpeI restriction site. The plus strand as well as the minus strand consist of 5 oligo's configured in such a way that, upon assembly, complimentary oligo's will overlap by 20 nucleotides. In these oligo's the codons where optimised for optimal E.coli usage. The resulting 223 bp fragment was cloned into a pGEM-T vector and several clones were sequenced.

Assembly Oligonucleotides for the HDH-domain

Amplification Oligonucleotides for the HDH-domain:

| Oligo No. | Oligo Seq. |
|---|---|
| 1s | 5'-CGCGCTCGAGATCAAACGGACCCCGCTGGGTGATACCACTC-3' (SEQ ID NO 70) |
| 2as | 5'-CAGTTCACCTCCGGAGGTATGAGTGGTATCACCCAGCGGG-3' (SEQ ID NO 71) |
| 3s | 5'-ATACCTCCGGAGGTGAACTGGAAGAGCTGTTGAAACATCT-3' (SEQ ID NO 72) |
| 4as | 5'-GACCTTTCAGCAGTTCTTTCAGATGTTTCAACAGCTCTTC-3' (SEQ ID NO 73) |
| 5s | 5'-GAAAGAACTGCTGAAAGGTCCGCGGAAAGGTGAACTGGAG-3' (SEQ ID NO 74) |
| 6as | 5'-TTCAGGTGCTTCAGCAATTCCTCCAGTTCACCTTTCCGCG-3' (SEQ ID NO 75) |
| 7s | 5'-GAATTGCTGAAGCACCTGAAAGAGCTGTTGAAAGGTACCC-3' (SEQ ID NO 76) |
| 8as | 5'-ATGGGTAGTATCACCTAGGGGGTACCTTTCAACAGCTCT-3' (SEQ ID NO 77) |
| 9s | 5'-CCCTAGGTGATACTACCCATACCAGCGGTCAGGTGCAACT-3' (SEQ ID NO 78) |
| 10as | 5'-CGCGGAATTCGCGTTCGCGACTAGTTGCACCTGACCGCTGGT-3' (SEQ ID NO 79) |

Amplification Oligonucleotides for the HDH-domain:

| Oligo No. | Oligo Seq. |
|---|---|
| 1s | 5'-CGCGGTATACTGACCCAGAGC-3' (SEQ ID NO 80) |
| 2as | 5'-CGCGCTCGAGTTTGGTACCCTG-3' (SEQ ID NO 81) |

The MoTAbI expressionplasmid was constructed as followed: The scFvD9D10 coding sequence was amplified by PCR using the pscFvD9D10 $V_{Hum}$ plasmid as a template. The sense primer used in this amplification carried a unique SpeI restriction site in such a way that the resulting scFvD9D10 sequence could be fused in-frame at the C-terminus of the dimerisation domain.
sense primer:

5'-CGCGACTAGTGCAGAGCGGTAGCGAAC-TG-3' (SEQ ID NO 82)

antisense primer:

5'-GCCAGTGAATTCTATTAGTGGTGATG-3' (SEQ ID NO 83)

Figure 14:
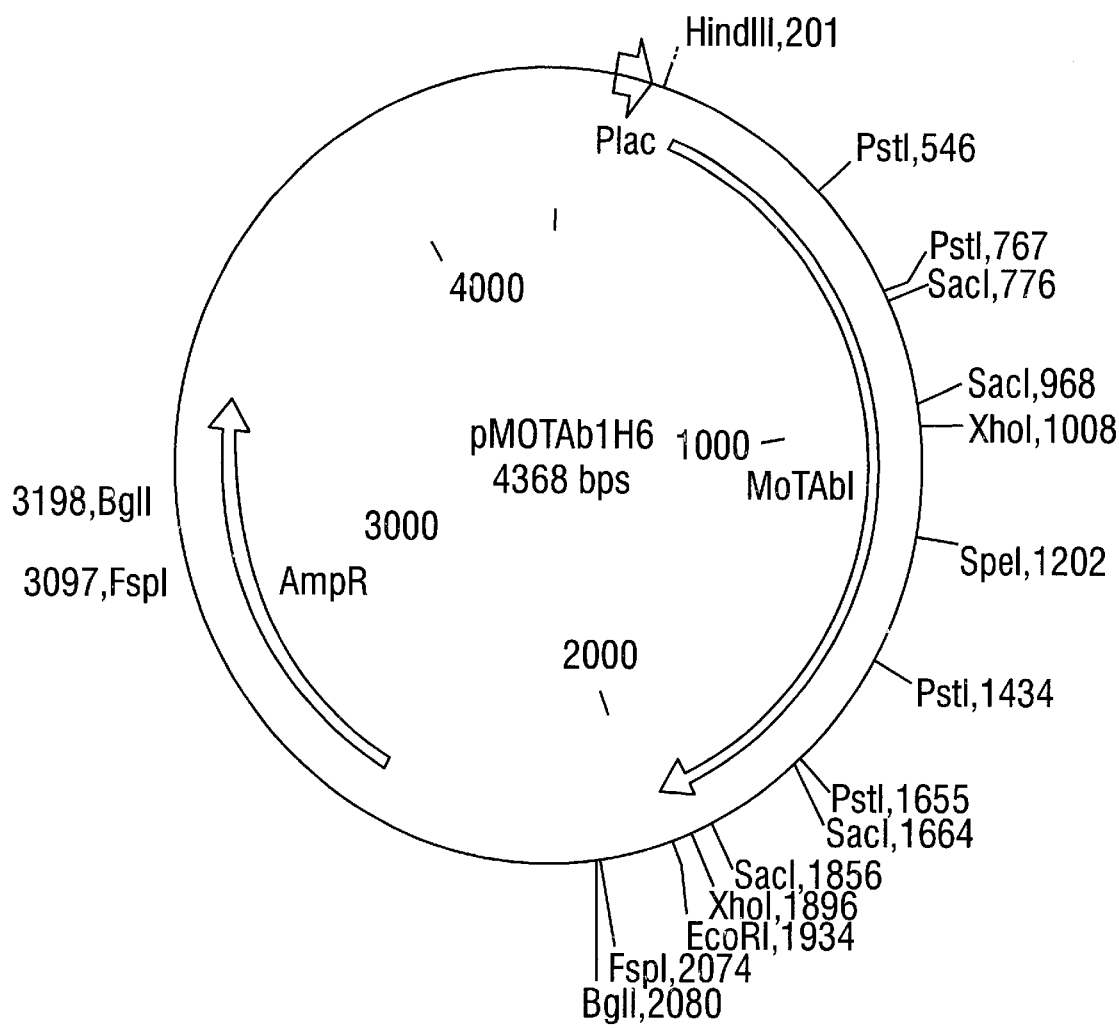
FIG. 14 shows a schematic representation of the expressionplasmid pMoTAbIH6 used for the expression of MoTAbI in E.coli.
Figure 18:
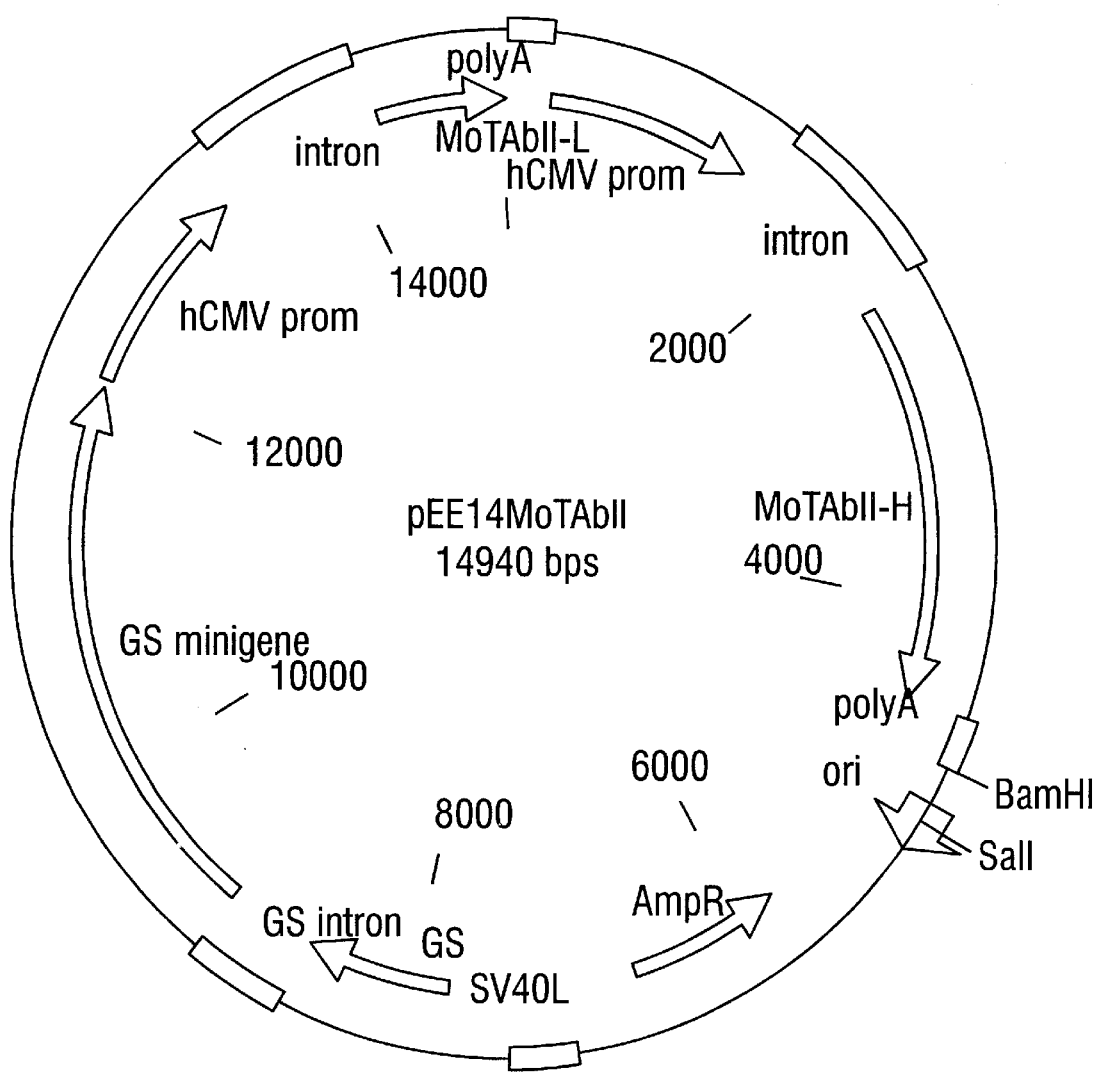
FIG. 18 shows a schematic representation of the mammalian expression plasmid pEE14MoTAbII used for expression of D9D10MoTAbII recombinant antibody in (1) COS cells (2) stable recombinant CHO-K1 cell lines.
Figure 21:
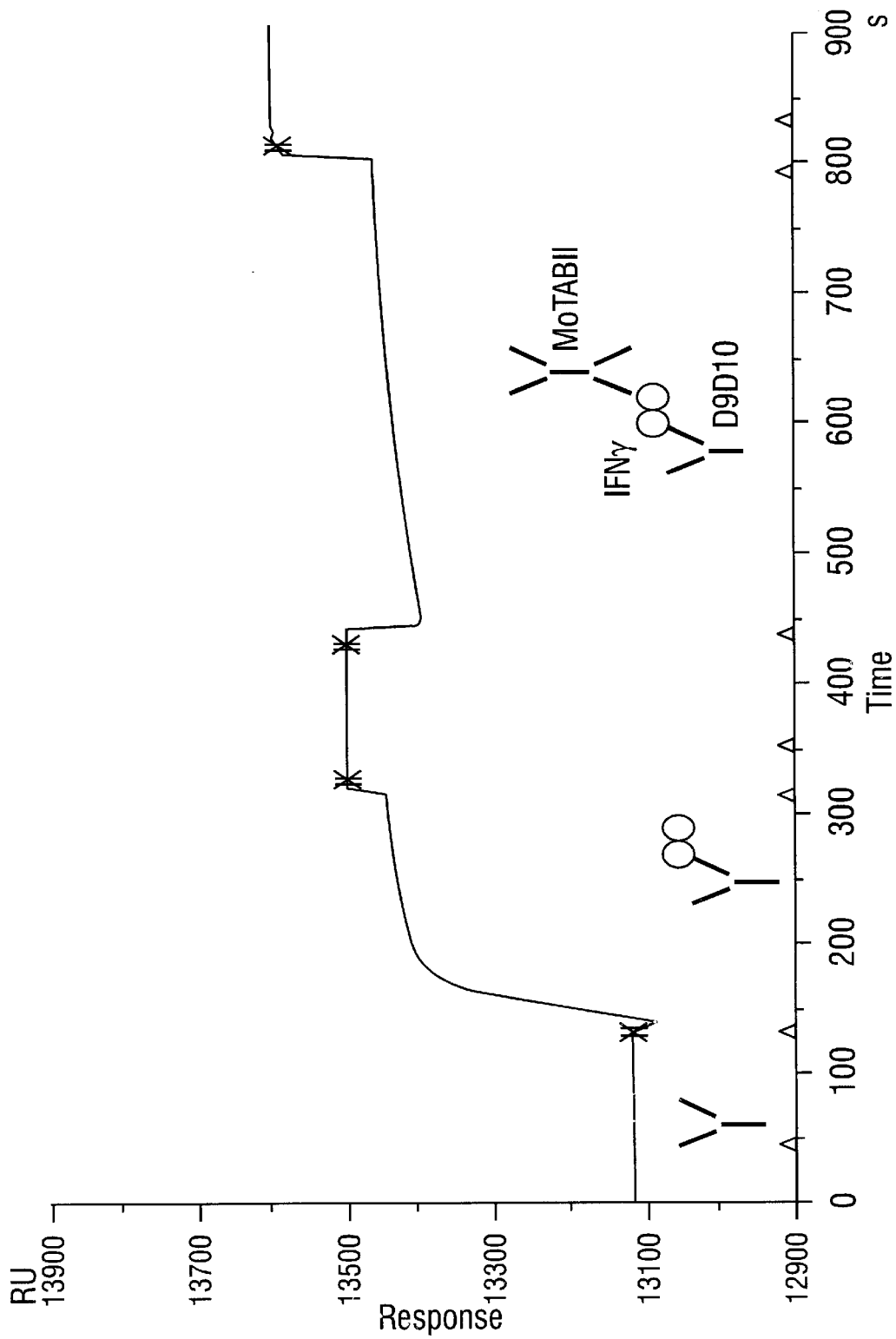
FIG. 21 shows the interaction of MoTAbII (=crude COS supernatant containing MoTAbII) with IFNγ using SPR analysis. The assay is performed as described in example 4.

The resulting PCR fragment was inserted into the pGEM-T vector and verified by DNA sequence analysis. The resulting plasmid was named pGEM-TscFvD9D10 f s/e. Subsequently, the MoTABI expressionplasmid was assembled in a three-point ligation using following fragments: The N-terminal scFvD9D10 originating from vector pscFvD9D10V$_{hum}$ as a XhoI/EcoRI fragment. This fragment also carried the antibiotic resistance gene (Amp), the origin of replication and the expression- and secretion signals. A second fragment, originating from pGEM-THDH cut with XhoI and SpeI, carried the helix-turn-helix dimerisation domain already described previously flanked by human IgG3 upper hinge regions. Finally, a third fragment, originating from the SpeI/EcoRI cut pGEM-TscFvD9D10 f s/e plasmid, carried the C-terminal scFvD9D10 with the hexahistidine tag. The final expressionplasmid was named pMoTAbIH6 (FIG. 14) and carried the MoTAbI molecule under control of the lac promotor and the pelB signal sequence as the secretion signal (FIGS. 15 and 16). (SEQ ID NO 84 and 85) To reduce immunogenicity, the hexahistidine sequence was removed using synthetic oligo's in a similar way as described previously for the humanized scFvD9D10, resulting in MoTabI. The MoTAb I expression plasmid was introduced into a suitable E.coli expression strain, e.g. JM83 and BL21. Good expressionlevels could be obtained in both strains. Detection of the MoTabI molecule (60 kDa) on western blot was done with an anti D9D10 rabbit polyclonal antibody and/or an anti His6 monoclonal antibody (Babco). However, only a minor amount of the MoTAbI molecule was present in a soluble form in the bacterial periplasm. The majority of the MoTAbI molecule was not able to traverse the bacterial membrane and was present as cytoplasmic inclusion bodies. This was confirmed by N-terminal amino acid sequencing which revealed still the presence of the pelB signal sequence on the molecule. The functionality of the minor amount of secreted MoTAbI could however be confirmed using an ELISA. In this ELISA, recombinant human IFNγ was coated onto a polystyreneplate and incubated with periplasmic fractions originating from E.coli cells expressing the MoTAbI molecule. Bound MoTAbI molecules where then detected using a rabbit polyclonal serum generated against the D9D10 scFv followed by a peroxidase labeled goat anti rabbit secondary serum.

Since most MoTAbI molecules were present in cytoplasmic inclusion bodies, the molecules were purified from this fraction under denaturing conditions followed by refolding to functional molecules. However, since the MoTAbI molecule has the pelB signal sequence still attached, a new cytoplasmic expressionplasmid was constructed. In this expressionplasmid, MoTAbI expression is under control of the strong leftward promotor of phage lambda ($P_L$). Since no secretion to the periplasmic space is necessary, the MoTAbI coding sequence was fused directly to an ATG startcodon. This was accomplished by isolating the MoTAbI coding sequence lacking the pelB signal sequence by PCR from the pMoTAbI expressionplasmid and recloning it into the EcoRV opened pBSK(+) vector (Stratagene). A SapI restriction site giving access to the first mature codon was hereby generated. After DNA sequence verification the MoTAbI coding sequence was inserted as a SapI blunt/SalI fragment into the NcoI blunt/SalI cut pIGRI2 vector.

pIGRI2 expressionvector nucleotide sequence
1 TTCCGGGGATCTCTCACCTACCAAACAATGC-CCCCCTGCAAAAAATAAAT 51 TCATATAAAAAACATACAGATAACCATCTGCGG-
TGATAAATTATCTCTGG
101 CGGTGTTGACATAAATACCACTGGCGGTGA-
TACTGAGCACATCAGCAGGA
151 CGCACTGACCACCATGAAGGTGACGCTCTT-
AAAAATTAAGCCCTGAAGAA
201 GGGCAGGGGTACCAGGAGGTTTAAAT-
CATGGTAAGATCAAGTAGTCAAAA
251 TTCGAGTGACAAGCCTGTAGCCCACGTCG-
TAGCAAACCACCAAGTGGAGG
301 AGCAGTAACCATGGTTACTGGAGAAGGGGG-
ACCAACTCAGCGCTGAGGTC
351 AATCTGCCCAAGTCTAGAGTCGACCTG-
CAGCCCAAGCTTGGCTGTTTGG
401 CGGATGAGAGAAGATTTTCAGCCTGATA-
CAGATTAAATCAGAACGCAGAA
451 GCGGTCTGATAAAACAGAATTTGCCTG-
GCGGCAGTAGCGCGGTGGTCCCA
501 CCTGACCCCATGCCGAACTCAGAAGT-
GAAACGCCGTAGCGCCGATGGTAG
551 TGTGGGGTCTCCCCATGCGAGAGTAGG-
GAACTGCCAGGCATCAAATAAAA
601 CGAAAGGCTCAGTCGAAAGACTGGGC-
CTTTCGTTTTATCTGTTGTTTGTC
651 GGTGAACGCTCTCCTGAGTAGGACAAATCCG-
CCGGGAGCGGAmTTGAACG
701 TTGCGAAGCAACGGCCCGGAGGGTG-
GCGGGCAGGACGCCCGCCATAAACT
751 GCCAGGCATCAAATTAAGCAGAAGGC-
CATCCTGACGGATGGCCTTTTGC
801 GTTTCTACAAACTCTTTTGTTTATTTTTCTAAA-
TACATTCAAATATGTAT
851 CCGCTCATGAGACAATAACCCTGATAAATGCTT-
CAATAATAAAAGGATCT
901 AGGTGAAGATCCTTTTTGATAATCTCAT-
GACCAAAATCCCTTAACGTGAG
951 TTTTCGTTCCACTGAGCGTCAGACCCCG-
TAGAAAAGATCAAAGGATCTTC
1001 TTGAGATCCTTTTTTTCTGCGCGTAATCTGCT-
GCTTGCAAACAAAAAAAC
1051 CACCGCTACCAGCGGTGGTTTGTTTGC-
CGGATCAAGAGCTACCAACTCTT
1101 TTTCCGAAGGTAACTGGCTTCAGCA-
GAGCGCAGATACCAAATACTGTCCT
1151 TCTAGTGTAGCCGTAGTTAGGCCAC-
CACTTCAAGAACTCTGTAGCACCGC
1201 CTACATACCTCGCTCTGCTAATCCTGT-
TACCAGTGGCTGCTGCCAGTGGC
1251 GATAAGTCGTGTCTTACCGGGTTGGACT-
CAAGACGATAGTTACCGGATAA
1301 GGCGCAGCGGTCGGGCTGAACGGGGGT-
TCGTGCACACAGCCCAGCTTGG
1351 AGCGAACGACCTACACCGAACTGAGATACCT-
ACAGCGTGAGCATTGAGAA
1401 AGCGCCACGCTTCCCGAAGGGAGAAAG-
GCGGACAGGTATCCGGTAAGCGG
1451 CAGGGTCGGAACAGGAGAGCGCACGAGG-
GAGCTTCCAGGGGGAAACGCCT
1501 GGTATCTTTATAGTCCTGTCGGGTTTCGCCA-
CCTCTGACTTGAGCGTCGA
1551 TTTTmGTGATGCTCGTCAGGGGGGCG-
GAGCCTATGGAAAAACGCCAGCAA
1601 CGCGGCCTTTTTACGGTTCCTGGC-
CTTTTGCTGGCCTTTTGCTCACATGT
1651 TCTTTCCTGCGTTATCCCCTGATTCT-
GTGGATAACCGTATTACCGCCTTT
1701 GAGTGAGCTGATACCGCTCGCCGCAGC-
CGAACGACCGAGCGCAGCGAGTC 1751 AGTGAGCGAGGAAGCGGAAGAGCGCT-
GACTTCCGCGTTTCCAGACTTTAC
1801 GAAACACGGAAACCGAAGACCATTCAT-
GTTGTTGCTCAGGTCGCAGACGT
1851 TTTGCAGCAGCAGTCGCTTCACGT-
TCGCTCGCGTATCGGTGATTCATTCT
1901 GCTAACCAGTAAGGCAACCCCGCCAGC-
CTAGCCGGGTCCTCAACGACAGG
1951 AGCACGATCATGCGCACCCGTGGCCAG-
GACCCAACGCTGCCCGAGATGCG
2001 CCGCGTGCGGCTGCTGGAGATGGCG-
GACGCGATGGATATGTTCTGCCAAG
2051 GGTTGGTTTGCGCATTCACAGTTCTCCG-
CAAGAATTGATTGGCTCCAATT
2101 CTTGGAGTGGTGAATCCGTTAGCGAGGT-
GCCGCCGGCTTCCATTCAGGTC
2151 GAGGTGGCCCGGCTCCATGCACCGC-
GACGCAACGCGGGGAGGCAGACAAG
2201 GTATAGGGCGGCGCCTACAATCCATGC-
CAACCCGTTCCATGTGCTCGCCG
2251 AGGCGGCATAAATCGCCGTGACGAT-
CAGCGGTCCAGTGATCGAAGTTAGG
2301 CTGGTAAGAGCCGCGAGCGATCCT-
TGAAGCTGTCCCTGATGGTCGTCATC
2351 TACCTGCCTGGACAGCATGGCCTG-
CAACGCGGGCATCCCGATGCCGCGG
2401 AAGCGAGAAGAATCATAATGGGGAAGGC-
CATCCAGCCTCGCGTCGCGAAC
2451 GCCAGCAAGACGTAGCCCAGCGCGTCG-
GCCGCCATGCCGGCGATAATGGC
2501 CTGCTTCTCGCCGAAACGTTTGGTG-
GCGGGACCAGTGACGAAGGCTTGAG
2551 CGAGGGCGTGCAAGATTCCGAATACCG-
CAAGCGACAGGCCGATCATCGTC
2601 GCGCTCCAGCGAAAGCGGTCCTCGC-
CGAAAATGACCCAGAGCGCTGCCGG
2651 CACCTGTCCTACGAGTTGCATGATAAA-
GAAGACAGTCATAAGTGCGGCGA
2701 CGATAGTCATGCCCCGCGCCCACCG-
GAAGGAGCTGACTGGGTTGAAGGCT
2751 CTCAAGGGCATCGGTCGGCGCTCTCCCT-
TATGCGACTCCTGCATTAGGAA
2801 GCAGCCCAGTAGTAGGTTGAGGCCGT-
TGAGCACCGCCGCCGCAAGGAATG
2851 GTGCATGTAAGGAGATGGCGCCCAA-
CAGTCCCCCGGCCACGGGGCCTGCC
2901 ACCATACCCACGCCGAAACAAGCGCT-
CATGAGCCCGAAGTGGCGAGCCCG
2951 ATCTTCCCCATCGGTGATGTCGGC-
GATATAGGCGCCAGCAACCGCACCTG
3001 TGGCGCCGGTGATGCCGGCCACGAT-
GCGTCCGGCGTAGAGAATCCACAGG
3051 ACGGGTGTGGTCGCCATGATCGCG-
TAGTCGATAGTGGCTCCAAGTAGCGA
3101 AGCGAGCAGGACTGGGCGGCGGC-
CAAAGCGGTCGGACAGTGCTCCGAGAA
3151 CGGGTGCGCATAGAAATTGCATCAACCG-
CATATAGCGCTAGCAGCACGCCA
3201 TAGTGACTGGCGATGCTGTCGGAATG-
GACGATATCCCGCAAGAGGCCCGG
3251 CAGTACCGGCATAACCAAGCCTATGC-
CTACAGCATCCAGGGTGACGGTGC
3301 CGAGGATGACGATGAGCGCATTGTTA-
GATTTCATACACGGTGCCTGACTG
3351 CGTTAGCAATTTAACTGTGATAAACTAC-
CGCATTAAAGCTAATCGATGAT
3401 AAGCTGTCAAACATGAGAATTAA (SEQ ID NO 86)

The new vector is called pIGRI2MoTAbI. A version lacking the hexahistidine tag was constructed in a similar way starting from the previous MoTAbI expressionplasmid without hexahistidine tail. The new MoTAbI expressionvectors were subsequently transferred to *E.coli* expressionstrains MC1061(pAcI), SG4044(pcI857) and UT5600 (pAcI). As expected, most of the expressed MoTAbI was present as cytoplasmic inclusionbodies. MoTAbI molecules were purified from cytoplasmic inclusion bodies under denaturing conditions followed by standard refolding procedures as described by De Bernardez Clark (1998).

4.2. Generation of MoTAb II

Figure 1A:
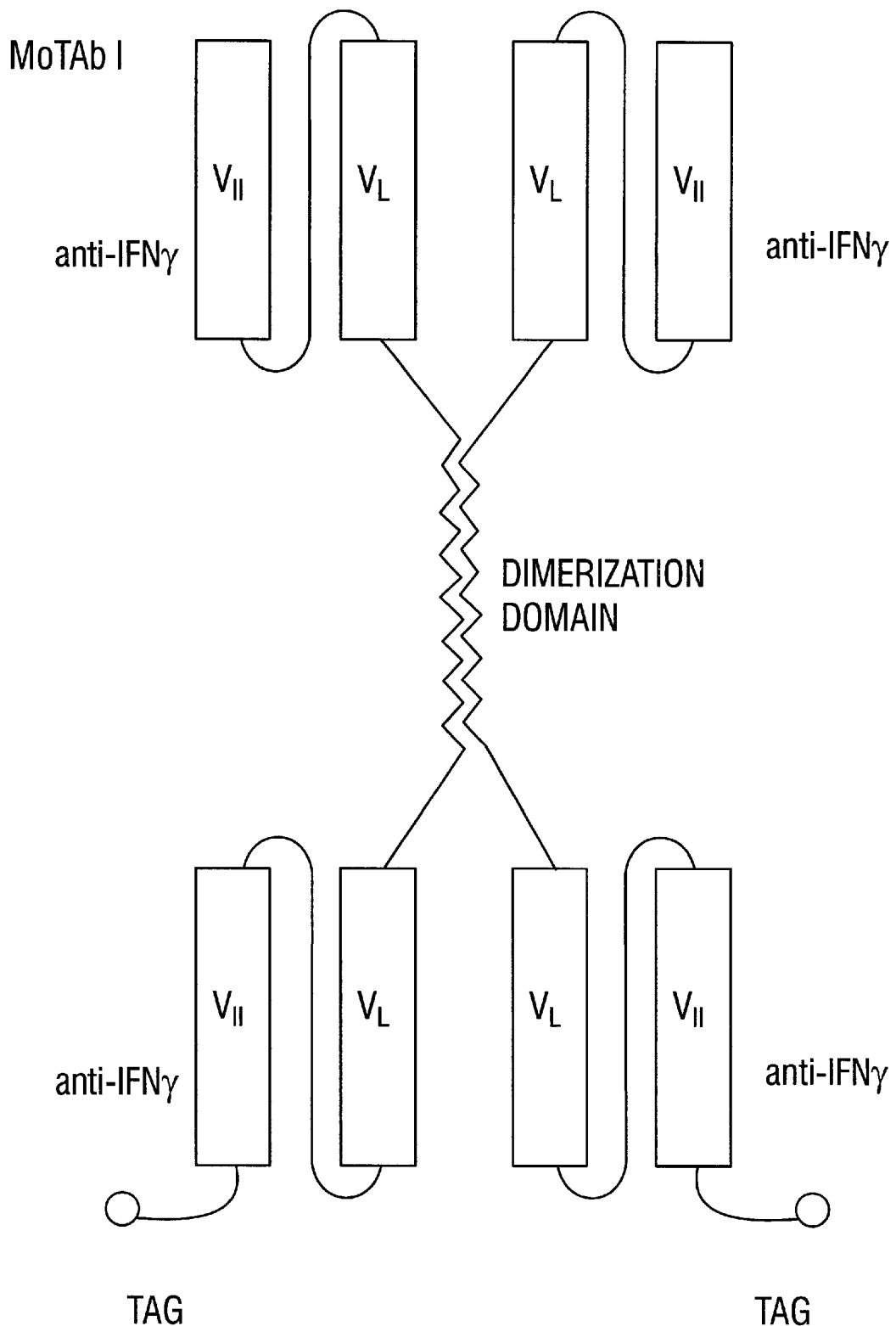
FIG. 1 schematically shows 2 different tetravalent antibody constructs (MoTAB I and MotabII). MoTAb I represents a molecule which consists of 4 identical scFv's in the format of a homodimer of 2 identical molecules, each containing 2 scFv's. MoTAb II represents a full-size antibody molecule to which 2 scFv's with the same specificity are attached at the carboxyterminus. Optionally, these constructs contain a purification/detection tag.
See also further Example 4.
Figure 1B:
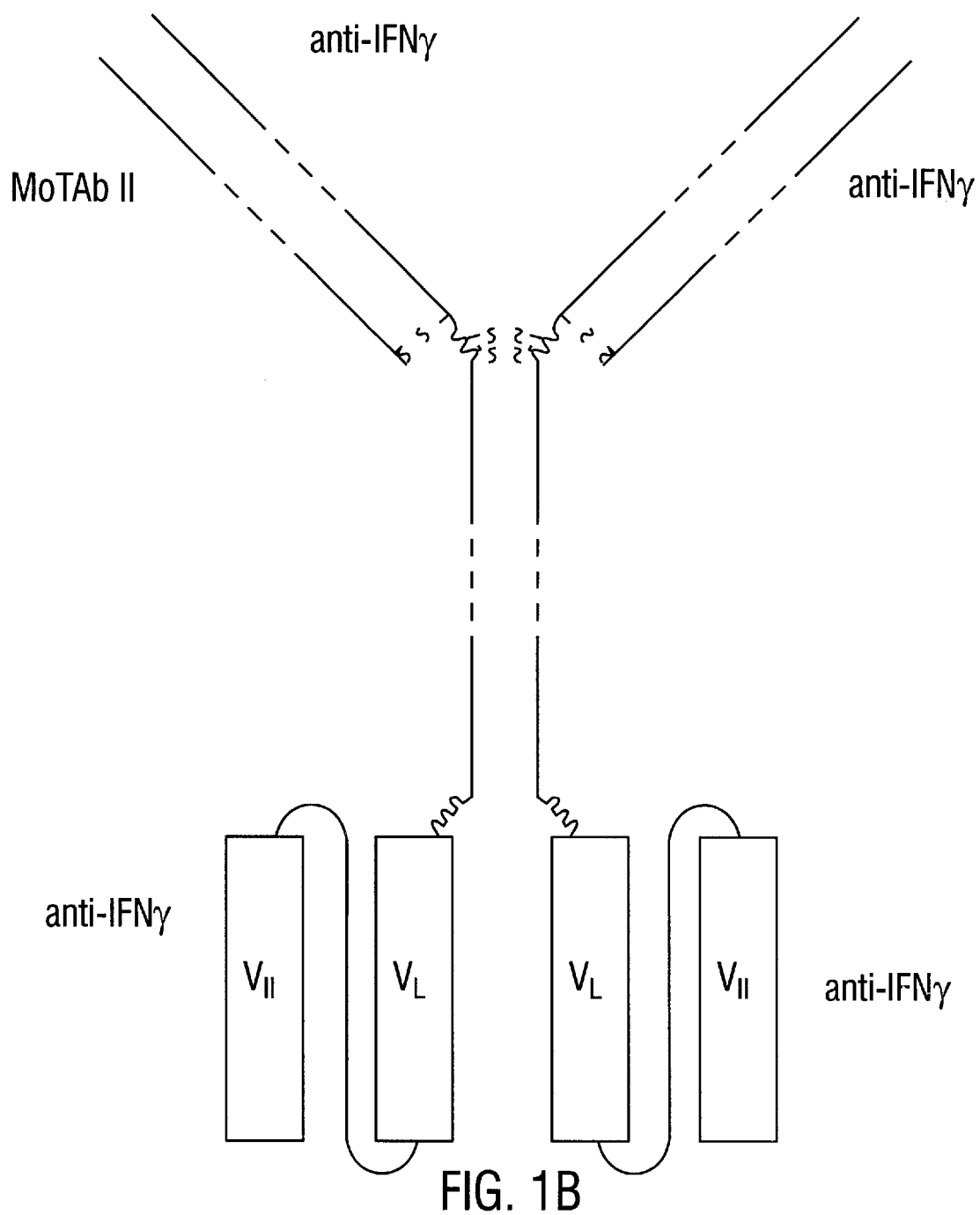
Figure 3:
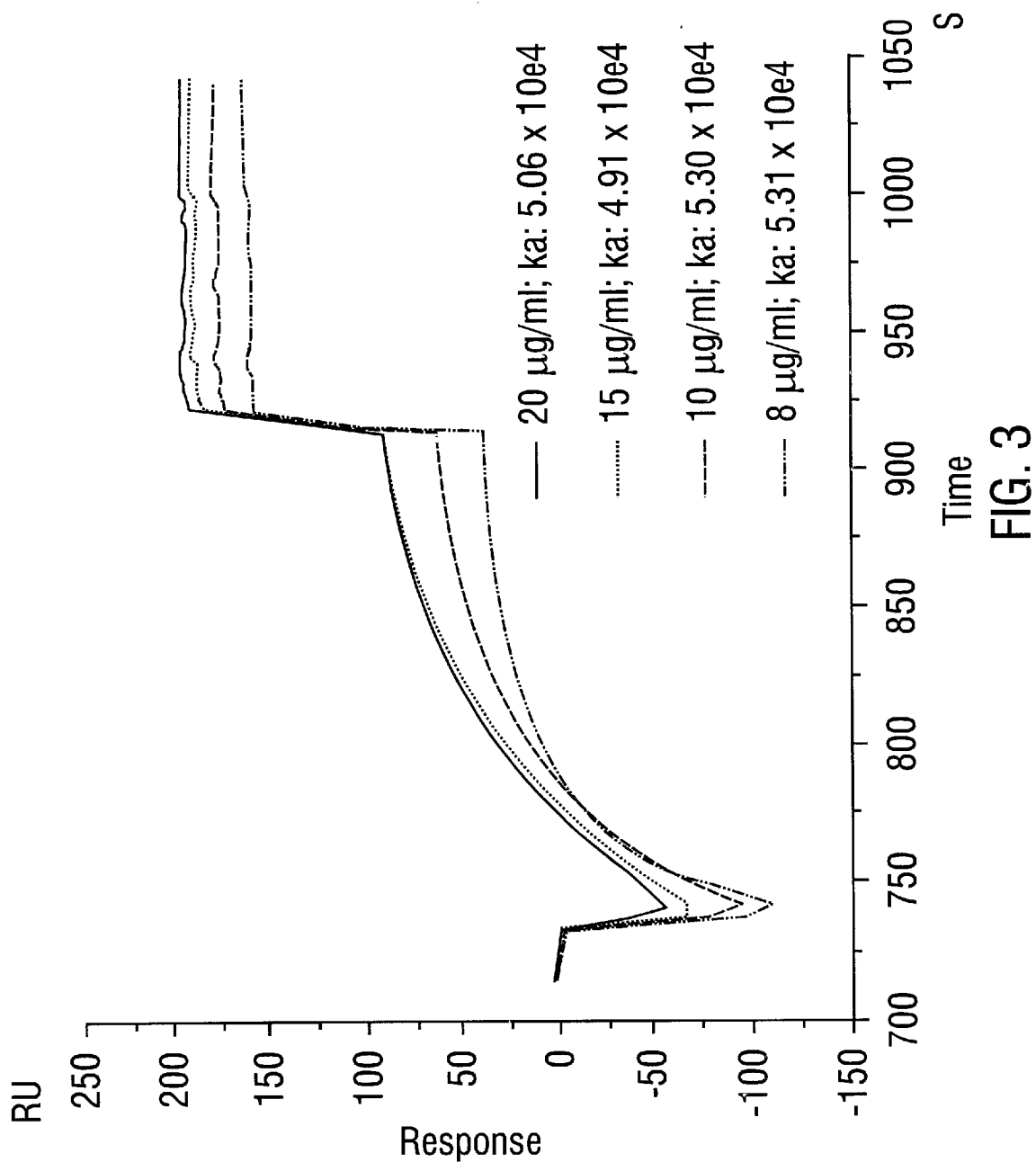
FIGS. 3 and 4 shows the binding of different concentrations of murine scFvD9D10 (FIG. 3) and humanized scFvD9D10 (FIG. 4) to human IFNγ. Human IFNγ is immobilized indirectly to the CM5 sensorchip via the murine D9D 10 full size antibody as described in example 1. Association rate constants derived from these binding curves are shown. Dissociation rate constants could not be measured accurately as dissociation is hardly detectable ($<5 \times 10^{-4}$ s$^{-1}$) in this experimental setup.
Figure 4:
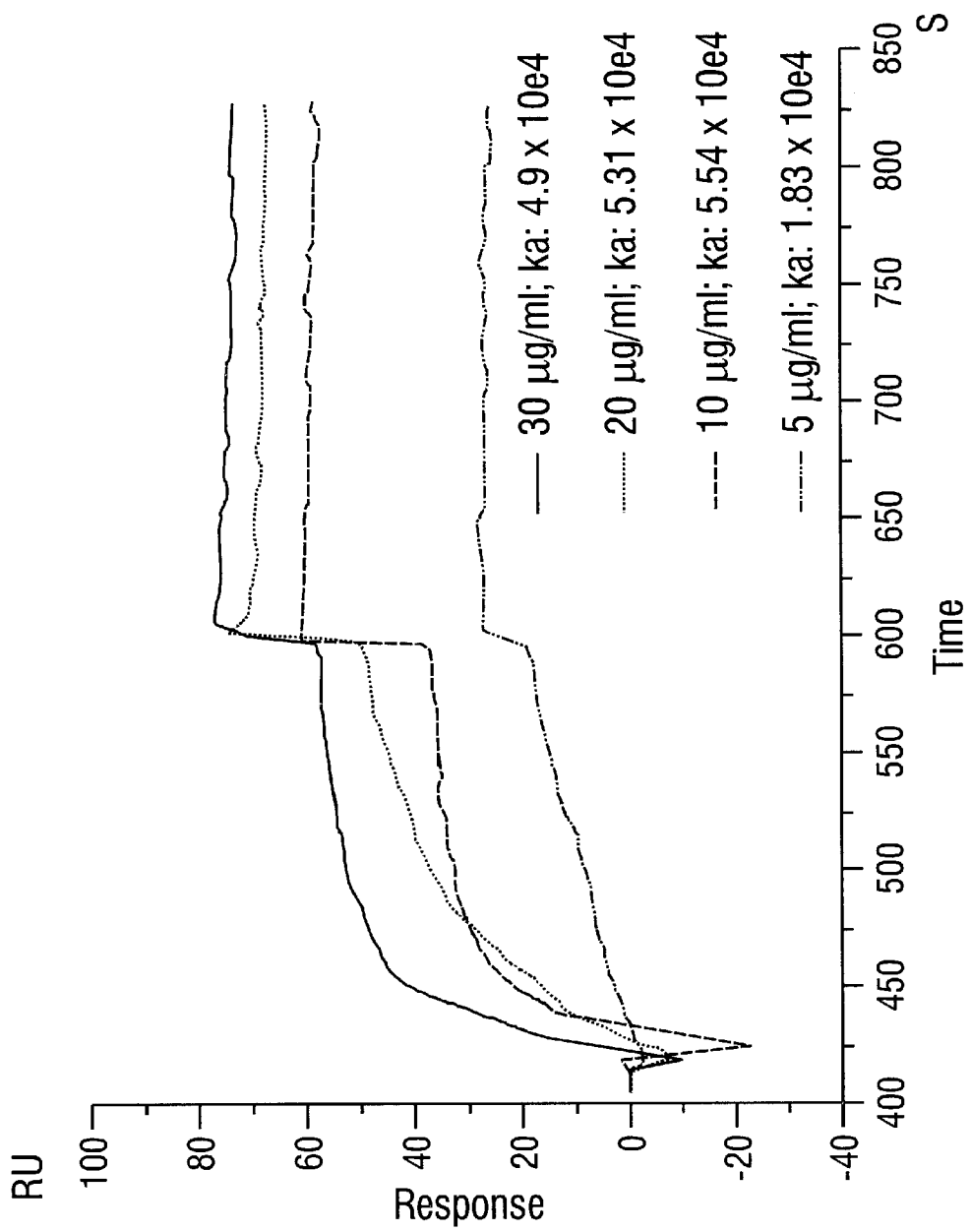

The D9D10 MoTAb II is defined as a humanized D9D10 whole antibody molecule to which a humanized D9D10ScFv sequence was attached at the carboxyterminus (CH3-domain) of the heavy chain (see FIG. 1). A comparable type of molecule has already been described in literature (Coloma and Morrison, 1997).

For the expression of the D9D10 MoTAbII protein two fusion genes, respectively coding for heavy and light chain fusion protein of the assembled antibody, were constructed. The heavy chain fusion gene consists of an immunoglobulin leader sequence (D9D 10 $V_K$ leader cDNA) followed by the humanized D9D10 heavy chain variable domain cDNA, a human IgG1 heavy chain constant domain ($C_H1$-Hinge-$C_H2$-$C_H3$) cDNA, a short $G_3S$ linker sequence (Coloma and Morrison, 1997) and the humanized D9D10 ScFv sequence. Alternative linker sequences such as the $(G_4 S)_3$ sequence or the flexible and proteolysis-resistant truncated mouse IgG3 upper hinge region (Pack & Plückthun, 1992) can be used.

The light chain fusion gene is identical to the humanized D9D10 recombinant antibody light chain gene (2) and contains the D9D10 $V_K$ leader, the humanized light chain variable domain cDNA and the human IgG1 constant domain (kappa).

Construction of MoTAb II Heavy Chain cDNA

The basic constructs generated for expression of the humanized D9D10 antibody could be used as backbone for the MoTAbII constructs. As described several intermediate cloning constructs, mainly generated by PCR-assembly and -amplification, eventually resulted in two final constructs, named pGEMhD9D10$_L$ and pGEMhD9D10$_H$. The latter plasmid was used as acceptorfragment after digestion with HindIII and EcoRI, which eliminates the STOP codon for insertion of a HindIII-EcoRI donorfragment isolated from a plasmid pGEM-T-D9D10HE, resulting in the in frame fusion of the hD9D10$_H$ cDNA to a cDNA sequence encoding the Gly$_3$Ser linker followed by the humanizedScFv-module and a STOP codon. The resulting plasmid was named pGEM-MoTAbII$_H$.

pGEM-T-D9D10HE was constructed by PCR amplification using pScFvD9D10V$_{hum}$ as template with primers IG8078 and IG8077. The resulting 755 bp PCR fragment, containing the Gly$_3$Ser linker followed by the humanized scFv-module and a STOP codon, was directly cloned in the pGEM-T vector.

Figure 13A:
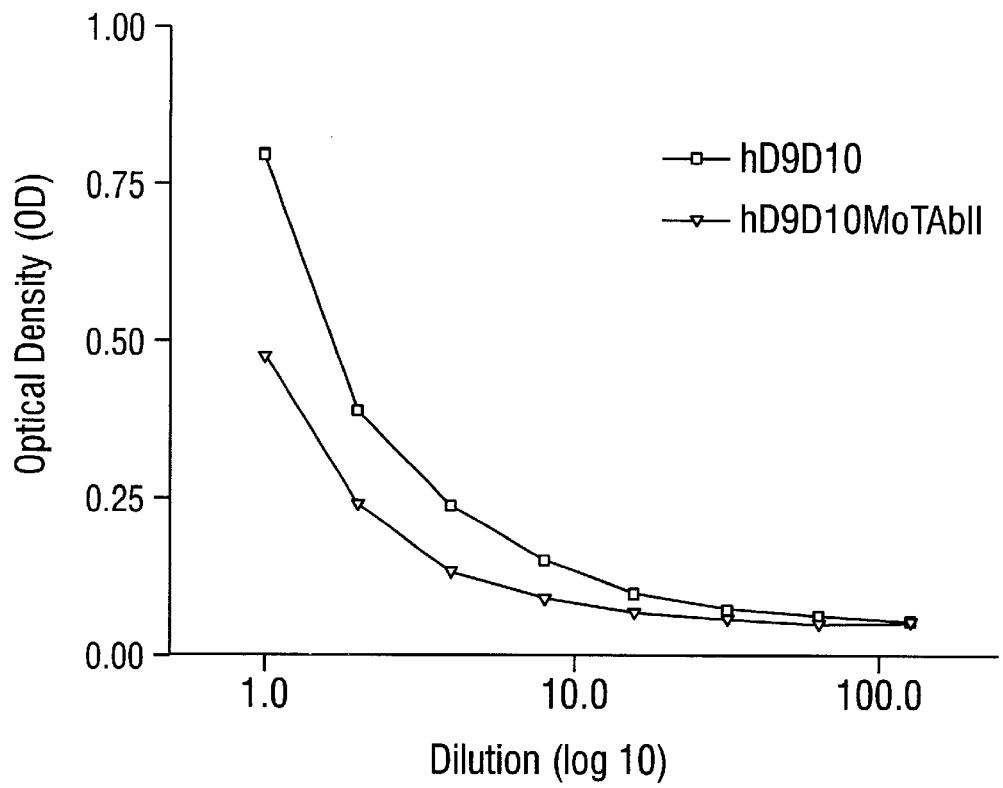
FIG. 13 shows the binding in ELISA of different concentrations of purified humanized D9D10 and MoTabII to immobilized human IFNγ. The assay is performed as described in example 2.
Figure 13B:
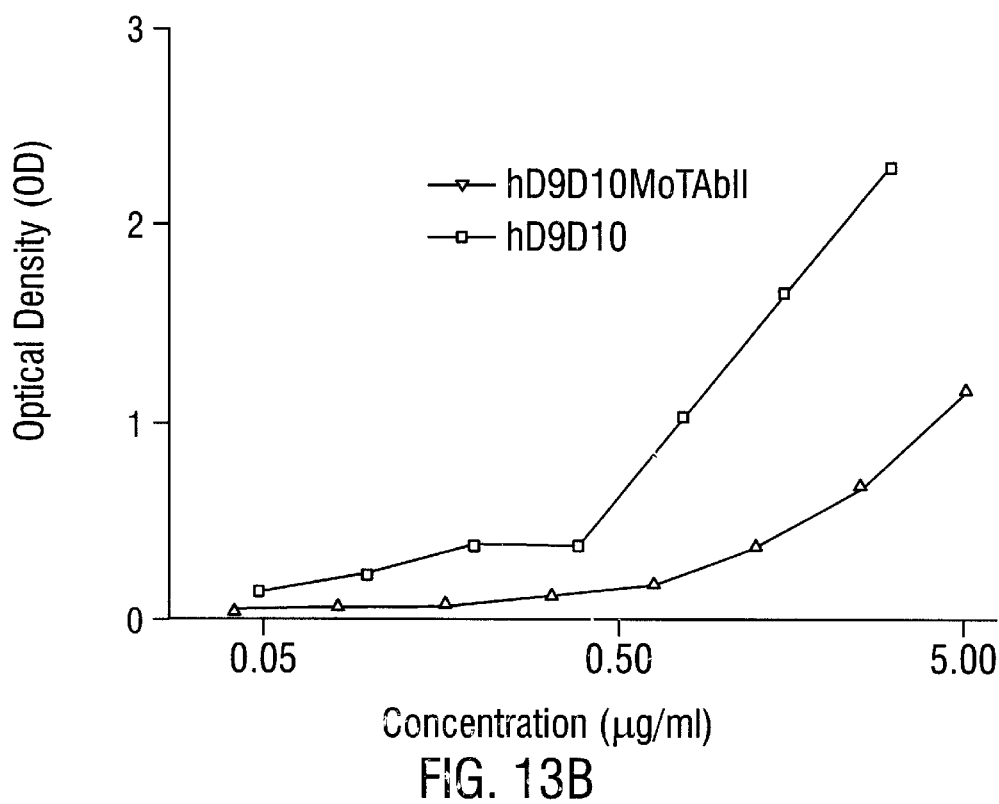

Expression in mammalian cell lines was performed completely as described for the humanized D9D10 antibody (cf example 2). The cDNA encoding the LdrV$_{Hh}$C$_H$ScFv or MoTAbII$_H$ fusion protein was initially inserted in the pEE6hCMV-BgIII (Lonza biologicals) intermediate expression vector, under transcriptional control of the hCMV promoter. This was performed by transfer of the EcoRI-XbaI DNA insert from pGEMMoTAbIIH into the pEE6hCMV-BgIII vector. From the pEE6MoTAbII$_H$ plasmid a complete mammalian expression casette, consisting of CMV-promoter followed by the fusion gene and a polyadenylation site, was then transferred as a BgIII/BamHI fragment to the BamHI opened pEE12hD9D10$_L$ and pEE14hD9D10$_L$ expression plasmids already available (construct was earlier described for the humanized D9D10 antibody construct in example 2). The final expression plasmids, named pEE12MoTAbII and pEE14MoTAbII then consisted of the pEE-backbone plasmid containing the GS-selection unit, carrying the light chain fusion gene expression casette followed by a comparable heavy chain fusion gene expression casette. A schematic representation of both plasmids is given in FIGS. 17 and 18. The approach of assembling a single expression plasmid containing separate transcription units for both heavy and light chains and the selectable marker, is adviced in order to ensure coamplification with the marker gene. The cDNA sequence encoding the complete MoTAbII heavy chain fusion protein is given in FIG. 19 (SEQ ID NO 89). The amino acid sequence of the MoTAbII heavy chain fusion protein is given in FIG. 20 (SEQ ID NO 90).

Small Scale Expression of D9D10 MoTAbII in COS Cells

Transient expression in COS monkey kidney cells was performed using both mammalian expression constructs pEE12MoTAbII and pEE14MoTAbII completely as described for the humanized D9D10 antibody (cf example 2). Quality control was performed by IFNγ-binding ELISA and SPR-analysis.

ELISA

The same set up was used as described in example 2. Results are shown in FIG. 11. Specific binding to IFNγ is detected. The signal is lower than the signal obtained with crude COS supernatant of humanized D9D10. However, no concentrations were determined of MoTAbII.

SPR Analysis

A similar set up was used as described for the evaluation of the murine and humanized scFvD9D10 derivatives. Briefly, murine D9D10 was immobilized directly onto a B1 sensorchip at a concentration of 10 μg/ml D9D10 in an acetate buffer pH 4.8 using amine coupling. A fixed concentration of 8 μg/ml human IFNγ was added, followed by the injection of either murine D9D10 (10 μg/ml; positive control) or crude COS supernatant containing MoTAb II. Results are shown in FIG. 21. These data clearly illustrate the presence of active, IFNγ binding molecules in the COS supernatant. As no exact concentrations were determined of the MoTAB II, no affinity data could be calculated.

```
                          HindIII
IG8078(sense):       5'-CCCAAGCTTGGCGGAGGCTCACAGGTGCAGCTGGTGCAGAG-3'
                        EcoRI
                     (SEQ ID NO 87)

IG8077(antisense):5'-CGGAATTCTACCGTTTGATCTCGAGTTTGG-3'
                     (SEQ ID NO 88)
*Construction of mammalian expression plasmids
```

Inhibition of MHC Class II Induction
cf Example 8.1.
Purification MoTAbII was purified using classical protein A chromatography (Perry and Kirby, 1990; Page and Thorpe, 1996). Quality control of the purified construct was done by Western Blot (classical technology) and ELISA. The latter was performed as described in example 2 and results are shown in FIG. 13. From these results we can conclude that MoTAbII is specifically interacting with human IFNγ.

Generation of Stable Mammalian Expression Cell Lines

For generation of stable mammalian expression cell line, two host cell lines Ns0 (Galfre and Milstein, 1981; ECACC 85110503) and CHO-K1 (ATCC CCL61) were used. Transfection and selection procedures were completely identical as described for the humanized D9D10 whole antibody, using the plasmids pEE12MoTAbII for NsO and pEE14MoTAbII for CHO-K1. For both NS0 and CHO-K1, several MoTAbII producing cell lines (determined in IFNγ-binding ELISA) were initially isolated and used as parental clones for further amplification of recombinant protein expression levels as described earlier.

Production of large amounts of the recombinant protein is performed on bioreactor systems optimal for the respective host cells.

5. Generation of Anti-IFNγ Diabodies

Diabodies are dimeric antibody fragments. In each polypeptide, a heavy-chain variable domain ($V_H$) is linked to a light-chain variable domain ($V_L$) but unlike scFv's, each antigen-binding site is formed by pairing of one $V_H$ and one $V_L$ domain from two different polypeptides. This is achieved by shortening the linker between the $V_H$ and $V_L$ domains in each molecule (Holliger et al., 1993). Since diabodies have two antigen-binding sites they can either be monospecific or bispecific. Monospecific bivalent molecules are generated by the shortening the flexible linker sequence of the scFv molecule to between five and ten residues and by crosspairing 2 scFv molecules with shortened linker. In order to stabilize the molecule, an optional cysteine residue can be inserted in the linker. As an example for the different steps involved in such a construction we have documented the construction of D9D10 -derived monospecific, humanized anti-IFNγ diabodies. The 15 residue linker of the His6-tagged, humanized scFvD9D10 was replaced by the 5 or 10 residue linker using overlap extension PCR. Shortly, both D9D10 $V_H$ and $V_L$ coding sequences were PCR amplified whereby the $V_H$ antisense primer and the $V_L$ sense primer have sequences coding for the 5- or 10-mer linker sequence. The resulting $V_H$ and $V_L$ PCR fragments were subsequently mixed and a second PCR with the $V_H$ sense and $V_L$ antisense primers was performed. The resulting PCR fragment is cloned into the pBSK(+) plasmid (Stratagene) en verified by DNA sequence analysis (FIGS. 22–25) (SEQ ID NO 91–94). The D9D10 diabody coding sequence was subsequently transferred as a SapI blunt/EcoRI fragment and inserted into the NcoI blunt/EcoRI opened vector pTrc99A (Amann et al., 1988). In this vector, expression of the diabodies is under control of the IPTG inducible Trc promotor. The diabodies were expressed in *E. coli* strains HB101 or JM83. Periplasmic fractions were prepared following a modified protocol described by Neu and Heppel (1965). Briefly, cells were harvested by centrifugation and resuspended in ice cold shockbuffer (100 mM Tris-HCl pH 7.4; 20% sucrose; 1 mM EDTA pH8). After incubation on ice during 10 min. with occasional stirring, the mixture was centrifuged at 10.000 rpm during 1.5 min. The supernatans was removed and the pellet was immediately resuspended in ice cold distilled water. After incubation on ice during 10 min. with occasional stirring, the mixture was centrifuged at 14.000 rpm and the obtained supernatans was the soluble periplasmic fraction. The periplasmic fractions were tested for binding to IFNγ using SPR-analysis. The experimental set up was as described in example 2. The undiluted samples were injected onto the surface of a B1 sensorchip coated with murine D9D10 onto which IFNγ was injected. Results obtained with L5 D9D10 diabodies are shown in FIG. 26. A clear, specific binding of the diabodies was detected. Comparable results were obtained with the L10 D9D10 diabody.

The bivalent, monospecific diabody molecules are purified from the periplasmic extract via IMAC or from periplasmic inclusion bodies using denaturing conditions followed by refolding.

Overlap Extension PCR Primers for the L10D9D10 Diabodies:

D9D10$V_H$ forward (sense) primer

5'GGCCGCTCTTCGAAATACCTATTGCCTAC-GGCAG3' (SEQ ID NO 95)

D9D10L10$V_H$ backward (antisense) primer

5'-CTGGGTCAGTACGATGTCAGAGCCAC-CTCCGCCTGAACCGCCTCCACCTGAG-GAGACGGTGACCGTGGTC-3' (SEQ ID NO 96)

D9D10L10$V_L$ forward (sense) primer

5'-GTCACCGTCTCCTCAGGTGGAGGCGGT-TCAGGCGGAGGTGGCTCTGACATCG-TACTGACCCAGAGCC-3' (SEQ ID NO 97)

D9D10$V_L$ backward (antisense) primer

5'-GCCAGTGAATTCTATTAGTGGTGATG-3' (SEQ ID NO 98)

Overlap Extension PCR Primers for the L5 D9D10 Diabodies:

D9D10$V_H$ forward (sense) primer

5'-GGCCGCTCTTCGAAATACCTATTGCCTAC-GGCAG-3' (SEQ ID NO 95)

D9D10L5$V_H$ backward (antisense) primer

5'-CTGGGTCAGTACGATGTCTGAACCGC-CTCCACCTGAGGAGACGGTGACCG-TGGTC-3' (SEQ ID NO 99)

D9D10L5$V_L$ forward (sense) primer

5'-GTCACCGTCTCCTCAGGTGGAGGCGGT-TCAGACATCGTACTGACCCAGAGCC-3' (SEQ ID NO 100)

D9D10$V_L$ backward (antisense) primer

5'-GCCAGTGAATTCTATTAGTGGTGATG-3' (SEQ ID NO 98)

6. Generation of Anti-IFNγ Triabodies

The construction of triabody molecules was analogous to the scheme described above for diabody molecules, except that the $(G_4S)_3$ linker between the humanized D9D10 VH and VL was completely deleted (FIGS. 27 and 28) ( SEQ ID NO 101–102) (zero-residue linker or –1-residue linker according to the Kabat numbering (Kortt et al., 1997; Iliades et al., 1997) ). The humanized D9D10 triabody construct is a mono-specific molecule resulting from the spontaneous association of three zero-residue linker (or –1-residue) D9D10 scFv molecules in the bacterial periplasm. A trimer was formed whereby three pairs of $V_H$ and $V_L$ domains interact to form three active antigen combining sites. If necessary, in order to drive triabody formation as well as to maintain stability, we can explore the possibility of introducing additional association domains or disulfide bridges.

The produced triabodies were tested for IFNγ binding using SPR-analysis. Periplasmic fractions were prepared as described in example 5. SPR-analysis was performed as described in example 5. Results are shown in FIG. 29. A clear, specific binding of the triabody was obtained.

The triabody molecules were purified from the periplasmic extract, made from uninduced bacterial cultures, via IMAC and further by gel filtration or alternatively by purification under denaturing conditions from periplasmic inclusionbodies followed by refolding. The multimeric behaviour of the purified molecules was analysed. The ability of the purified triabody to bind human interferon γ was tested using SPR-analysis and ELISA experiments as described earlier. For these tests we produced milligram amounts of highly purified material in a suitable *E.coli* expression system.

Overlap Extension PCR Primers for the L0 D9D10 Triabodies:

D9D10$V_H$ forward (sense) primer

5'-GGCCGCTCTTCGAAATACCTATTGCCTA-
    CGGCAG-3'                                      (SEQ ID NO 95)

D9D10L0$V_H$, backward (antisense) primer

5'-CTGGGTCAGTACGATGTCTGAGGAGACG-
    GTGACCGTGGTC-3'                               (SEQ ID NO 103)

D9D10L0$V_L$ forward (sense) primer

5'-GTCACCGTCTCCTCAGACATCGTACTG-
    ACCCAGAGCC-3'                                 (SEQ ID NO 104)

D9D10$V_L$ backward (antisense) primer

5'-GCCAGTGAATTCTATTAGTGGTGATG-3'   (SEQ ID NO 98)

7. Generation of MoTAb's (and BiTAb's) Originating from Fusion Proteins, from Serum Multisubunit Proteins and from scFv's The multi subunit (oligomeric) structure of proteins may be exploited to obtain multivalent antibodies, when they are used as fusion partner with scFv antibodies. Either the whole polypeptide chain, or the association sequence domain may be used as fusion partner.

For example, haemoglobin is a tetrameric serum protein, consisting from 2 alpha and 2 beta globin subunits. The dimer dissociation constant is estimated to be in the order of 1 nM (Pin et al., 1990). The tetramer—dimer dissociation constant of haemoglobin in oxy-conformation was studied by gel filtration on Superose 12 and was calculated to be 1 $\mu$M (Manning et al, 1996). Although non-covalent associations are known to be susceptible to equilibrium rules, it has been described that the subunit interactions are favoured in concentrated protein solutions like serum and also may be increased by the presence of other stabilising compounds (Srere and Mathews, 1990).

Recombinant haemoglobin expression has been extensively investigated as a possible blood substitute in order to circumvent the transmission of infectious disease agents during blood transfusion. The alpha- and beta-globin polypeptides have already been expressed from a single operon in *E. coil* (Hoffman et al., 1990). In this case, the recombinant haemoglobin was purified from the soluble cytoplasmatic fraction and the tetrameric *E. coli* product had essentially the same characteristics as the native protein. Analogous results were obtained when recombinant haemoglobin was expressed in *S. cerevisiae* (Pagnier et al., 1992; Mould et al., 1994; Sutherland-Smith et al., 1998).

Protein engineering strategies (Olson et al., 1997) and chemical modification by pegylation (Pettit and Gombotz, 1998) are investigated to enhance the stability and the circulation half times in vivo. So fusion of relevant scFv molecules to the respective alpha and beta subunit of human haemoglobin and expression of the fusion proteins from a single operon in either *E. coli* or *S. cerevisiae* would yield a functional tetrameric monospecific (if identical scFv's are used) or bispecific (when different scFv's are used) molecules at high level.

8. Evaluation of Anti-IFNγ Neutralizing Molecules
8.1. Inhibition of MHCII-induction In the first experiments, the effect of IFNγ on the induction of MHC class II expression on human keratinocytes was examined. For this, primary human keratinocytes (passage 1) were cultured with two concentrations of human IFNγ (100 U/ml and 200 U/ml) during 24 and 48 hours. After culture, cells were collected and the expression of MHC class II antigen on the activated keratinocytes was measured by FACS-scan after staining (30 minutes at 4° C.) of the cells with a PE-labelled anti-MHC-class II mAb. The results showed that resting keratinocytes do not express MHC class II molecules and that IFNγinduces the expression after 24 hours in a dose-dependent way. The induction is still enhanced after 48 hours of culture.

In the next study, the effect of anti-human IFNγD9D10H3 full size antibody or scFvD9D10-cmyc on the IFNγ-induced MHC-Class II expression on human keratinocytes was examined. In this experiment, human primary keratinocytes (passage 1) were cultured with human IFNγ (100 U/ml) in the presence or absence of different concentrations (2–0.5–0.12–0.03) D9D10 Ab or D9D10scFv for 48 hours. IFNγ was preincubated with D9D10H3 or scFvD9D10 during 1 hour at 37° C. before adding to the keratinocytes. After culture, cells were collected and the expression of MHC-Class II on these activated keratinocytes was measured. For this, keratinocytes were incubated (30 minutes at 4° C.) with a PE-labelled anti-MHC-ClassII mAb (Becton Dickinson), washed twice with PBS and fixed. The MHC-Class II expression was further analysed on a FACS-scan. The results of these experiments are represented in FIG. 30. It is shown that the MHC class II antigen is not expressed on the membrane of resting keratinocytes and that IFNγ clearly induces this MHC class II expression. This IFNγ induced MHC class II expression is dose dependently inhibited by D9D10H3 and to a lesser extent by scFvD9D10. We can conclude that about 4 times more scFv (0.12 $\mu$g/ml) than full size antibody (0.5 $\mu$g/ml) is needed to obtain a 50% inhibition of the IFNγ-induced MHC class II expression on keratinocytes.

Similar experiments were performed in order to evaluate the neutralization capacity of humanized D9D10 and MoTAbII. Results are summarized in FIG. 31. Although in this experiment, MHC class II induction could be only induced to a lesser extent, both humanized D9D10 and MoTAbII clearly inhibit the IFNγ-induction.

8.2. Inhibition of Anti-viral Activity

For neutralization of the antiviral activity of hIFNγ, serial dilutions of samples (anti-IFNγ constructs) were prepared in microtiter plates. To each well, hIFNγ was added to a final concentration of 5 antiviral protection Units/ml, as tested on A549 cells. The mixtures were incubated for 4 h at 37° C. and 25000 A549 cells were added to each well. After an incubation period of 24 at 37° C. in a $CO_2$ incubator, 25 μl of $8\times10^5$ PFU EMC virus/ml was added to the cultures for at least 24 h. As soon as virus-infected control cultures reached 100% cell destruction, a crystal violet staining was performed in order to quantify surviving cells. The neutralization capacity of the anti-IFNγ constructs was defined by the concentration of the construct needed to neutralize 95% of the antiviral activity of 5U/ml human IFNγ. The neutralization potency of the scFvD9D10 and the humanized scFvD9D10 was determined and was 1.2 μg/ml and 1.5 μg/ml, respectively.

8.3. Beneficial Effects in Septic Shock in Mice

Septic shock has been demonstrated to be a complex human disease manifestation that occurs after the release of lipopolysaccharide (LPS) into the circulation. The subsequent production of high cytokine levels in the serum are known to play a crucial role in septic shock. We generated data in a mouse model system using an anti-mouse IFNγ called F3 (Froyen et al., 1995).

The generalized Shwartzman model is a lethal shock syndrome in experimental animals which is elicited by 2 consecutive injections of LPS. In the laboratory of prof. Billiau (Rega Institute, Catholic University Leuven, Belgium), such a model was developed in mice (Billiau et al., 1987). At time 0, the mice were injected with 5 μg LPS into the footpad, followed 24 h later by a second intravenous injection of 100 μg. Morbidity and mortality was scored for 5 days. Untreated animals normally died within 2 days after the second injection. Mice pretreated with the anti-muIFNγ antibody F3 were completely protected against the lethal effect and only showed moderate disease symptoms. This protection could be achieved with as little as 2.4 μg F3 given 24 h before the first injection. In order to score the severity of the disease, the symptoms were classified in 5 groups:

Score 0: not sick or mild piloerection

Score 1: piloerection and diarrhoea

Score 2: hemorhagic conjunctivitis and bleeding at the mouth and anus

Score 3: paralysis of the hind legs

Score 4: death

The highest score that could be obtained is 4. Since the number of mice in each group was relatively low (5), we established a limit of the disease score (=2) that had to be reached in the saline group in order to be a representative experiment.

The schedule we used in order to compare F3 and its scFv in this Shwartzman model was as follows: NMRI mice were given the preparative dose of 5 μg LPS at time 0. At the time points +6 h, +12 h and +23 h the mice were injected ip with 190 μg scFvF3 (Froyen et al., 1995) or 30 g F3. Control animals were given saline at the same time points. Each group consisted of 5 mice. The mice were given a score according to the above mentioned classification.

In the first experiment, 40% more mice were protected in the scFvF3 group when compared with the control group. A second experiment was set up using a slightly adapted protocol: an additional injection was given at timepoint +3 h. The result of this experiment (shown in table) was similar to that of experiment 1 in that 40% more mice survived in the scFvF3 group in comparison with the control group as can be seen in FIG. 32. In addition to scFvF3, a Fab antibody fragment of F3 was included in the second group. All these mice survived the experiment.

The mean disease scores of these experiments, demonstrate a significant difference for both F3 and the scFv compared to the control group. The mean disease scores of the 5 mice of each group were as follows:

|  | Saline | scFvF | 3F3 | FabF3 |
| --- | --- | --- | --- | --- |
| exp. 1 | 3.2 | 1.8 | 0.0 | ND |
| exp. 2 | 2.6 | 0.8 | 0.6 | 0.6 |

8.4. Beneficial Effects During Cachexia in Mice

In a model for cachexia developed at the Rega Institute (Matthys et al., 1991), nude mice were injected intraperitoneally (ip) with CHO cells producing mouse IFNγ (Mick cells). Mice receiving CHO-Mick cells will exhibit cachexia (including body weight loss) within 48 hours. The cachectic effect is correlated with the number of Mick cells. Thus with small tumor cell inocula ($0.8-3.0\times10^7$ cells), cachexia is transient and mice will completely recover. However, with high inocula ($>3.4\times10^7$ cells), mice continue to loose weight and will die within 7 days. It is shown that IFNγ plays an essential role in the pathogenesis of the Mick-induced cachexia as monoclonals against IFNγ can reverse the wasting effect: pretreatment (day −1) with the anti-muIFNγ antibody F3 inhibits cachexia.

In order to compare the effects of F3 and its scFv on the established cachexia model, the following experiment has been set up: mice were injected with $2-4\times10^7$ Mick cells on day 0 and antibody preparations were administered ip at time points +1.5 h, +6 h, +22 h and +66 h relative to the time of Mick cell inoculation. For scFvF3, a dose of 190 μg was given each injection while for F3, 40 μg was given. Control animals were injected with saline at the same time points. In each group, 3 or 4 mice were used. Mice were weighed for 10 consecutive days and mortality was scored. The results of 2 independent experiments are shown in FIG. 33. The mice treated with scFvF3 were better protected against the cachectic effect than the control mice.

These results also indicate that scFvF3 antibody fragments do have a protective effect of cachexia but to a lesser extent than the parental F3 antibody. Although results were promising, it was clear that the effect of the scFv fragment was limited either due to its fast clearance or to lowered affinity. Optimization of the injection schedule was needed to obtain comparable results.

8.5. Beneficial Effects in Septic Shock in Non-human Primates

The best documented sepsis model in non-human primates is the one in which baboons are given lethal infusions of *E.coli*. As described by Creasey et al. (1991), response to lethal *E.coli* challenge occurs in 3 stages: an inflammatory stage marked by a fall in white blood cell count (0–2 hr) and the appearance in plasma of TNFα, IL-1β and IL-6; a coagulant stage marked by a fall in fibrinogen concentration (2–6 hr); and a hypoxic cell injury stage marked by a rise in SGPT/BUN and by a gradual cardiovascular collapse, and death (6–24 hr).

Since the baboon animal model was not readily available, we are establishing a comparable rhesus monkey model.

D9D10 and derived constructs interacted well with rhesus IFNγ as determined in an antiviral bioassay (set up as described in example 7.2.).

Septic shock can be induced by infusion either of life bacteria or of endotoxin in sedated monkeys. After administration of different concentrations of the D9D10 anti-hIFNγ derivatives, several parameters are monitored including:

- mortality (should be 100% in control (non-treated) group)
- pathophysiology
- serum concentration of cytokines such as TNFα, IL-1 and IL-6 using ELISA or bioassay (Villinger et al., 1993)
- endotoxin profile using the limulus amoebocyte lysate assay 8.6. Beneficial Effects During Experimental Autoimmune Encephalomyelitis in Non-human Primates A. Pharmacokinetics of D9D10 and derivatives in monkey and effect on hIFNγ clearance The clearance of the antibody derivatives is of importance as molecules with a slow clearance have a prolonged efficacy. This implicates that less material has to be injected which is better for the patient and which is cost effective, especially when a longer treatment period is advisable. Therefore, complexes of IFNγ and D9D10 derivatives are used in clearance studies in non-human primates as a prerequisite to guide further in vivo studies in these animals.

The clearance of D9D10, scFvD9D10H6$^-$, D9D10 MOTAB I and D9D10 MOTAB II, is monitored after a bolus injection in healthy marmoset. Specific ELISA's are used for monitoring; no labelling of the antibody constructs is required.

Blood clearance of radiolabelled marmoset IFNγ after a bolus intravenous injection alone or in combination with one of the antibody constructs are also performed.

B. Beneficial Effects of the D9D10 Antibody Constructs on EAE in Non-human Primates In order to evaluate the therapeutic potential of the anti-IFNγ Mab D9D10 and derivatives, we are testing this antibody in a relevant non-human primate model for MS as the final step in our preclinical research. This model is required since the antibody is not cross-reacting with IFNγ from rodents and the biological activity of IFNγ is very species specific (huIFNγ is not active on cells other than human or non-human primates (Terrell and Green, 1993)). D9D10 and derived constructs interact well with marmoset IFNγ as determined in an antiviral bioassay (set up as described in example 7.2.) and using surface plasmon resonance (set up as described in example 1).

The EAE model is chosen as it is a generally accepted model for Multiple Sclerosis. We opt for the EAE model in common marmoset (*Callithrix jacchus*) as it is well developed (Massacesi et al., 1995; Genain et al., 1995), it has a pathology of MR-detectable lesions which reflects those in MS and the model shows a high incidence of EAE induction with a chronic progressive/relapsing-remitting course.

Acute PK-Tox

A limited PK-Tox study required by ethical prescriptions in all research involving non-human primates, is set up in order to test the toxicity of the substances administered either intravenously or in the lumbar cerebrospinal fluid (CSF), as the contribution of systemic and/or local IFNγ to the development of the disease is still unclear. Relatively high concentrations of the antibody preparations, especially for the scFv, are injected intravenously as one of our goals is to reach therapeutical concentrations in the CNS. Although it is known that BBB leakage occurs at the site of inflammation ('t Hart, personal communication ), a positive concentration gradient will be beneficial.

Timing of the Study

Determination of the baseline parameters is done 1 week prior to administration of the study drug. Animals are observed for signs of toxicity for 30 days. During this period pharmacokinetic parameters are monitored. Six weeks after the administration of the study drug an additional blood sample is collected to determine whether or not the animals mounted an immune response to any of the D9D10 constructs or to recombinant marmoset IFNγ.

Parameters

During This Study the Following Parameters are Determined

Clinical Monitoring

| | |
|---|---|
| Daily | Food consumption |
| Weekly | Body weights |
| Day 14, 28 | Haematology |
| | Clinical chemistry |
| | Urine analysis |

Immunological Monitoring

Serum and CSF levels of humanized D9D10, MoTAbI and II or IFNγ are measured at different time points. When severe toxicity occurs in one of the animals, the animal are sacrificed and subjected to a detailed necropsy, in order to determine whether this toxicity is drug related.

Diffusion of D9D10 Derivatives into the Lesions

As both systemically and locally (in the brain) produced IFNγ can have a disease promoting role in EAE, antibody derivatives must be able to neutralize both. Consequently, transudation of the D9D10 derivatives into the lesions in brain and spinal cord is necessary for a local effect on IFNγ. However, it is known that in MS the blood brain barrier is impaired in a subset of the active brain lesions for a limited period of time. More specifically, BBB breakdown is reflecting the state of inflammation (Hawkins et al., 1990).

The differential ability of the anti-IFNγ constructs to enter the brain is crucial for the choice of the component(s) which will be used for evaluation of the therapeutic efficacy of an anti-IFNγ treatment in EAE.

The entry of the constructs into the brain compartment is measured by post-mortem magnetic resonance imaging (MRI)-scan of the brain and the spinal cord of a relapsing monkey, injected intravenously with a gadolinium-diethylene-triamine pentaacetic acid (Gd-DTPA)-labelled D9D10 construct 1 hour prior to sacrifice. MRI-scans are compared and are related to an MRI-scan taken just before death after an injection with a small gadolinium salt that easily enters through leakages in the BBB (Gonzalez-Scarano et al., 1987; Hawkins et al., 1990; Youl et al, 1991).

These results reveal which D9D10 construct most easily enters the brain and which molecule eventually enters the active lesions where the BBB is already restituted.

Therapeutic Treatment of Marmoset Monkeys Undergoing EAE Disease Relapse

The therapeutic effect of either systemically or locally administered anti-IFNγ on the outcome of EAE in marmoset is evaluated. The start of the treatment of the monkeys is situated at the beginning of the first relapse of EAE, which usually occurs several months after the initial immunization. During the experiment the following observations, analysis and measurements are carried out as of the time of relapse.

Clinical Monitoring

- The severity of EAE is scored daily on an arbitrary scale modified from Massacesi et al. (1 995)
- Body weight and body temperature (at time of blood sampling)

Behavioural tests for monitoring the failure of neurological functions Magnetic resonance imaging (MRI) of the CNS Biochemical parameters: neopterin (specifically formed in activated macrophages) is measured in urine Immunological Monitoring At several indicated time points serum is taken to monitor the blood levels of the antibody constructs or IFNγ and to monitor the marmoset anti-mouse or anti-IFN response.

Pathology

MRI-guided histopathology analysis has proven a powerful tool for detailed analysis of MR-detectable lesions with histological methods. Briefly, at a chosen moment but preferably shortly after in vivo MR-images have been recorded, the monkey are euthanised. The brain and spinal cord is carefully excised and fixed in toto for 3 days in 4% buffered formaldehyde. Then a T2-weighted scan is made in axial and coronal direction, with a slice thickness of 1 mm covering the whole brain. For orientation of the axial slices of in vivo and in vitro images the anterior and posterior tips of the corpus callosum are used as internal reference points.

The excellent structural conservation and the high resolution of the MR-image make accurate three-dimensional localisation of potential lesions possible. Regions of interest are subsequently excised and histologically analysed for infiltrating cells (Haematoxylin-eosin), demyelisation (KLB staining of myelin lipids) and axonal structure (silver impregnation acc. to Boielschowsky).

One half of an excised brain and spinal cord is snap-frozen in liquid nitrogen. Thin cryosections are made and processed for immunohistology staining, such as for visualisation of cytokine secreting cells (especially IFNγ) or for phenotyping of infiltrated or tissue cells.

8.7. Beneficial Effects of Anti-IFNγ Antibody Constructs in Crohn's Disease

A. In vitro Assay Using Patient-derived Lymphocytes and Antigen Presenting Cells Lymphocytes isolated from either peripheral blood or surgical specimen (lamina propria or ileum E) from patients with Crohn's disease, are used for assessment of cytokine profile, lymphotyping, and functional cytotoxicity. The latter is performed by adding patient-derived antigen presenting cells and measuring the cytokine profile. The effect of anti-IFNγ derived antibody constructs on cytokine production is measured.

B Anti-IFNγ Treatment of Crohn's Disease

Patients with active Crohn's disease are infused with anti-IFNγ in a dose ranging from 1 to 20 mg/kg. Responders in the study may continue to receive repeated doses of anti-IFNγ. In all patients, clinical responses are observed and Crohn's disease activity index (CDAI) is determined.

REFERENCES

The following references, to the extent that they provide exemplary procedural or other details supplementary to those set forth herein, are specifically incorporated herein by reference.

Allen S. J., Baker D., O'Neill J. K., Davison A. N. and J. L. Turk (1993) Isolation and characterization of cells infiltrating the spinal cord during the course of chronic relapsing experimental allergic encephalomyelitis in the Biozzi AB/H mouse. Cell. Immunol. 146: 335–350.

Amann E., Ochs B. & Abel K. J. (1988) Tightly regulated tac promoter vectors useful for the expression of unfused and fused proteins in *Escherichia coli*, Gene, 69: 301–315.

Arenberger P., Ruzicka T. and L. Kemeny (1991) Effect of cyclosporin on epidermal 12(S)-hydroxyeicosatetraenoic acid binding sites. Skin Pharmacol. 4:272–277.

Asadullah K., Renz H., Docke W. D., Otterbach H., Wahn U., Kottgen E., Volk H. D. and W. Sterry (1997) Verrucosis of hands and feet in a patient with combined immune deficiency. J. Am. Acad. Dermatol. 36:850–852.

Barker J. N., Goodlad J. R., Ross E. L., Yu C. C., Groves R. W. and D. M. MacDonald (1993) Increased epidermal cell proliferation in normal human skin in vivo following local administration of interferon-gamma. Am. J. Pathol. 142: 1091–1097.

Bebbington C. R., Renner G., Thomson S., King D., Abrams D. And G. T. Yarranton (1992) High-level expression of a recombinant antibody from myeloma cells using a glutamine synthetase gene as an amplifiable selectable marker. Biotechnology 10:169–75.

Bienvenu J., Doche C., Gutowski M. C., Lenoble M., Lepape A. and J. P. Perdrix (1995) Production of proinflammatory cytokines involved in the TH1/TH2 balance is modulated by pentoxifylline. J. Cardiovasc. Pharmacol. 25: S80–S84.

Billiau A. (1996) Interferon-γ: biology and role in pathogenesis. Advances in Immunology 62: 61–130.

Billiau A., Heremans H., Vandekerckhove F. and C. Dillen (1987) Anti-interferon-gamma antibody protects mice against the generalized Shwartzman reaction. Eur. J. Immunol. 17: 1851–1854.

Billiau A., Heremans H., Vandekerckhove F., Dijkmans R., Sobis H., Meulepas E. and H. Carton (1988) Enhancement of experimental allergic encephalomyelitis in mice by antibodies against IFN-γ. J. Immunol. 140: 1506–1510.

Boissier M-C, Chiocchia G., Bessis N., Hajnal J., Garotta G., Nicoletti F. and C. Fournier (1995) Biphasic effect of interferon-γ in murine collagen-induced arthritis. Eur. J. Immunol. 25: 1184–1190.

Bone R. C. (1992) Toward an epidemiology and natural history of SIRS (systemic inflammatory response syndrome). JAMA 101: 1481–1483.

Brown R. R., Ozaki Y., Datta S. P., Borden E. C., Sondel P. M. and D. G. Malone (1991) Implications of interferon-induced tryptophan catabolism in cancer, auto-immune diseases and AIDS. Adv. Exp. Med. Biol. 294:425–435.

Bucklin S. E., Russell S. W. and D. C. Morrison (1994) Participation of IFN-γ in the pathogenesis of LPS lethality. Bacterial Endotoxins: Basis Science to Anti-Sepsis Strategies, pp. 399–406, Wiley-Liss.

Casey J. L., Keep P. A., Chester K. A., Robson L., Hawkins R. E., and R. H. J. Begent (1995) Purification of bacterially expressed single chain Fv antibodies for clinical applications using metal chelate chromatography. J. Immunol. Methods 179: 105–116.

Chan L. S. and K. D. Cooper (1994) A novel immune-mediated subepidermal bullous dermatosis characterized by IgG autoantibodies to a lower lamina lucida component. Arch. Dermatol. 130:343–347.

Chomczynski P. And Sacchi N. (1987) Single-step method of RNA isolation by acid guanidinium thiocyanate-phenol-chloroform extraction. Anal. Biochem. 162: 156–159.

Cockett M. I., Bebbington C. R. and G. T. Yarranton (1990) High level expression of tissue inhibitor of metalloproteinases in Chinese hamster ovary cells using glutamine synthetase gene amplification. Biotechnology 8: 662–7.

Coloma M. J. and S. L. Morrison (1997) Design and production of novel tetravalent bispecific antibodies. Nature Biotech. 15: 159–163.

Courtney L. P., Phelps J. L. and L. M. Karavodin (1994) An anti-Il-2 antibody increases serum halflife and improves anti-tumor efficacy of human recombinant interleukin-2. Immunopharmacol. 28: 223–232.

Creasey A. A., Stevens P., Kenney J., Allison A. C., Warren K., Catlett R., Hinshaw L. and F. B Taylor Jr (1991) Endotoxin and cytokine profile in plasma of baboons challenged with lethal and sublethal *Escherichia coli*. Circ. Shock. 33: 84–91.

De Bernardez Clark E. (1998) Refolding of recombinant proteins. Current Opinion in Biotechnology 9: 157–163.

de Kruif J. and T. Logtenberg (1996) Leucine zipper dimerised bivalent and bispecific scFv antibodies from a semi-synthetic antibody phage display library. J. Biol. Chem. 271: 7630–7634.

Denz H., Orth B., Weiss G., Herrmann R., Huber P., Wachter H. and D. Fuchs (1993) Weight loss in patients with hematological neoplasias is associated with immune system stimulation. Clin. Investig. 71:37–41.

Desmet J., De Maeyer M., Hazes B. And I. Lasters (1992) The Dead End Elimination Theorem and its use in protein side chain positioning. Nature 356: 539–542.

de St. Groth F. and D. Scheidegger (1980) Production of monoclonal antibodies: strategy and tactics. J. Immunol. Methods 35:1–21.

Doherty G. M., Lange J. R., Langstein H. N., Alexander H. R., Buresh C. M. and J. A. Norton (1992) Evidence for IFNγ as a mediator of the lethality of endotoxin and tumor necrosis factor-α. J. Immunol. 149: 1666–1670.

Duong T. T., Finkelman F. D., Singh B. and G. H. Strejan (1994) Effect of anti-interferon-γ monoclonal antibody treatment on the development of experimental allergic encephalomyelitis in resistant mouse strains. J. Neuroimmunol. 53: 101–107.

Duprez E., Tong J-H, Dérré J., Chen S-J, Berger R., Chen Z. And Lanotte M. (1997) JEM-1, a novel gene encoding a leucine-zipper nuclear factor upregulated during retinoid-induced maturation of NB4 promyelocytic leukaemia. Oncogene 14: 1563–1570.

Dustin M. L., Singer K. H., Tuck D. T. and T. A. Springer (1988) Adhesion of T lymphoblasts to epidermal keratinocytes is regulated by interferon-γ and is mediated by intercellular adhesion molecule 1 (ICAM-1). J. Exp. Med. 167: 1323–1340.

Fanger M. W., Morganelli P. M. and P. M. Guyre (1992) Bispecific antibodies. Crit. Rev. Immunol. 12:101.

Fisher C. J. Jr, Agosti J. M., Opal S. M., Lowry S. F., Balk R. A., Sadoff J. C., Abraham E., Schein R. M. and E. Benjamin (1996) Treatment of septic shock with the tumor necrosis factor receptor:Fc fusion protein. The Soluble TNF Receptor Sepsis Study Group. N. Engl. J. Med. 334: 1697–1702.

Freedman A. S., Freeman G. J., Rhynhart K. and L. M. Nadler (1991) Selective induction of B7/BB-1 on interferon-gamma stimulated monocytes: a potential mechanism for amplification of T cell activation through the CD28 pathway. Cell. Immunol. 137: 429–437.

Froyen G., Ronsse I. and A. Billiau (1993) Bacterial expression of a single-chain antibody fragment (SCFV) that neutralizes the biological activity of human interferon-γ. Mol. Immunol. 30:805–812.

Froyen G., Billiau A., Buyse M.-A. and De Waele P. (1995) The expression of a ScFv antibody fragment against IFN-gamma. Med. Fac. Landbouww. Univ. Gent, 60/4a.

Galfre G.and C. Milstein (1981) Preparation of monoclonal antibodies: strategies and procedures. Methods-Enzymol. 73: 3–46.

Genain C. P., Nguyen M.-H., Letvin N. L., Pearl R., Davis R. L., Adelman M., Lees M. B., Linington C. and S. L. Hauser (1995a) Antibody facilitation of multiple sclerosis-like lesions in a nonhuman primate. J. Clin. Invest. 96: 2966–2974.

Genain C. P., Roberts T., Davis R. L., Nguyen M. H., Uccelli A., Faulds D., Li Y., Hedgpeth J. and S. L. Hauser (1995b) Prevention of autoimmune demyelination in non-human primates by a cAMP-specific phosphodiesterase inhibitor. Proc. Natl. Acad. Sci. USA 92: 3601–3605.

Ghetie, M. A. and E. S. Vitetta (1994) Recent developments in immunotoxin therapy. Curr. Opin. Immunol. 6:707.

Gluzman Y. (1981) SV40-transformed simian cells support the replication of early SV40 mutants. Cell 23: 175–82.

Gonzalez-Scarano F., Grossman R. I., Galetta S., Atlas S. W. and D. H. Silberberg (1987) Multiple sclerosis disease activity correlates with gadolinium-enhanced magnetic resonance imaging. Ann. Neurol. 21: 300–306.

Gordon E. J., Myers K. J., Dougherty J. P., Rosen H. and Y. Ron (1995) Both anti-CD11a (LFA-1) and anti-CD11b (MAC-1) therapy delay the onset and diminish the severity of experimental autoimmune encephalomyelitis. J. Neuroimmunol. 62: 153–160.

Gorczynski, R. M. (1995) Regulation of IFN-gamma and IL-10 synthesis in vivo, as well as continuous antigen exposure, is associated with tolerance to murine skin allografts. Cell. Immunol. 160:224–231.

Gottlieb S. L., Gilleaudeau P., Johnson R., Estes L., Woodworth T. G., Gottlieb A. B. and J. G. Krueger (1995) Response of psoriasis to a lymphocyte-selective toxin ($DAB_{389}IL-2$) suggests a primary immune, but not keratinocyte, pathogenic basis. Nature Medicine 1:442.

Griffiths C. E. M., Powles A. V., Leonard J. N., Fry L., Baker B. S. and H. Valdimarsson (1986) Br. Med. J. 293:731–732.

Hartung H. P., Schafer B., Van Der Meide P. H., Fierz W., Heininger K. and K. V. Toyka (1990) The role of interferon-gamma in the pathogenesis of experimental autoimmune disease of the peripheral nervous system. Annal Neurol. 27: 247–257.

Hawkins C. P., Munro P. M. G. and K.Mackenzie (1990) Duration and selectivity of blood-brain barrier breakdown in chronic relapsing experimental allergic encephalomyelitis studied by gadolinium-DTPA and protein markers. Brain 113: 365–378.

Heremans H., Dillen C., Groenen M., Martens E. and A. Billiau (1996) Chronic relapsing experimental autoimmune encephalomyelitis (CREAE) in mice: enhancement by monoclonal antibodies against interferon-gamma. Eur. J. Immunol. 26: 2393–2398.

Hoffman S. J., Looker D. L., Roehrich J. M., Cozart P. E., Durfee S. L., Tedesco J. L. and G. L. Stetler (1990) Expression of fully functional tetrameric human hemoglobin in *Escherichia coli* Proc. Natl. Acad. Sci. USA 87: 8521–8525.

Holliger P., Prospero T. and G. Winter (1993) "Diabodies": small bivalent and bispecific antibody fragments. Proc. Natl. Acad. Sci. USA 90:6444.

Hurle M. R. and M. Gross (1994) Protein engineering techniques for antibody humanization. Curr. Opin. Biotech. 5:428–433.

Huynh H. K., Oger J. and K. Dorovini-Zis (1995) Interferon-beta downregulates interferon-gamma-induced class II MHC molecule expression and morphological changes in primary cultures of human microvessel endothelial cells. J. Neuroimmunol. 60: 63–73.

Iliades P., Kortt A. A. and P. J. Hudson (1997) Triabodies: single chain Fv fragments without a linker form trivalent trimers. FEBS Lett 409:437–441.

Ito W. and Y. Kurosawa (1993) Development of an artificial system with multiple valency using an Fv fragment fused to a fragment of protein A. J. Biol. Chem. 268:20668.

Iwagaki H., Hizuta A., Tanaka N. and K. Orita (1995) Plasma neopterin/C-reactive protein ratio as an adjunct to the assessment of infection and cancer cachexia. Immunol. Investig. 24: 479–487.

Jacob C. O., Holoshitz J., Van Der Meide P., Strober S. and H. O. McDevitt (1989) Heterogeneous effects of IFN-γ in adjuvant arthritis. J. Immunol. 142: 1500–1505.

Jiang H., Milo R., Swoveland P., Johnson KP, Panitch H. and S. Dhib-Jalbut. (1995) Interferon beta-1b reduces interferon gamma-induced antigen-presenting capacity of human glial and B cells. J. Neuroimmunol. 61: 17–25

Kaneko F., Suzuki M., Takiguchi Y., Itoh N. and T. Minagawa (1990) Immunohistopathologic studies in the development of psoriatic lesion influenced by gamma-interferon and the producing cells. J. Dermatol. Sci. 1: 425–434.

Kettleborough C. A., Saldanha J., Heath V. J., Morrison C. J. and M. M. Bendig (1991) Humanization of a mouse monoclonal antibody by CDR-grafting: the importance of framework residues on loop conformation. Protein Engineering 4: 773–783.

Kipriyanov S., Little M., Kropshofer H., Breitling F., Gotter S. and S. Dubel (1996) Affinity enhancement of a recombinant antibody: formation of complexes with multiple valency by a single-chain Fv fragment-core streptavidin fusion. Prot. Eng. 9:203.

Knappik A. and A. Plückthun (1995) Engineered turns of a recombinant antibody improve its in vivo folding. Protein Engineering 8: 81–89.

Kortt A., Lah M., Oddie G., Gruen C., Burns J., Pearce L., Atwell J., McCoy A., Howlet G., Metzger D., Webster R. and P. Hudson (1997) Single-chain Fv fragments of anti-neuramidase antibody NC10 containing five- and ten-residue linkers form dimers and with zero-residue linker a trimer. Prot. Eng. 10:423.

Köhler G. and C. Milstein (1975) Continuous cultures of fused cells secreting antibody of predefined specificity. Nature 256:495.

Kostelny S., Cole M. and Y. Yun Tso (1992) Formation of a bispecific antibody by the use of leucine zippers. J. Immunol. 148:1547.

Kranz D., Gruber M. and E. Wilson (1995) Properties of bispecific single chain antibodies expressed in *E. coli*. J. Hematother. 4:403.

Kreutzer B., Stubiger N., Thiel H. J. and M. Zierhut (1996) Oculomucocutaneous changes as paraneoplastic syndromes. Ger. J. Ophtalmol. 5:176–181.

Kwok A. Y. C., Zu X., Yang C., Alfa M. J. and F. T. Jay (1993) Human interferon- has three domains associated with its antiviral function: a neutralizing epitope typing scheme for human interferon-γ. Immunology 78:131–137.

Landolfo S., Cofano F., Giovarelli M., Pratt M., Cavallo G., and G. Forni (1985) Inhibition of interferon-gamma may suppress allograft reactivity by T lymphocytes in vitro and in vivo. Science 229:176–179.

Langstein H. N., Doherty G. M., Fraker D. L., Buresh C. M. and J. A. Norton (1 991) The roles of γ-interferon and tumor necrosis factor in an experimental rat model of cancer cachexia. Cancer Research 51:2302–2306.

Lewis J. A. (1995) A sensitive biological assay for interferons. J. Immunol. Meth. 185:9–17.

Lorsbach R. B., Murphy W. J., Lowenstein C. J., Snyder S. H. and S. W. Russel (1993) Expression of the nitric oxide synthase gene in mouse macrophages activated for tumor cell killing. J. Biol. Chem. 268: 1908–1913.

Mándi Y., Farkas G., Ocsovszky I. and Z. Nagy (1995) Inhibition of tumor necrosis factor production and ICAM-1 expression by pentoxifylline: beneficial effects in sepsis syndrome. Res. Exp. Med. (Berl) 195: 297–307.

Manning L. R., Jenkins W. T., Hess J. R., Vandegriff K., Winslow R. M. and J. M. Manning (1996) Subunit dissociations in natural and recombinant hemoglobins. Protein Science 5: 775–781.

Massacesi et al. (1995) Active and passively induced experimental autoimmune encephalomyelitis in common marmosets: a new model for multiple sclerosis. Ann. Neurol. 37: 519–530.

Mateo C., Moreno E., Amour K., Lombardero J., Harris W. and R. Perez (1997) Humanization of a mouse monoclonal antibody that blocks the epidermal growth factor receptor: recovery of antagonistic activity. Immunotechnology 3:71–81.

Matthys P., Dijkmans S., Proost P. et al. (1991) Severe cachexia in mice inoculated with interferon-γ producing tumor cells. Int. J. Cancer 49:77–82.

McCarron R. M., Wang L., Racke M. K., Mc Farlin D. E. and M. Spatz (1993) Cytokine-regulated adhesion between encephalitogenic T lymphocytes and cerebrovascular endothelial cells. J. Neuroimmunol. 43: 23–30.

McCutchan J. H. and J. S. Pagano (1968) Enchancement of the infectivity of simian virus 40 deoxyribonucleic acid with diethylaminoethyl-dextran. J-Natl-Cancer-Inst. 41: 351–7.

Megahed M. (1996) Histology of subepidermal bullous dermatoses. Verh. Dtsch. Ges. Pathol. 80:223–228.

Meissner K., Weyer U., Kowalzick L. and J. Altenhoff (1991) Successful treatment of primary progressive follicular mucinosis with interferons. J. Am. Acad. Dermatol. 24:848–850.

Miethke T., Duschek K., Wahl C, Heeg K. and H. Wagner (1993) Pathogenesis of the toxic shock syndrome: T cell mediated lethal shock caused by the superantigen TSST-1. Eur. J. Immunol. 23: 1494–1500.

Montero-Julian F. A., B. Klein, E. Gautherot and H. Brailly (1995) Pharmacokinetic study of anti-interleukin-6 (IL-6) clearance by coctails of anti-IL-6 antibodies. Blood 85: 917–924.

Morel P., Revillard J-P., Nicolas J-F., Vijdenes J., Rizova H. and J. Thivolet (1992) J. Autoimmunity 4:465–477.

Mould R. M., Hoffman O. M. and T. Brittain (1994) Production of human embryonic haemoglobin (Gower II) in a yeast expression system. Biochem. J. 298: 619–622.

Nepom G. T. (1993) MHC and Autoimmune Diseases. Immunol. Ser. 59: 143–164.

Neu H. C. and L. A. Heppel (1965) The release of enzymes from *Escherichia coli* by osmotic shock and during the formation of spheroplasts. J. Biol. Chem. 240:3685–3692.

Nickoloff B. J. (1988) Role of interferon-gamma in cutaneous trafficking of lymphocytes with emphasis on molecular and cellular adhesion events. Arch. Dermatol. 124: 1835–1843.

Novelli F., Giovarelli M., Reber-Liske R., Virgallita G., Garotta G. and G. Forni (1991) Blockade of physiologically secreted IFN-γ inhibits human T lymphocyte and natural killer cell activation. J. Immunol. 147:1445–1452.

Olerup O. and J. Hillert (1991) HLA class II-associated genetic susceptibility in multiple sclerosis: a critical evaluation. Tissue antigens 38:1–15.

Olson J. S., Eich R. F., Smith L. P., Warren J. J. and Knowles B. C. (1997) Protein engineering strategies for designing more stable hemoglobin-based blood substitutes. Artif. Cells Blood Substit. Immobil. Biotechnol., 25: 227–241.

Ozmen L., Pericin M., Hakimi J., Chizzonite R. A., Wysocka M., Trinchieri G, Gately M. and G. Garotta (1994) Interleukin 12, Interferon γ, and Tumor Necrosis Factor α Are the Key Cytokines of the Generalized Shwartzman Reaction. J. Exp. Med. 180: 907–915.

Ozmen L., Roman D., Fountoulakis M., Schmid G., Ryffel B. And G. Garotta (1995) Experimental therapy of systemic lupus erythematosus: the treatment of NZB/W mice with mouse soluble interferon-γ receptor inhibits the onset of glomerulonephritis. Eur. J. Immunol. 25: 6–12.

Pace J. L., Russell S. W., Torres B. A., Johnson H. M. and P. W. Gray (1983) Recombinant mouse γ interferon induces the priming step in macrophage activation for tumor cell killing. J.Immunol. 130: 2011–2013.

Pack P. and A. Plückthun (1992) Miniantibodies : use of amphipathic helices to produce functional, flexibly linked dimeric Fv fragments with high avidity in *Escherichia coli*. Biochemistry 31: 1579–1584.

Pack P., Kujau M., Schroekh V., Knüpfer U., Wenderoth R., Riesenberg D. and A. Plückthun (1993) Improved bivalent miniantibodies, with identical avidity as whole antibodies, produced by high cell density fermentation of *Escherichia coli*. Bio/Technology 11: 1271–1277.

Pack P., Müller K., Zahn R. and A. Plückthun (1995) Tetravalent miniantibodies with high avidity assembling in *Escherichia coli*. J. Mol. Biol. 246: 28–34.

Page M. and Thorpe R. (1996) Purification of IgG using protein A or protein G. In: The protein protocols handbook. Walker J. M. (Ed.), Human Press, Totowa, N.J., pp. 733.

Pagnier J., Baudin V. and C. Poyart (1992) Expression of recombinant human hemoglobin. Rev. Fr. Transfus. Hemobiol. 35: 407–415.

Panitch H. S. (1994) Influence of infection on exacerbations of multiple sclerosis. Ann. Neurol. 36 (suppl) S25–28

Panitch H. S., Haley A. S., Hirsch R. L. and K. P. Johnson (1986) A trial of interferon gamma in multiple sclerosis: clinical results. Neurology 36 (suppl. 1): 285

Pantaleeva G. A. (1990) Paraneoplastic bullous dermatoses. Vestn. Dermatol. Venerol. 2:50–52.

Park S. S., Ryu C. J., Gripon P., Guguen-Guillouzo C. and H. J. Hong (1996) Generation and characterization of a humanized antibody with specificity for preS2 surface antigen of hepatitis B virus. Hybridoma 15:435–441.

Perry M. and Kirby H. (1990) Monoclonal antibodies and their fragments. In: Protein purification applications, a practical approach. Harris E. L. V., Angal S. (Eds.), Oxford University Press, Oxford, UK. pp. 147–156.

Pettit D. K. and W. R. Gombotz (1998) The development of site-specific drug-delivery systems for protein and peptide biopharmaceuticals. Tibtech. 16: 343.

Pin S., Royer C. A., Gratton E., Alpert B. and G. Weber (1990) Subunit interactions in hemoglobin probed by fluorescence and high-pressure techniques. Biochemistry 29: 9194–9202.

Plückthun A. and P. Pack (1997) New protein engineering approaches to multivalent and bispecific antibody fragments. Immunotechnology 3: 83–105.

Poljak R. J. (1994) Production and structure of diabodies. Structure 2:1121–1123.

Rep M. H., Hintzen R. Q., Polman C. H. and R. A. Van Lier (1996) Recombinant interferon-beta blocks proliferation but enhances interleukin-10 secretion by activated human T-cells. J. Neuroimmunol. 67: 111–118.

Reinhart K., Wiegand-LIohnert C., Grimminger F., Kaul M., Withington S., Treacher D., Eckart J., Willatts S., Bouza C., Krausch D., Stockenhuber F., Eiselstein J., Daum L. and J. Kempeni (1996) Assessment of the safety and efficacy of the monoclonal anti-tumor necrosis factor antibody-fragment, MAK 195F, in patients with sepsis and septic shock: a multicenter, randomized, placebo-controlled, dose-ranging study. Crit. Care Med. 24: 733–742.

Reuss-Borst M. A., Pawalec G., Saal J. G., Horny H. P., Muller C. A. and H. D. Waller (1993) Sweet's syndrome associated with myelodysplasia: possible role of cytokines in the pathogenesis of the disease. Br. J. Haematol. 84:356–358.

Roguska M. A., Pedersen J. T., Keddy C. A., Henry A. H., Searle S. J., Lambert J. M., Goldmacher V. S., Blättler W. A., Rees A. R. and B. C. Guild (1994) Humanization of murine monoclonal antibodies through variable domain resurfacing. Proc. Natl. Acad. Sci. USA 91: 969–973.

Rubio M. A., Sotillos M., Jochems G., Alvarez V. and A. L. Corbi (1995) Monocyte activation: rapid induction of $\alpha1/\beta1$ (VLA-1) integrin expression by lipopolysaccharide and interferon-. Eur. J. Immunol. 25: 2701–2705.

Saha B., Harlan D. M., Lee K. P., June C. H. and R. Abe (1996) Protection Against Lethal Toxic Shock by Targeted Disruption of the CD28 Gene. The Journal of Experimental Medicine 183: 2675–2680.

Sandvig S., Laskay T., Andersson J., De Ley M. and U. Andersson (1987) Gamma-interferon is produced by $CD3^+$ and $CD3^{31}$ lymphocytes. Immun. Rev. 97:51–65.

Schon M. P., Detmar M. and C. M. Parker (1997) Murine psoriasis-like disorders induced by naive $CD4^+$ cells. Nature Medicine 3:183.

Smoller B. R. and J. Bortz (1993) Immunophenotypic analysis suggests that granuloma faciale is a gamma-interferon-mediated process. J. Cutan. Pathol. 20:442–446.

Snapper C. M. and W. E. Paul (1987) Interferon-γ and B cell stimulatory factor-1 reciprocally regulate Ig isotype production. Science 236: 944–947.

Somner N., Loschmann P.-A., Northoff G. H., Weller M., Steinbrecher A., Steinbach J. P., Lichtenfels R., Meyermann R., Riethmuller A., Fontana A., Dichgans J. and R. Martin (1995) The antidepressant rolipram suppresses cytokine production and prevents autoimmune encephalomyelitis. Nature Med. 1: 244–248.

Srere P. A. and Mathews C. K. (1990) Purification of multienzyme complexes. Methods in Enzymology 182:539–552.

Steinman R. M., Noguiera N., Witmer M. D., Tydings J. G. and I. S. Mellman (1980) Lymphokine enhances the expression and synthesis of Ia antigens on cultural mouse peritoneal macrophages. J. Exp. Med. 152: 1248–1261.

Steffen B. J., Butcher E. C. and B. Engelhardt (1994) Evidence for involvement of ICAM-1 and VCAM-1 in lymphocyte interaction with endothelium in experimental autoimmune encephalomyelitis in the central nervous system in SJL/J mouse. Am. J. Pathol. 145: 189–201.

Stemmer W. P., Crameri A., Ha K. D., Brennan T. M. and Heyneker H. L. (1995) Single-step assembly of a gene and entire plasmid from large numbers of oligodeoxyribonucleotides. Gene 164: 49–53.

Sutherland-Smith A. J., Baker H. M., Hofmann O. M., Brittain T. and E. N. Baker (1998) Crystal structure of a human embryonic haemoglobin: the carbonmonoxy form of gower II (alpha2epsilon2) haemoglobin at 2.9 Å resolution. J.Mol. Biol. 280: 475–484.

Tang H., Mignon-Godefroy K., Meroni P. L., Garotta G., Charreire J. and F. Nicoletti (1993) The effects of a monoclonal antibody to interferon-γ on experimental autoimmune thyroiditis (EAT): prevention of disease and decrease of EAT-specific T cells. Eur. J. Immunol. 23: 275–278.

Teraki Y., Imanishi K. and T. Shiohara (1996) Ofuji's disease and cytokines: remission of eosinophilic pustular folliculutis associated with increased serum concentrations of interferon gamma. Dermatology 192:16–18.

Terrell T. G. and J. D. Green (1993) Comparative pathology of recombinant murine interferon- in mice and recombinant human interferon-γ in cynomolgus monkeys. Int. Rev. Exp. Pathology 34B: 73–101.

Terskikh A. V., Le Doussal J-M., Crameri R., Fisch I., Mach J-P. and A. V. Kajava (1997) "Peptabody": a new type of high avidity binding protein. Proc. Natl. Acad. Sci. USA 94: 1663–1668.

Tracey K. J. (1991) Tumor necrosis factor (cachectin) in the biology of septic shock syndrome. Circ. Shock 35: 123–128.

Tsukada N., Matsuda M., Miyagi K. and N. Yanagisawa (1993) Cytotoxicity of T cells for cerebral endothelium in multiple sclerosis. J. Neurol. Sci. 117: 140–147.

Turano A., Balsari A., Viani E., Landolfo S., Zanoni L., Gargiulo F. and A. Caruso (1992) Natural human antibodies to γ interferon interfere with the immunomodulating activity of the lymphokine. Proc. Natl. Acad. Sci. USA 89:4447–4451.

Valdimarsson H., Baker B. S., Jonsdottir I., Powles A. and L. Fry.(1995) Psoriasis: a T-cell-mediated autoimmune disease induced by streptococcal superantigens? Immunol. Today 16:145.

Van den Oord J. J., De Ley M. and C. De Wolf-Peeters (1995) Distribution of interferon-gamma receptors in normal and psoriatic skin. Path. Res. Pract. 191:530–534.

Villinger F., Hunt D., Mayne A., Vuchetich M., Findley H. and A. A. Ansari (1993) Qualitative and quantitative studies of cytokines synthesized and secreted by non-human primate peripheral blood mononuclear cells. Cytokine 5:469–479.

Vowels B. R., Lessin S. R., Cassin M., Jaworsky C., Benoit B., Wolfe J. T. and A. H. Rook (1994) Th2 cytokine mRNA expression in skin in cutaneous T-cell lymphoma. J. Invest. Dermatol. 103:669–673.

Waisman A., P. J. Ruiz, D. L. Hirschberg, A. Gelman, J. R. Oksenberg, S. Brocke, F. Mor, I. R. Cohen and L. Steinman (1996) Suppressive vaccination with DNA encoding a variable region gene of the T-cell receptor prevents autoimmune encephalomyelitis and activates Th2 immunity. Nature Medicine 2: 899–905.

Wakabayashi G., Gelfand J. A., Burke J. F., Thompson R. C. and C. A. Dinarello (1991) A specific receptor antagonist for interleukin-1 prevents Escherichia coli-induced septic shock during lethal bacteremia. Nature 330: 662–664.

Waldburger K. E., Hastings R. C., Schaub R. G., Goldman S. J. and J. P. Leonard (1996) Adoptive transfer of experimental allergic encephalomyelitis after in vitro treatment with recombinant murine interleukin-12. Preferential expansion of interferon-gamma-producing cells and increased expression of macrophage-associated inducible nitric oxide synthase as immunomodulatory mechanisms. Am. J. Pathol. 148: 375–82.

Wherry J., Wenzel R., Wunderik R. et al. (1993) Monoclonal antibody to human tumor necrosis factor (TNFα MAb): Multicenter efficacy and safety study in patients with sepsis syndrome. Presented at the 33th Interscience Conference Antimicrobial Agents and Chemotherapy, New Orleans; abstract 696.

Willenborg D. O., Fordham S. A., Cowden W. B. and I. A. Ramshaw (1995) Cytokines and murine autoimmune encephalomyelitis: inhibition or enhancement of disease with antibodies to select cytokines, or by delivery of exogenous cytokines using a recombinant vaccinia virus system. Scand. J. Immunol. 41: 31–41.

Williams K. C., Ulvestad E. and W. F. Hickey (1994) Immunology of multiple sclerosis. Clin. Neurosci. 2: 229–245.

Willsteed E., Bhogal B. S., Das A. K., Wojnarowska F., Black M. M. and P. H. McKee (1991) Lichen planus pemphigoides: a clinicopathological stidy of nine cases. Histopathology 19:147–154.

Wood G. S., Michie S. A., Durden F., Hoppe R. T and R. A. Warnke (1994) Expression of class II major histocompatibility antigens by keratinocytes in cutaneous T cell lymphoma. Int. J. Dermatol. 33:346–350.

Xu Y., Oomen R. and M. H. Klein (1994) Residue at position 331 in the IgG1 and IgG4 CH2 domains contributes to their differential ability to bind and activate complement. J. Biol. Chem. 269:3469–74.

Youl B. D., Turano G., Miller D. H., Towell A. D., MacManus D. G., Moore S. G., Jones S. J., Barrett G., Kendall B. E., Moseley I. F., Tofts P. S., Halliday A. M. and W. I. McDonald (1991) The pathophysiology of acute optic neuritis. Brain 114: 2437–2450.

Yu C.-L., Haskard D. O., Cavender D., Johnson A. R. and M. Ziff (1985) Human gamma interferon increases binding of T lymphocytes to endothelial cells. Clin. Exp. Immunol. 62: 554–560.

Zeni F., Pain P., Vindimian M; Gay J. P., Gery P., Bertrand M., Page Y., Vermesch R. and J. C. Bertrand (1996) Effects of pentoxifylline on circulating cytokine concentrations and hemodynamics in patients with septic shock: results from a double-blind, randomized, placebo-controlled study. Crit. Care Med. 24: 207–214.

Zhu Z., Zapata G., Shalaby R., Snedecor B., Chen H. and P. Carter (1996) High level secretion of a humanized bispecific diabody from Escherichia coli. Biotechnology 14:192–196.

What is claimed is:

1. An isolated molecule which binds and neutralizes interferon-gamma selected from the group consisting of:
- a scFv comprising a humanized variable domain, wherein said variable domain comprises amino acids 1–117 and 133–239 of SEQ ID) NO: 85;

a chimeric antibody comprising:

a) a humanized heavy chain variable domain, said heavy chain variable domain having an amino acid sequence as shown in positions 1–117 of SEQ ID NO: 85, and b) the humanized light chain variable domain, said light chain variable domain having an amino acid sequence as shown in positions 133–239 of SEQ ID NO: 85;

a diabody comprising:

a) a humanized heavy chain variable domain, said heavy chain variable domain having an amino acid sequence as shown in positions 1–117 of SEQ ID NO: 85, and b) a humanized light chain variable domain, said light chain variable domain having an amino acid sequence as shown in positions 133–239 of SEQ ID NO: 85; and, a multivalent antibody, wherein said multivalent antibody is selected from the group consisting of a triabody, a tetravalent antibody, a peptabody, and a hexabody, and wherein said multivalent antibody comprises:

a) a humanized heavy chain variable domain, said variable domain comprising amino acids 1–117 of SEQ ID NO: 85; and b) a humanized light chain variable domain, said variable domain comprising amino acids 133–239 of SEQ ID NO: 85.

2. An isolated molecule according to claim 1, wherein said triabody further comprises:

a) three variable domains of three different anti-interferon-gamma antibodies, or b) at least one variable domain of an anti-interferon-gamma antibody in combination with i) at least one variable domain of a different anti-interferon-gamma antibody, or ii) at least one variable domain of an antibody which binds to another molecule excluding interferon-gamma;

wherein at least one of the variable domains comprises amino acids 1–117 and 133–239 of SEQ ID NO:85.

3. The isolated molecule according to claim 1, which is a triabody further comprising three identical variable domains of an anti-interferon-gamma antibody.

4. The isolated molecule according to claim 1, which is a triabody further comprising three identical humanized scFvs, wherein each scFv has a zero residue linker joining the humanized heavy chain variable domain to the humanized light chain variable domain.

5. The isolated molecule according to claim 1, which is a tetravalent antibody further comprising:

a) four variable domains of four different anti-interferon-gamma antibodies, or b) at least one variable domain of an anti-interferon-gamma antibody in combination with
i) at least one variable domain of another anti-interferon-gamma antibody, or
ii) an antibody which binds to another molecule excluding interferon gamma;

wherein at least one of the variable domains comprises amino acids 1–117 and 133–239 of SEQ ID NO:85.

6. The isolated molecule according to claim 1, which is a tetravalent antibody further comprising four identical variable domains of an anti-interferon-gamma antibody.

7. The isolated molecule according to claim 1, which is a tetravalent antibody further comprising four identical humanized scFvs as a homodimer of two identical molecules, each containing two humanized scFvs and a dimerization domain.

8. The isolated molecule according to claim 7, wherein each said scFv comprises amino acids 1–239 of SEQ ID NO: 85.

9. The isolated molecule according to claim 1, which is a tetravalent antibody further comprising:

a) a full-sized humanized antibody wherein said antibody comprises two heavy chains and two light chains, and b) two humanized scFvs wherein each scFv is attached by its carboxy-terminus to a carboxy-terminus of one of said antibody's heavy chains, and wherein each said scFv comprises amino acids 1–239 of SEQ ID NO: 85.

10. The isolated molecule according to claim 1, which is either a peptabody comprising five identical variable domains of an anti-interferon-gamma antibody, or a hexabody comprising six identical variable domains of an anti-interferon-gamma antibody.

11. The isolated molecule according to claim 1, which is either a peptabody comprising five identical humanized scFvs, or a hexabody comprising six identical humanized scFvs.

12. The isolated molecule according to claim 11, wherein each said scFv comprises amino acids 1–239 of SEQ ID NO: 85.

13. The isolated molecule according to claim 1, which is either a) a peptabody comprising a combination of 1 to 4 variable domains from an anti-interferon-gamma antibody and, respectively, 4 to 1 variable domain(s) of an antibody which binds to another molecule other than interferon gamma, wherein at least one of the variable domains comprises amino acids 1–117 and 133–239 of SEQ ID NO:85; or b) a hexabody comprising a combination of 1 to 5 variable domains from an anti-interferon-gamma antibody and, respectively, 5 to 1 variable domain(s) of an antibody which binds to another molecule other than interferon gamma, wherein at least one of the variable domains comprises amino acids 1–117 and 133–239 of SEQ ID NO:85.

14. The molecule according to claim 1, which is either:

a) a peptabody comprising five variable domains from five different anti-interferon-gamma antibodies, wherein at least one of the variable domains comprises amino acids 1–117 and 133–239 of SEQ ID NO:85; or b) a hexabody comprising six variable domains from six different anti-interferon-gamma antibodies, wherein at least one of the variable domains comprises amino acids 1–117 and 133–239 of SEQ ID NO:85.

* * * * *

UNITED STATES PATENT AND TRADEMARK OFFICE
CERTIFICATE OF CORRECTION

PATENT NO.    : 6,350,860 B1
DATED         : February 26, 2002
INVENTOR(S)   : Marie-Ange Buyse and Erwin Sablon It is certified that error appears in the above-identified patent and that said Letters Patent is hereby corrected as shown below:

<u>Title page,</u>
Item [73], country for Assignee should be -- BE --.

<u>Column 9,</u>
Line 65, delete "intron+" and begin line 66 with -- intron+ --.

<u>Column 12,</u>
Lines 37 and 38, delete "8:9" and insert -- 89 -- therefor.

<u>Column 13,</u>
Line 15, delete "IFN" and insert -- IFNγ -- therefor.

<u>Column 14,</u>
Line 16, delete "a ruminant antibody".

<u>Column 15,</u>
Line 52, delete "IFN" and insert -- IFNγ -- therefor.

<u>Column 16,</u>
Line 19, delete "TNFαa" and insert -- TNFα -- therefor.

<u>Column 20,</u>
Line 27, delete "The as" and insert -- The scFv was -- therefor.

<u>Column 27,</u>
Line 46, delete "5 1/min" and insert -- 5 μl/min -- therefor.
Line 47, delete "17 1" and insert -- 17 μl -- therefor.
Line 48, delete "35 L" and insert -- 35 μl -- therefor.
Line 48, delete "3 g/ml" and insert -- 3μg/ml -- therefor.
Line 50, delete "17 l" and insert -- 17μl -- therefor.
Line 52, delete "3 g/ml" and insert -- 3μg/ml -- therefor.

<u>Columns 29 and 30,</u>
Line 22, delete "C 1" and insert -- Cγl -- therefor.

UNITED STATES PATENT AND TRADEMARK OFFICE
CERTIFICATE OF CORRECTION

PATENT NO. : 6,350,860 B1
DATED : February 26, 2002
INVENTOR(S) : Marie-Ange Buyse and Erwin Sablon It is certified that error appears in the above-identified patent and that said Letters Patent is hereby corrected as shown below:

Column 31,
Line 40, delete "IG81756" and insert -- IG8175→ -- therefor.
Line 47, delete "IG81747" and insert -- IG8174← -- therefor.

Column 33,
Line 44, delete "IG81756" and insert -- IG8175→ -- therefor.
Line 51, delete "IG81737" and insert -- IG8173← -- therefor.
Line 58, delete "IG8168(sense)".

Column 35,
Line 63, delete "*Construction of mammalian expression plasmids" and at line 65 insert the heading -- Construction of mammalian expression plasmids --.

Column 38,
Line 47, delete "100MM" and insert -- 100mM -- therefor.

Column 40,
Line 11, delete "Aanti-IFNγ" and insert -- Anti IFNγ -- therefor.

Column 43,
Line 25, delete "CCGGGAGCGGAmTTGAACG" and insert
-- CCGGGAGCGGATTTGAACG -- therefor.
Line 60, delete "1551 TTTTmGTGATGCTCGTCAGGGGGGCG-" and insert
-- 1551 TTTTTGTGATGCTCGTCAGGGGGGCG- -- therefor.

Column 45,
Line 65, delete "*Construction of mammalian expression plasmids".

Column 46,
Line 1, insert the heading -- Construction of mammalian expression plasmids --.

Column 51,
Line 61, delete "30 g F3" and insert -- 30µg F3 -- therefor.

UNITED STATES PATENT AND TRADEMARK OFFICE
CERTIFICATE OF CORRECTION

PATENT NO.   : 6,350,860 B1
DATED        : February 26, 2002
INVENTOR(S)  : Marie-Ange Buyse and Erwin Sablon It is certified that error appears in the above-identified patent and that said Letters Patent is hereby corrected as shown below:

<u>Column 53,</u>
Lines 3 and 46, delete "7.2." and insert -- 8.2 -- therefor.

<u>Column 119,</u>
Line 5, delete "SEQ ID)" and insert -- SEQ ID -- therefor.

Signed and Sealed this

Twelfth Day of November, 2002

Attest:

JAMES E. ROGAN
Attesting Officer  Director of the United States Patent and Trademark Office